US009725518B2

(12) United States Patent
Banham et al.

(10) Patent No.: US 9,725,518 B2
(45) Date of Patent: Aug. 8, 2017

(54) ANTIBODIES THAT BIND TO JAGGED 1

(71) Applicant: Cancer Research Technology Limited, London (GB)

(72) Inventors: Alison Hilary Banham, London (GB); Adrian Llewellyn Harris, London (GB); Penelope Ann Handford, London (GB); Susan Mary Lea, London (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 14/761,062

(22) PCT Filed: Jan. 15, 2014

(86) PCT No.: PCT/GB2014/050104
§ 371 (c)(1),
(2) Date: Jul. 15, 2015

(87) PCT Pub. No.: WO2014/111704
PCT Pub. Date: Jul. 24, 2014

(65) Prior Publication Data
US 2016/0108128 A1 Apr. 21, 2016

(30) Foreign Application Priority Data
Jan. 15, 2013 (GB) .................. 1300706.7

(51) Int. Cl.
| | | |
|---|---|---|
| *A61K 39/395* | (2006.01) | |
| *C12N 15/00* | (2006.01) | |
| *C12N 5/00* | (2006.01) | |
| *C07K 16/00* | (2006.01) | |
| *C07K 16/28* | (2006.01) | |
| *A61K 45/06* | (2006.01) | |
| *C07K 16/30* | (2006.01) | |
| *A61K 39/00* | (2006.01) | |
| *A61N 5/10* | (2006.01) | |

(52) U.S. Cl.
CPC ...... *C07K 16/2896* (2013.01); *A61K 39/3955* (2013.01); *A61K 39/39558* (2013.01); *A61K 45/06* (2013.01); *C07K 16/3015* (2013.01); *C07K 16/3046* (2013.01); *C07K 16/3061* (2013.01); *C07K 16/3069* (2013.01); *A61K 2039/505* (2013.01); *A61N 2005/1098* (2013.01); *C07K 2317/14* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS 9,127,053 B2 * 9/2015 West ...................... C07K 16/18

FOREIGN PATENT DOCUMENTS

WO WO-2011/063237 A2 5/2011

OTHER PUBLICATIONS

Paul, Fundamental Immunology, 3rd Edition, 1993, pp. 292-295, under the heading "Fv Structure and Diversity in Three Dimensions".*
Rudikoff et al (Proc. Natl. Acad. Sci.USA, 79(6):1979-1983, Mar. 1982.*
Colman P. M. Research in Immunology, 145:33-36, 1994.*
Cordle, J. et al., "A Conserved Face of the Jagged/Serrate DSL Domain is Involved in Notch Trans-Activation and Cis-Inhibition," *Nature Structural & Molecular Biology*, vol. 15, No. 8, pp. 1-24, 2008.
Demin, L. et al., "Development of Therapeutic Anti-Jagged1 Monoclonal Antibodies," Scientific Program 5th EuroMAbnet, retrieved from the Internet URL: http://www.euromabnet.com/meeting/5th-EuroMabNet-Meeting-Agenda.pdf, last retrieved on Mar. 6, 2014.
International Search Report and Written Opinion for PCT/GB2014/050104, mailed on Mar. 31, 2014, 14 pages.

* cited by examiner

*Primary Examiner* — Shulamith H Shafer
(74) *Attorney, Agent, or Firm* — McCarter & English, LLP; Jill Ann Mello

(57) ABSTRACT

The present invention provides antibodies which bind to the Delta/Serrate/LAG-2 consensus sequence (DSL) domain of human Jagged 1 via novel epitopes comprising the residue E228, and inhibit the interaction between human Jagged 1 and its associated receptors. Said antibodies may be administered therapeutically in the treatment of tumors/cancer, preferably those associated with tumoral Jagged 1-mediated signalling and tumor microenvironmental processes in which Jagged 1 and/or Notch-mediated signalling has been implicated, including those comprising Jagged 1-mediated cross talk between the tumor and the tumor microenvironment. The present invention also provides pharmaceutical compositions comprising said antibodies, uses of said antibodies in therapy, hybridomas comprising and/or secreting said antibodies and cells or cell lines expressing said antibodies and humanized/deimmunized variants in recombinant form.

17 Claims, 24 Drawing Sheets

A

B

A

B

*P<0.05; P<0.01; *P<0.001; ****P<0.0001
DBZ vs DMSO ***P<0.001, ns = not significant

*P<0.05; P<0.01; *P<0.001; ****P<0.0001
DBZ vs DMSO ***P<0.001, ns = not significant J1-183D CDR sequences

|  | CDR1 | CDR2 | CDR3 |
|---|---|---|---|
| VL Wildtype | RTSENIYSYLT | NAKILAAGV | QHHYDIPWT |
| VL1 | RTSENIYSYLT | NAKILAAGV | QHHYDIPWT |
| VL2 | RTSENIYSYLT | NAKTLASGV | QHHYDIPWT |
| VL3 | RTSENIYSYLT | NAKILDSGV | QHHYDIPWT |
| VL4 | RTSENIYSYLT | HAKILDSGV | QHHYDIPWT |
|  |  |  |  |
| VH wildtype | DYAIH | NTYYGDSKYNQKFKD | GYDGFAY |
| VH1 | DYAIH | NTYYGDSKYNQKFKD | GYDGFAY |
| VH2 | DYAIH | NTYYGDSKYAQKFQG | GYDGFAY |
| VH3 | DYAIH | NTYYGDSKYAQKFQG | GYDGFAY |
| VH4 | DYAIH | NTYYGDSKYAQKFQG | GYDGFAY |

Light chain sequences
J1-183D_VL
MSVPTQVLGLLLLWLTDARCDIQLTQSPASLSASVGETVTFTCRTSENIYSYLTWYQQKQGKSPQ
LLVYNAKILAAGVPSRFSGYGSGTQFSLKINSLQPEDFGTYYCQHHYDIPWTFGGGTKLEIKRT
(SEQ ID NO.57)
J1-183D_VL_1
MSVPTQVLGLLLLWLTDARCDIQMTQSPSSLSASVGDRVTITCRTSENIYSYLTWYQQKPGKAPKL
LVYNAKILAAGVPSRFSGSGSGTDFTLTISSLQPEDFATYYCQHHYDIPWTFGGGTKLEIKRT (SEQ
ID NO.58)
J1-183D_VL_2
MSVPTQVLGLLLLWLTDARCDIQMTQSPSSLSASVGDRVTITCRTSENIYSYLTWYQQKPGKAPKL
LIYNAKTLASGVPSRFSGSGSGTDFTLTISSLQPEDFATYYCQHHYDIPWTFGGGTKLEIKRT (SEQ
ID NO.59)
J1-183D_VL_3
MSVPTQVLGLLLLWLTDARCDIQMTQSPSSLSASVGDRVTITCRTSENIYSYLTWYQQKPGKAPKL
LIYNAKILDSGVPSRFSGSGSGTDFTLTISSLQPEDFATYYCQHHYDIPWTFGGGTKLEIKRT (SEQ
ID NO.60)
J1-183D_VL_4
MSVPTQVLGLLLLWLTDARCDIQMTQSPSSLSASVGDRVTITCRTSENIYSYLTWYQQKPGKAPKL
LIYHAKILDSGVPSRFSGSGSGTDFTLTISSLQPEDFATYYCQHHYDIPWTFGGGTKLEIKRT(SEQ
ID NO.61)

Heavy chain sequences
J1-183D_VH
MEWSWVFLFFLSVTTGVHSQVQLQQPGTELVRPGVSVKISCKVSGYAFTDYAIHWIMQSHAKSLE
WIGIINTYYGDSKYNQKFKDKATMTVDKSSNTAYMELARLTSEDSAIYYCARGYDGFAYWGQGTL
VTVSSASTKGP (SEQ ID NO.62)
J1-183D_VH_1
MEWSWVFLFFLSVTTGVHSQVQLVQSGAELKKPGASVKVSCKVSGYAFTDYAIHWIRQAPGQGL
EWMGIINTYYGDSKYNQKFKDRVTMTVDKSTSTAYMELSSLRSEDTAVYYCARGYDGFAYWGQG
TLVTVSSASTKGP (SEQ ID NO.63)
J1-183D_VH_2
MEWSWVFLFFLSVTTGVHSQVQLVQSGAELKKPGASVKVSCKVSGYAFTDYAIHWIRQAPGQGL
EWMGIINTYYGDSKYAQKFQGRVTMTVDTSTSTAYMELSSLRSEDTAVYYCARGYDGFAYWGQG
TLVTVSSASTKGP (SEQ ID NO.64)
J1-183D_VH_3
MEWSWVFLFFLSVTTGVHSQVQLVQSGAELKKPGASVKVSCKVSGYAFTDYAIHWVRQAPGQGL
EWMGIINTYYGDSKYAQKFQGRVTMTVDTSTSTAYMELSSLRSEDTAVYYCARGYDGFAYWGQG
TLVTVSSASTKGP (SEQ ID NO.65)
J1-183D_VH_4
MEWSWVFLFFLSVTTGVHSQVQLVQSGAEVKKPGASVKVSCKASGYTFTDYAIHWVRQAPGQG
LEWMGIINTYYGDSKYAQKFQGRVTMTVDTSTSTAYMELSSLRSEDTAVYYCARGYDGFAYWGQ
GTLVTVSSASTKGP (SEQ ID NO.66)

Figure 23

J1-65D CDR sequences

| | CDR1 | CDR2 | CDR3 |
|---|---|---|---|
| VL Wildtype | RASGNIHNYLA | NAKTLADDI | QHFWSAPWT |
| VL1 | RASGNIHNYLA | NAKTLADDV | QHFWSAPWT |
| VL2 | RASGNIHNYLA | NAKTLADAV | QHFWSAPWT |
| VL3 | RASGNIHNYLA | NAKTLADAV | QHFWSAPWT |
| VL4 NB non-functional | RASQGIHNYLA | NAKTLADAV | QQFWSAPWT |
| | | | |
| VH wildtype | DYEMH | QPGGGGTAYNQKFKG | RGYDDYPFAY |
| VH1 | DYEMH | QPGGGGTAYNQKFKG | RGYDDYPFAY |
| VH2 | DYEMH | QPGGGGTAYAQKFKG | RGYDDYPFAY |
| VH3 | DYEMH | QPGGGGTAYAQKFQG | RGYDDYPFAY |
| VH4 | DYEMH | QPGGGGTAYAQKFQG | RGYDDYPFAY |

Light chain sequences
J1-65D_VL
MSVPTQVLGLLLLWLTDARCDIQLTQSPASLSASVGETVTITCRASGNIHNYLAWYQQKQGKSPQLLVYNAKTLADDIPSRFSGSGSGTQYSLKINSLQPEDFGSYYCQHFWSAPWTFGGGTKLEIKRT (SEQ ID NO.67)

J1-65D_VL_1
MSVPTQVLGLLLLWLTDARCDIQMTQSPSSLSASVGDRVTITCRASGNIHNYLAWYQQKPGKAPKLLIYNAKTLADDVPSRFSGSGSGTDYTLTISSLQPEDFATYYCQHFWSAPWTFGGGTKLEIKRT (SEQ ID NO.68)

J1-65D_VL_2
MSVPTQVLGLLLLWLTDARCDIQMTQSPSSLSASVGDRVTITCRASGNIHNYLAWYQQKPGKAPKLLIYNAKTLADAVPSRFSGSGSGTDYTLTISSLQPEDFATYYCQHFWSAPWTFGGGTKLEIKRT (SEQ ID NO.69)

J1-65D_VL_3
MSVPTQVLGLLLLWLTDARCDIQMTQSPSSLSASVGDRVTITCRASGNIHNYLAWYQQKPGKAPKLLIYNAKTLADAVPSRFSGSGSGTDYTLTISSLQPEDFATYYCQHFWSAPWTFGQGTKLEIKRT (SEQ ID NO.70)

J1-65D_VL_4
MSVPTQVLGLLLLWLTDARCDIQMTQSPSSLSASVGDRVTITCRASQGIHNYLAWYQQKPGKAPKLLIYNAKTLADAVPSRFSGSGSGTDYTLTISSLQPEDFATYYCQQFWSAPWTFGQGTKLEIKRT (SEQ ID NO.71)

Heavy chain sequences
J1-65D_VH
MEWSWVFLFFLSVTTGVHSQVQLQQPGAELVRPGASVKLSCKALGYTFTDYEMHWVKETPVHGLEWIGAIQPGGGGTAYNQKFKGKATLTADKSSTAYMELSSLTSEDSAVYYCTRRGYDDYPFAYWGQGTLVTVSSASTKGP (SEQ ID NO.72)

J1-65D_VH_1
MEWSWVFLFFLSVTTGVHSQVQLVQSGAELKKPGSSVKVSCKASGYTFTDYEMHWVRQAPGQGLEWMGAIQPGGGGTAYNQKFKGRVTLTADKSTSTAYMELSSLRSEDTAVYYCTRRGYDDYPFAYWGQGTLVTVSSASTKGP (SEQ ID NO.73)

J1-65D_VH_2
MEWSWVFLFFLSVTTGVHSQVQLVQSGAELKKPGSSVKVSCKASGYTFTDYEMHWVRQAPGQGLEWMGAIQPGGGGTAYAQKFKGRVTLTADKSTSTAYMELSSLRSEDTAVYYCTRRGYDDYPFAYWGQGTLVTVSSASTKGP (SEQ ID NO.74)

J1-65D_VH_3
MEWSWVFLFFLSVTTGVHSQVQLVQSGAEVKKPGSSVKVSCKASGYTFTDYEMHWVRQAPGQGLEWMGAIQPGGGGTAYAQKFQGRVTLTADKSTSTAYMELSSLRSEDTAVYYCTRRGYDDYPFAYWGQGTLVTVSSASTKGP (SEQ ID NO.75)

J1-65D_VH_4
MEWSWVFLFFLSVTTGVHSQVQLVQSGAEVKKPGSSVKVSCKASGYTFTDYEMHWVRQAPGQGLEWMGAIQPGGGGTAYAQKFQGRVTITADKSTSTAYMELSSLRSEDTAVYYCTRRGYDDYPFAYWGQGTLVTVSSASTKGP (SEQ ID NO.76)

Figure 24

ANTIBODIES THAT BIND TO JAGGED 1

RELATED APPLICATIONS

This application is a 35 U.S.C. §371 national stage filing of International Application No. PCT/GB2014/050104, filed on Jan. 15, 2014, which claims priority to British Patent Application No. 1300706.7, filed on Jan. 15, 2013. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Nov. 30, 2015, is named 126220-00101_SL.txt and is 59,394 bytes in size.

FIELD OF THE INVENTION

This invention relates to therapeutic antibodies that bind Jagged 1, pharmaceutical compositions comprising such antibodies, and uses of such antibodies in therapy.

BACKGROUND OF THE INVENTION

Cancer, in its various forms, is one of the leading causes of death in developed countries and the failure to effectively treat many patients affected by these diseases drives the continued search for new treatment strategies. Angiogenesis is a physiological process in which new blood vessels are grown from pre-existing vessels. It is a vital process in normal growth and development but also plays a key role in pathological conditions, such as cancer by providing the vasculature needed to supply the growing tumour with oxygen and nutrients. Angiogenesis is regulated by the complex interplay between many pathways, such as those controlled by VEGF and Notch. The clinical relevance of angiogenesis has firmly established this process as a rational target for cancer therapy [1, 2]

Targeting tumour angiogenesis with anti-VEGF antibodies has been a successful strategy, with bevacizumab becoming licensed for several tumour types, either as single agent or in combination therapy [3]. However many patients do not respond, or their response is temporary [1]. There has also been efforts to target other components of the VEGF pathway, including antibodies to VEGFR1, VEGFR2, neuropilin receptors and PLGF [4]. It is of note that the toxicity of the antibodies is far less than that of small molecule inhibitors targeting VEGFR, implying much greater specificity and fewer off target effects.

The Notch pathway has been implicated in vascular homeostasis and patterning and in pathological angiogenesis, prompting research into its modulation for a therapeutic benefit [5]. Notch signalling is mediated by membrane-bound receptors (Notch1-4) and ligands (Dll1, 3 and 4 and Jagged 1 and 2). Indeed, Notch1, Notch3, Notch4, Dll1, Dll4 and Jagged1 are expressed in cells of the vasculature and Notch1 [6], Dll1 [7] and Jagged 1 [8] knockout mice are embryonic lethal due to vascular defects, whilst Dll4 is haploinsufficient [9], thus suggesting that Notch signalling needs to be finely tuned to generate a fully functional vasculature. Indeed Notch pathway mutations are associated with human diseases exhibiting vascular defects, with NOTCH3 mutation in CADASIL [10] and JAGGED1 mutation in Alagille syndrome [11].

The binding of a Notch ligand, through its Delta/Serrate/Lag2 (DSL) domain, to the EGF11-12 region of a Notch receptor triggers proteolytic cleavage of the receptor and release of its intracellular domain (NICD). This processing requires the activity of two proteases, namely tumour necrosis factor α-converting enzyme (TACE) and presenilin/γ-secretase (a large protease complex made of presenilin1 or 2 as well as nicastrin, Pen-2 and Aph-1). The subsequent nuclear translocation of NICD results in transcriptional activation of genes of the Hes/E(spl) and Hey/Hesr families via the interaction of NICD with a member of the CSL (CBF1, Suppressor of hairless, and Lag-1) family of transcription factors also known as the recombination signal sequence-binding protein (RBP-Jk) and a transcriptional activator Mastermind-like protein (MAML). In turn, the Hes and Hey proteins, which are transcriptional repressors, inhibit the expression of genes that drive cells to adopt a differentiated fate [12].

In additional to playing a critical role in angiogenesis the Notch pathway is also implicated as an oncogenic pathway in tumour cells where it helps maintain stem cell populations, promotes cell survival, inhibits apoptosis and can drive cell proliferation (reviewed in [13]). Activating mutations in NOTCH1 have been identified in approximately 56% of T-cell acute lymphoblastic leukaemias (T-ALL) [14]; where they primarily act to induce either ligand-independent activation of the receptor or mutate the PEST domain and thus increase the stability of the Notch1 intracellular domain (NICD). Activating NOTCH1 mutations have also been identified in B-cell chronic lymphocytic leukaemia (B-CLL) [15, 16] and in mantle cell lymphoma [17] and these abnormalities have correlated with poor prognosis, suggesting that they define a distinct clinical subtype for therapeutic intervention. NOTCH2 mutations have been detected in 8% diffuse large B-cell lymphomas (DLBCL) and functionally demonstrated to be gain-of-function mutations [18]. Abnormal Notch signalling without the evidence of genetic lesions has also been reported in solid tumours, including breast, renal, pancreatic, prostate, cervical, endometrial, brain, intestinal, lung and skin cancers [19]. The pleiotrophic functions of Notch mean that this pathway can also have tumour suppressor roles in certain contexts (reviewed by [20, 21]). However, in the large majority of cases Notch signalling promotes tumour growth.

Thus Notch inhibition remains a promising new approach to cancer therapy and appears likely to be particularly useful in combination with other agents, including radiotherapy and chemotherapy [13]. Early studies of pan-Notch inhibition with γ-secretase inhibitors exhibited gastrointestinal toxicity; while prolonged treatment with anti-Dll4 antibodies led to the development of vascular/endothelial cell-based tumours similar to hemangioblastoma (reviewed by [13]). More recently antibodies that functionally inhibit individual Notch receptors have shown anti-tumour effects without gut toxicity [22, 23]. Further analysis using inducible gut specific gene targeting to study the role of individual Notch ligands demonstrated that Dll1 and Dll4-mediated Notch signalling was required for the homeostasis of intestinal stem cells, whereas deletion of Jagged 1 did not perturb the intestinal epithelium [24]. Thus targeting Jagged 1 activated signalling via multiple Notch receptors should be feasible without adverse effects on gastrointestinal toxicity.

Dll4 is highly expressed in the tumour vasculature and it influences tumour growth by regulating tumour angiogenesis in xenograft models [25-28] producing fewer but more functional vessels. Blocking Dll4 signalling, either by expression of soluble Dll4 or anti-Dll4 antibodies, decreased tumour growth even in tumours resistant to VEGF inhibition [25] confirming this pathway as a therapeutic target. Interestingly, Dll4 signalling induces expression of Jagged 1 [29]. This suggests that this latter Notch ligand may be a crucial downstream effector of Dll4-Notch signalling in tumour angiogenesis. In addition, excessive Notch signalling due to high expression levels of Jagged 1 and Notch receptors has been described in several cancers. For example, overexpression of Jagged 1 and Notch1 in breast cancer is associated with poor overall survival with a synergistic effect of high-level co-expression [30]. In addition, expression of Jagged 1 in squamous cell carcinoma cells induces angiogenesis and of the four receptors Notch1 is known to be critical for adult angiogenesis [31, 32]. Interestingly, Jagged 1-triggered Notch signalling from cancer cells to the endothelium was shown to induce angiogenesis, generating vessels which were smaller than those induced by Dll4.

Most blood vessels in the adult organism consist of at least two cell types, the endothelial cells (EC) and the mural cells (pericytes or the vascular smooth muscle cells (VSMC)). Pericytes wrap around the endothelium and play a crucial role in the stabilization and hemodynamic functions of the resulting blood vessels. In recent years, both cell types, EC and pericytes, have been targeted efficiently with the aim of oxygen starving solid tumours. Interestingly Notch signalling was shown to be crucial for the development of both these cell types [5].

Pericyte and vascular smooth muscle cell (VSMC) recruitment to newly forming vessels is a crucial step for vessel maturation and for endothelial cells to return to quiescence. A decade ago, pericytes were shown to stabilize immature blood vessels ending the plasticity period of vessel remodelling [33]. In addition, high vessel coverage by pericytes is critical to stabilise tumour vessels. Immature or poorly covered tumour vessels are extremely dependent on VEGF-A/VEGFR2 signalling and are therefore vulnerable to anti-VEGF therapies such as Bevacizumab. To date, however, the mechanisms underlying the survival of the remaining vasculature following anti-VEGF therapies are not fully understood. The remaining vessels appear to have greater pericyte coverage, suggesting that this cell type may limit the efficacy of these anti-angiogenic therapies [34, 35]. Interestingly, EC specific deletion of Jagged 1, which was recently shown to induce embryonic lethality and cardiovascular defects, was not due to impaired Notch1 signalling in EC or during arterial-venous differentiation. Instead deletion of Jagged 1 expression in EC was associated with poor vessel coverage by VSMC, which subsequently resulted in the developmental arrest of the mutant embryos [36]. Thus, based on its function as a regulator of vessel coverage, the Jagged 1/Notch signalling pathway presents itself as an attractive target that should have strong therapeutic benefit for the treatment of solid tumours, particularly when used in combination with anti-VEGF therapies. Therefore, antibodies aimed at blocking the Jagged 1-Notch signalling could have clinical benefit by targeting the tumour at three different levels, namely endothelial cells, mural cells and tumour cells.

Regulatory T cells (Tregs) infiltrate tumours in a vast array of tumour types. Their numbers are often clinically relevant and Tregs have a diversity of roles including their ability to suppress anti-tumour immunity and promote angiogenesis (recently reviewed by [80, 81]). Overexpression of J1 by antigen-presenting cells can induce human antigen-specific Tregs and modify the immune response to viral antigens [82]. Notch ligands, such as J1, are also expressed on Tregs and blockade of Notch signalling, using antibodies targeting J1 or N1 inhibited Treg suppressor function [83]. Furthermore, pre-exposure of CD4+CD25− effector T cells to J1 significantly increased their sensitivity to Treg-mediated suppression [84]. Thus, targeting J1 on immunoregulatory cell populations in the tumour microenvironment also offers the opportunity to improve the host immune response to tumour antigens.

There is new evidence suggesting that Jagged 1 may also be a ligand for a receptor other than the Notch family. CD46 (MCP) is a ubiquitously expressed human type I transmembrane glycoprotein that was originally discovered as a complement regulatory protein and then a cell-entry receptor enabling viral infection. Interestingly viral targeting of tumours using their elevated CD46 expression as a tumour selective entry receptor has been used as a strategy to facilitate therapy and imaging in multiple cancer types [37]. Anti-cancer applications include direct targeting of cancer cells by virally induced cytopathic effects and syncytial formation [38], including breast cancer [39], medulloblastoma [40], glioma [41] and recurrent ovarian cancer [42]; gene therapy targeting in lung adenocarcinomas [43]; and radiovirotherapy of prostate cancer [44]. More recently an immunomodulatory role in the co-stimulation of interferon-γ secreting effector human T helper type 1 ($T_H1$) cells and their subsequent switch into IL-10-producing regulatory T cells has been identified (reviewed in [45]).

There is a considerable literature regarding the complement system and cancer as reviewed recently [46, 47]. Most tumours express either soluble regulators or membrane bound complement receptors (CD35, CD46, CD55 and CD59) on the cell surface, thus suppressing activation of the complement system and diminishing its role in tumour clearance. It is well established that overexpression of CD46, CD55 and CD59 on tumours protects them from direct complement lysis. Furthermore, therapeutic antibodies (such as rituximab) use complement dependent cytotoxicity (CDC) to kill tumour cells and this activity can be increased by targeting membrane bound complement receptors e.g. using blocking antibodies.

CD46 upregulation in tumours has been widely reported and examples include upregulated expression in 77% of bladder cancers [48] and high expression in head and neck squamous cell carcinoma [49]. CD46 expression was more abundant on primary multiple myeloma cells than normal hematopoietic cells of various lineages in the bone marrow [50]. RNAi mediated knockdown of CD46 significantly inhibited the growth of pancreatic cancer cells overexpressing CD46 [51]. While breast cancers with CD46 expression have a less favourable prognosis [52] as did CD46+ ovarian cancer patients [53]. Downregulation of CD46 in MCF7 and MDA-MB-231 breast cancer cell lines via microRNAs induced opsonization of cancer cells via an alternative pathway resulting in complement activation [54]. RNAi targeting of CD46 in Du145 (prostate), BT474 (breast) and K562 (erythroleukaemia) cells also significantly increased C3 opsonization[55]. While shRNA targeting of CD46 and DAF enhanced complement mediated lysis in cervical cancer cells [56] and anti-sense phophorothioate oligonucleotides to down regulate CD55 and CD46 sensitized tumour cells to complement attack [57].

Some biological activities of CD46 cannot be explained by its interaction with the known ligands, for example C3b, and thus there has been speculation that another ligand existed for this receptor. In a recent study, activation of CD46 on CD4+ T cells was shown to regulate the expression of Notch and its ligands and furthermore Jagged 1 was identified as an additional physiological ligand for CD46 [45]. Further evidence of the importance of this interaction was that patients with mutations in genes encoding CD46 or Jagged 1 shared key biological features, including recurrent infections. While T-cell proliferation and effector function of $T_H2$ cells was unaffected in these patients, the in vitro induction (or regulation) of $T_H1$ cells was seriously compromised or absent and seemed to involve altered responsiveness to cytokines of the IL-2 family. The most significant cell surface receptor phenotype was deregulation of components of the IL-7 receptor, CD127 and CD132, which is required for T-cell homeostasis and enhancement of $T_H1$ and $T_H17$ responses. CD127 is also known to be a strong risk locus for multiple sclerosis, independently of the major histocompatibility complex.

The Jagged 1 binding site was localised to the CCP1 and CCP2 domains of CD46, these are the domains commonly bound by viral ligands such as adenovirus knob proteins or measles virus hemagglutinin. This Jagged 1 binding was mediated by a recombinant Jagged 1 DSL-EGF3 fragment comprising the DSL domain and the first three EGF-like domains demonstrating that the CD46– and Notch 1 binding sites in Jagged 1 are localised in the same region of the protein. Surface plasmon resonance experiments to measure the binding affinity of Jagged 1 interactions suggested that CD46 exhibited a tighter interaction with Jagged 1 than a soluble Notch 1 (EGF11-13) fusion protein. This was consistent with data suggesting that the presence of CD46 on T-cell surfaces restricts the interactions of Notch 1 and Jagged 1. Thus there is important cross-talk between the complement and Notch systems that is required for effector T-cell function and which may have a key role in other biological processes, particularly cancer.

Anti-Jagged 1 antibodies targeting the DSL domain and/or first three EGF repeats may thus also block the interaction between CD46 and Jagged 1. While some therapeutic effects may be mediated via the Notch system these reagents may also target additional pathways involving CD46.

The extracellular domain of Jagged 1 possesses shared structural features with all Notch ligands, these being the presence of a Delta/Serrate/Lag-2 (DSL) domain and a variable number of epidermal growth factor-like (EGF) domains. Crystallographic studies of the functional fragment of human Jagged 1 (DSL-EGF1-3) in combination with structure-informed mutagenesis, revealed residues 199-207 of the DSL domain to have a critical role in Notch binding (Cordle et al., 2008 [65], incorporated herein by reference). The same study mapped the predominant site of interaction on Notch 1 to the EGF12 domain.

US 2008/0317760 discloses a series of monoclonal antibodies raised in mice against residues 24-1060 of human Jagged 1, with epitopes mapping to the EGF1 domain. One antibody was identified as being capable of inhibiting Jagged 1-Notch1 association, and reducing tumour growth in a murine xenograft model. It is therefore apparent that, in the context of antibody-based therapy, targeting the DSL domain of human Jagged 1 is not essential for the inhibition of binding to endogenous receptors, such as Notch, and thus downregulated Jagged 1-mediated signalling.

WO 2011/063237 discloses further anti-Jagged 1 monoclonal antibodies, in this instance generated by the immunisation of mice with residues 1-1060 of mouse Jagged 1 and the identification of human Jagged 1 extracellular domain-recognising $F_{ab}$ fragments from a synthetic library using phage display. These were found to bind both human and mouse Jagged 1 with similar affinity, with all but one also recognising human Jagged 2. Several antibodies furthermore prevented human Jagged 1 binding to human Notch 2, inhibited Jagged-mediated signalling and reduced tumour growth in murine xenograft models. However, the epitopes recognised by the antibodies disclosed in WO 2011/063237 were not mapped to a distinct region or domain within the Jagged 1 protein.

In light of the prior art, there is a rationale for the provision of a therapeutic anti-Jagged 1 monoclonal antibody which recognises a defined epitope on human Jagged 1, moreover one that is distinct from the EGF domains, and which inhibits Jagged 1-mediated signalling and tumour growth with suitable efficacy for use in therapy. Given the well-documented occurrence of acquired resistance to cancer therapeutics due to single residue mutations, for example cases of imatinib-resistant chronic myeloid leukaemia [85], the provision of a therapeutic antibody with a defined epitope which is known to differ from that recognised by a pre-existing antibody against the same target, is of therapeutic value in the context of combination therapy. Furthermore, cross-reactivity of monoclonal antibodies between the EGF domains of different proteins has been previously reported, for example in the case of CD97 and EMR2 [86].

Accordingly, there is a need for additional antibodies capable of inhibiting the interaction between human Jagged 1 and Notch/CD46 through binding to a defined epitope on Jagged 1, preferably one which is distinct from the EGF domains.

SUMMARY OF THE INVENTION

The present invention is based on the identification and molecular characterisation of antibodies which bind to the Delta/Serrate/LAG-2 (DSL) domain of human Jagged 1 (also referred to as Jag1 or J1) via novel epitopes. Said antibodies effectively block human Jagged 1-receptor interactions and inhibit in vitro Jagged 1-mediated signalling in tumour cell lines, thus indicating their suitability for use in cancer therapy.

Cordle et al (2008) identified residues 199-207 of the human Jagged 1 DSL domain to have a critical role in Notch receptor binding [65]. The present inventors were therefore surprised to generate a number of antibodies with the above desirable properties, which all recognise epitopes that can only be commonly defined as comprising the DSL domain residue E228.

According to a first aspect of the invention, the present invention provides an antibody which specifically recognises an epitope comprising a portion of the Delta/Serrate/LAG-2 consensus sequence (DSL) domain of human Jagged 1 and blocks the interaction between human Jagged 1 and any receptor selected from the group consisting of the Notch family and CD46; wherein said portion of the DSL domain of human Jagged 1 comprises the residue E228.

According to a second aspect of the invention, the present invention provides a pharmaceutical composition comprising an antibody as defined above, together with a pharmaceutically acceptable diluent, excipient, adjuvant and/or at least one additional therapeutic agent.

According to a third aspect of the invention, the present invention provides the use of an antibody or pharmaceutical composition, as defined above, in therapy.

According to a fourth aspect of the invention, the present invention provides a hybridoma comprising and/or secreting an antibody as defined above.

According to a fifth aspect of the invention, the present invention provides a cell or cell line expressing an antibody as defined above in recombinant form.

According to a sixth aspect of the invention, there is an expression vector, capable of expressing an antibody of the invention.

BRIEF DESCRIPTION OF THE FIGURES

The invention is described with reference to the accompanying drawings, wherein:

FIG. 23. Shows the CDR domain amino acid sequences for the wildtype J1-183D antibody together with variant CDR sequences (SEQ ID NOS 13-15, 13-15, 13, 31, 15, 13, 32, 15, 13, 33, 15, 16-18, 16-18, 16, 34, 18, 16, 34, 18, 16, 34, and 18, respectively, in order of appearance) used to construct a plurality of variant antibodies. Grey highlighting indicates amino acid sequence differences from the wildtype. Also shown are the complete individual $V_L$ and $V_H$ wildtype and variant sequences which were used in the construction of the variant antibodies.

FIG. 24. Shows the CDR domain amino acid sequences for the wildtype J1-65D antibody together with variant CDR sequences (SEQ ID NOS 1-3, 1, 26, 3, 1, 27, 3, 1, 27, 3, 25, 27, 28, 4-6, 4-6, 4, 29, 6, 4, 30, 6, 4, 30, and 6, respectively, in order of appearance) used to construct a plurality of variant antibodies. Grey highlighting indicates amino acid sequence differences from the wildtype. Also shown are the complete individual $V_L$ and $V_H$ wildtype and variant sequences which were used in the construction of the variant antibodies.

DETAILED DESCRIPTION OF THE INVENTION

The present invention provides antibodies which bind to the Delta/Serrate/LAG-2 consensus sequence (DSL) domain of human Jagged 1 (also referred to as Jag1 or J1) via novel epitopes. Said antibodies effectively block human Jagged 1-Notch receptor interactions, inhibit in vitro Jagged 1-mediated signalling in tumour cell lines and human Jagged 1 dependent tumour growth in vivo, thus indicating their suitability for use in cancer therapy.

Cordle et al (2008) identified residues 199-207 of the human Jagged 1 DSL domain to have a critical role in Notch receptor binding [65]. The present inventors were therefore surprised to generate a number of antibodies with the above desirable properties, which all recognise epitopes that can only be commonly defined as comprising the DSL domain residue E228.

Accordingly, the antibodies of the present invention all recognise epitopes which have been defined. Such characterisation is desirable in the context of cancer therapy, notably combination therapy, whereby acquired resistance to a drug or therapeutic antibody may occur as a result of the mutation of one or more residues in the target protein. Thus it is desirable to be aware of the binding site of a therapeutic antibody when selecting one or more suitable complementary therapies in order to anticipate and/or respond to acquired resistance in malignant cells.

The present inventors generated monoclonal antibodies targeting the DSL domain of human Jagged 1 by the immunisation of mice with a limited extracellular fragment of human Jagged 1 (residues 185-335—DSL+EGF1-3). Spleen cells taken from the immunised mice were then fused with a myeloma fusion partner cell line, tested for reactivity with the antigen and then cloned by single cell dilution in order to generate a hybridoma cell line secreting a homogenous population of monoclonal antibodies. Hybridoma culture supernatants containing the antibodies were then screened by ELISA and FACS for binding to the DSL domain and blocking of the Jagged 1-Notch 1 interaction, identifying four with the desired characteristics (denoted J1-65D, J1-156A, J1-183D and J1-187B).

Figure 1:
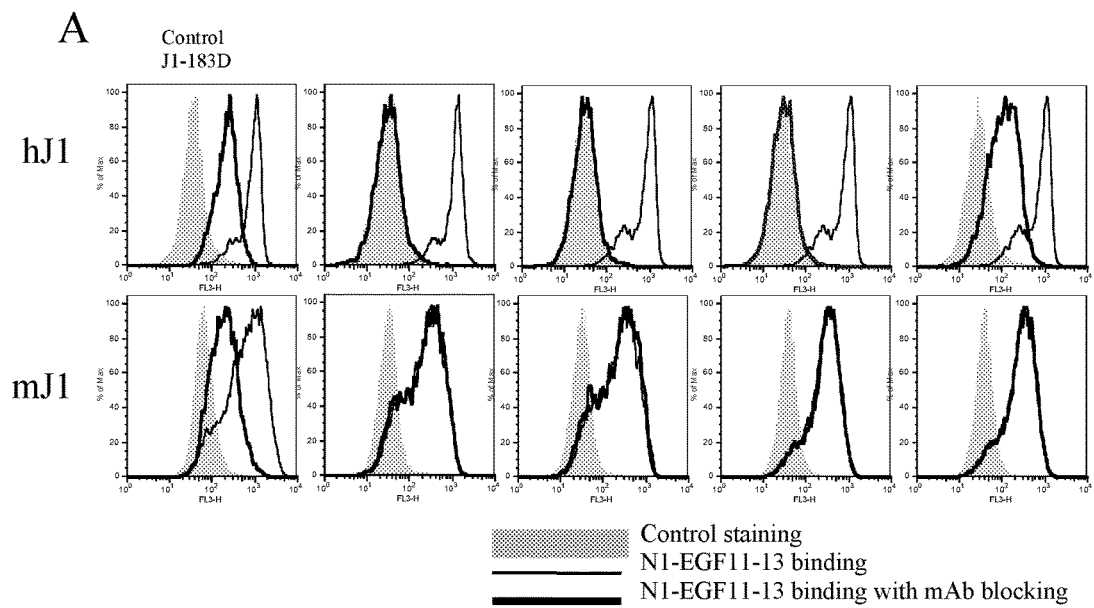
FIG. 1. Shows blocking of Notch 1 (N1) binding to Jagged 1 (J1) expressing cells (A) and blocking of CD46 binding to J1 recombinant protein (B) by J1 monoclonal antibodies (mAbs). (A) The 21 hybridoma supernatants that recognised cell surface J1 were screened by flow cytometry for their ability to block the interaction between cell expressed full length human J1 (hJ1; HEK293 transfectants) or murine J1 (mJ1; B16F10 transfectants) and biotinylated N1-EGF11-13 soluble recombinant protein bound to avidin-coated beads (thin line indicates binding). No binding was observed with a control protein cbEGF12-14 from human fibrillin1 (grey shading). Four antibodies either fully (J1-65D, J1-156A, J1-183D) or partially (J1-187B) blocked binding of human N1 to human J1, seen when thick line fully overlaps with the grey shading or moves away from the thin line and towards the grey shading. The antibody denoted J1-142B is not an antibody according to the present invention, but demonstrates partial blocking of mJ1-N1 binding as a positive control. (B) ELISA assay of the interaction of immobilised CD46 (CCP1-CCP3) with biotinylated J1 DSL-EGF3 (solid black bar) and in the presence of FACS positive hybridoma supernatants (solid grey bars). Control assays (far left and right), represented by diagonal shading, contain CD46 or biotinylated J1 DSL-EGF3 alone. The Notch 1/Jagged 1 blocking mAbs, J1-65D, J1-156A, J1-183D and J1-187B are indicated by asterisks. In this ELISA assay, variable inhibitory effects of the blocking antibodies were observed. However, cell-based assays with the natively expressed full-length Jagged 1 are required to verify their effects on the J1/CD46 interaction.
Figure 1:
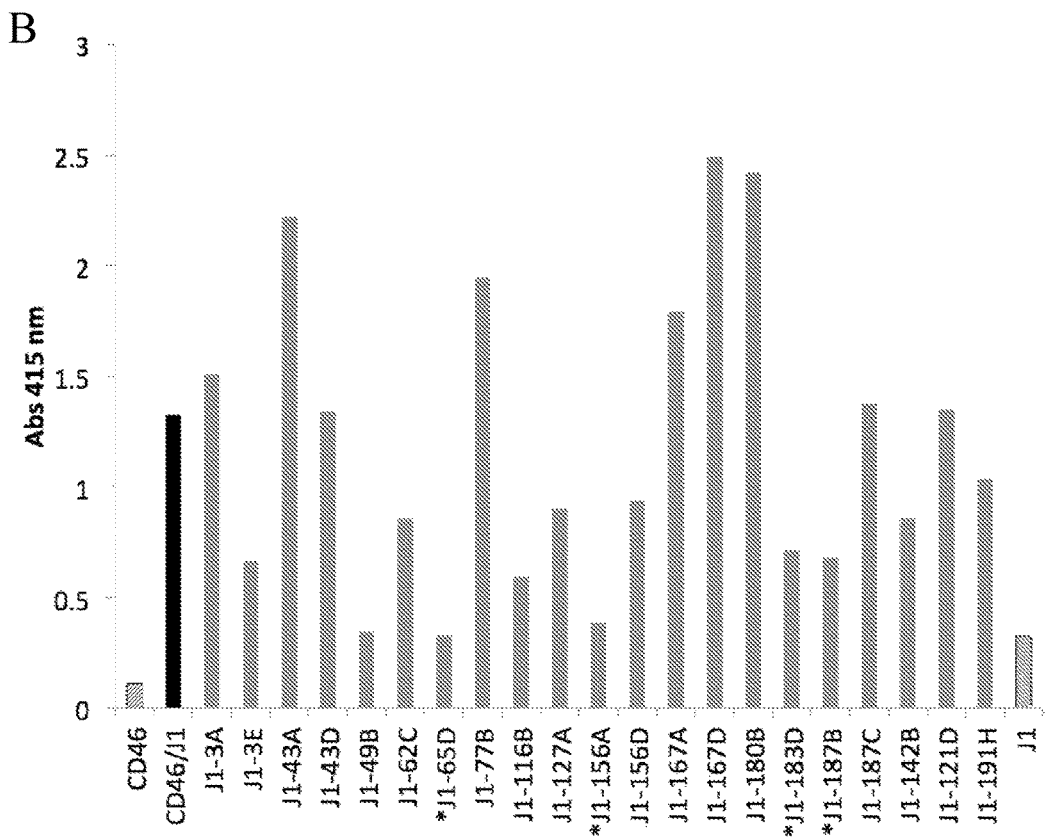
Figure 2:
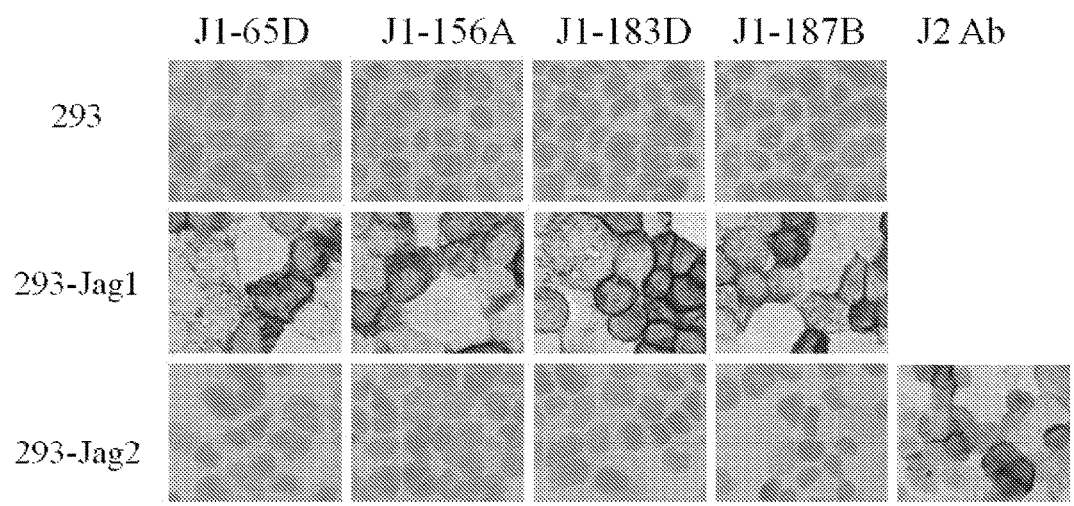
FIG. 2. Shows immunocytochemical staining of J1 and J2 transfectants with J1 mAbs. Cytospin preparations of HEK293 cells transfected with an empty vector (293) or plasmids encoding full length human J1 or Jagged 2 (J2) were immunolabelled with hybridoma supernatants containing the J1 mAbs. A commercial antibody against J2 was used as a positive control to confirm transfection and expression of recombinant J2 (bottom right). None of the J1 mAbs exhibited cross-reactivity with J2 by immunoperoxidase labelling.
Figure 3:
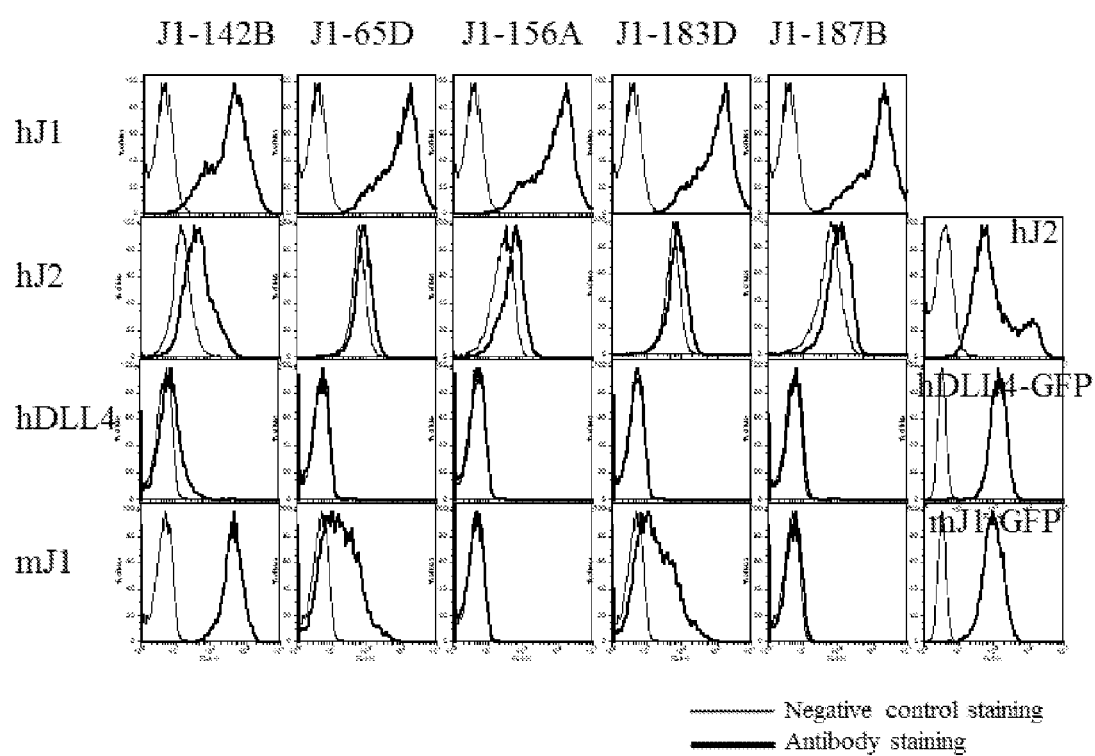
FIG. 3. Shows FACS analysis of the Notch ligand specificity of the J1 mAbs. HEK293 cells transfected with human J1 or J2 and B16F10 cells transfected with human DLL4 (hDLL4) or mJ1 were FACS stained with J1 mAbs (10 µg/ml) followed by an anti-mouse-APC secondary Ab. All the antibodies stained human J1, while only weak species cross reactivity against mJ1 was observed with J1-65D and J1-183D. No significant binding was observed to hDLL4 while weak binding was observed to J2 by J1-156A and J1-187B. J2 expression on the cell surface was confirmed using a commercial antibody; expression of hDLL4 and mJ1 was confirmed by detection of GFP co-expression. The antibody denoted J1-142B is not an antibody according to the present invention, but acts as a positive control demonstrating the presence of cell surface mJ1 on B16F10 transfectants.
Figure 7:
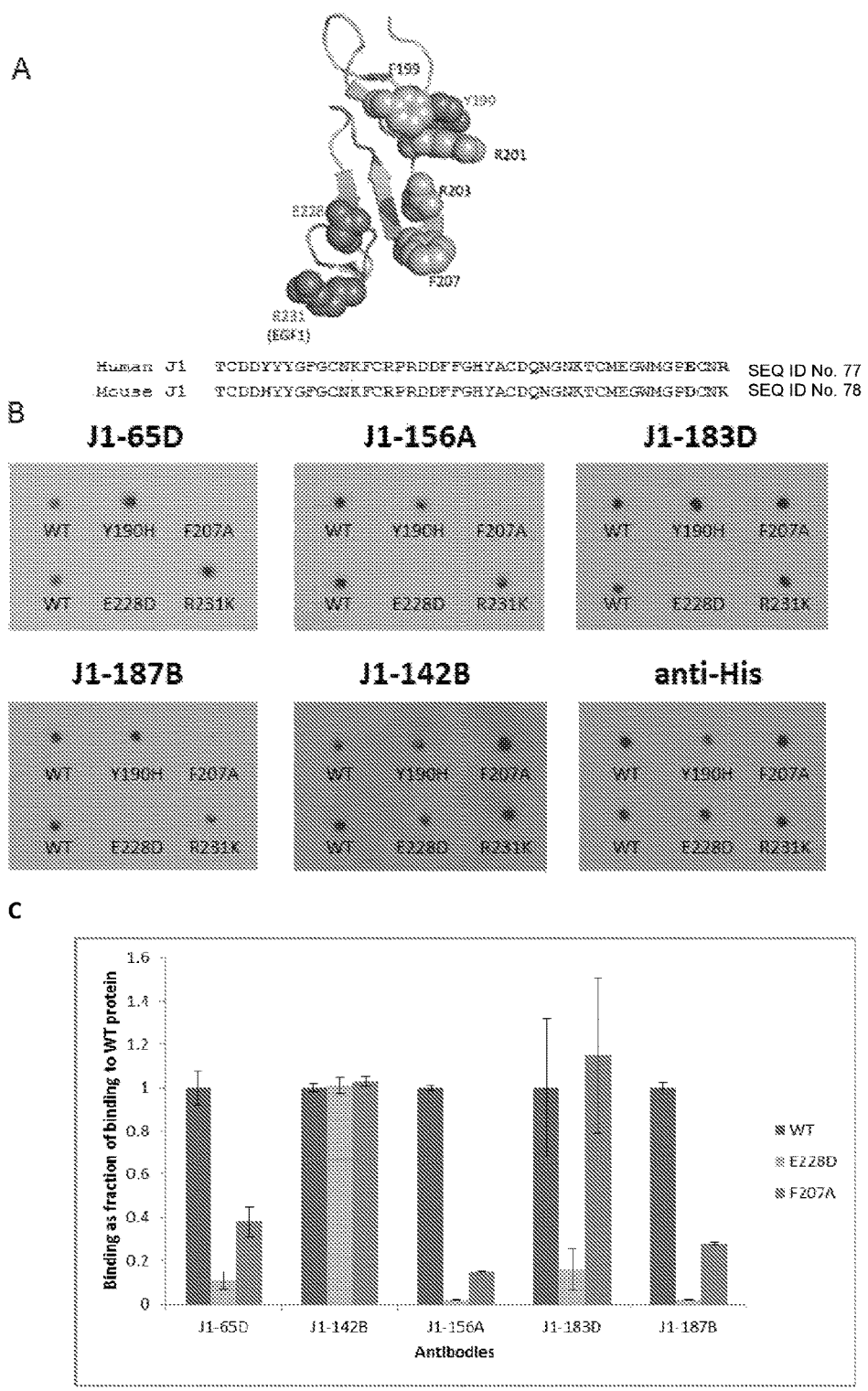
FIG. 7. Shows epitope mapping to identify the molecular basis for preferential human J1 binding. (A) Residues in human J1 DSL domain and first residue of EGF1 domain that are substituted in mouse J1. Note the proximity of these residues (Y190, E228 from the DSL domain and R231 from the EGF1 domain) to the residues shown to be important for binding to Notch (F199, R201, R203, R207). (B) Dot blot mapping J1 mAb epitopes. Amino acids 190 and 228 have different amino acid identities within the human and murine J1 DSL domains. The human amino acids at positions, 190, 228 and 231 were each mutated to the murine sequence. These soluble DSL-EGF3 recombinant proteins were used in dot blots to identify the amino acids responsible for preferential mAb binding to the human protein. Purified mAbs J1-65D, J1-156A, J1-183D and J1-187B were used at a concentration of 0.02 µg/ml to detect 10 ng mutant protein. Hybridoma supernatant of J1-142B (1:250) was used to detect 0.2 µg protein. Blotting with anti-His (Qiagen RGS-His conjugate at 1:10,000) was used to confirm equivalent amounts of protein were loaded. All four J1 DSL domain targeting antibodies of the invention lacked J1 binding when the human glutamic acid residue at amino acid 228 was converted to the murine aspartic acid residue. The antibody denoted J1-142B, which is not an antibody according to the present invention, demonstrates recognition of this mutant construct by an antibody which specifically recognises murine J1. (c) Antibodies were coupled to the dextran matrix of a CM5 Biacore chip using primary amine coupling and Jagged 1 DSL-EGF3 proteins at 100 nM flown over. All binding is reported as a fraction of the binding of the WT Jagged 1 DSL-EGF3 construct to that antibody. Values reported are mean+/−the standard deviation calculated from five independent injections. WT=wild type unmutated Jagged1.
Figure 9:
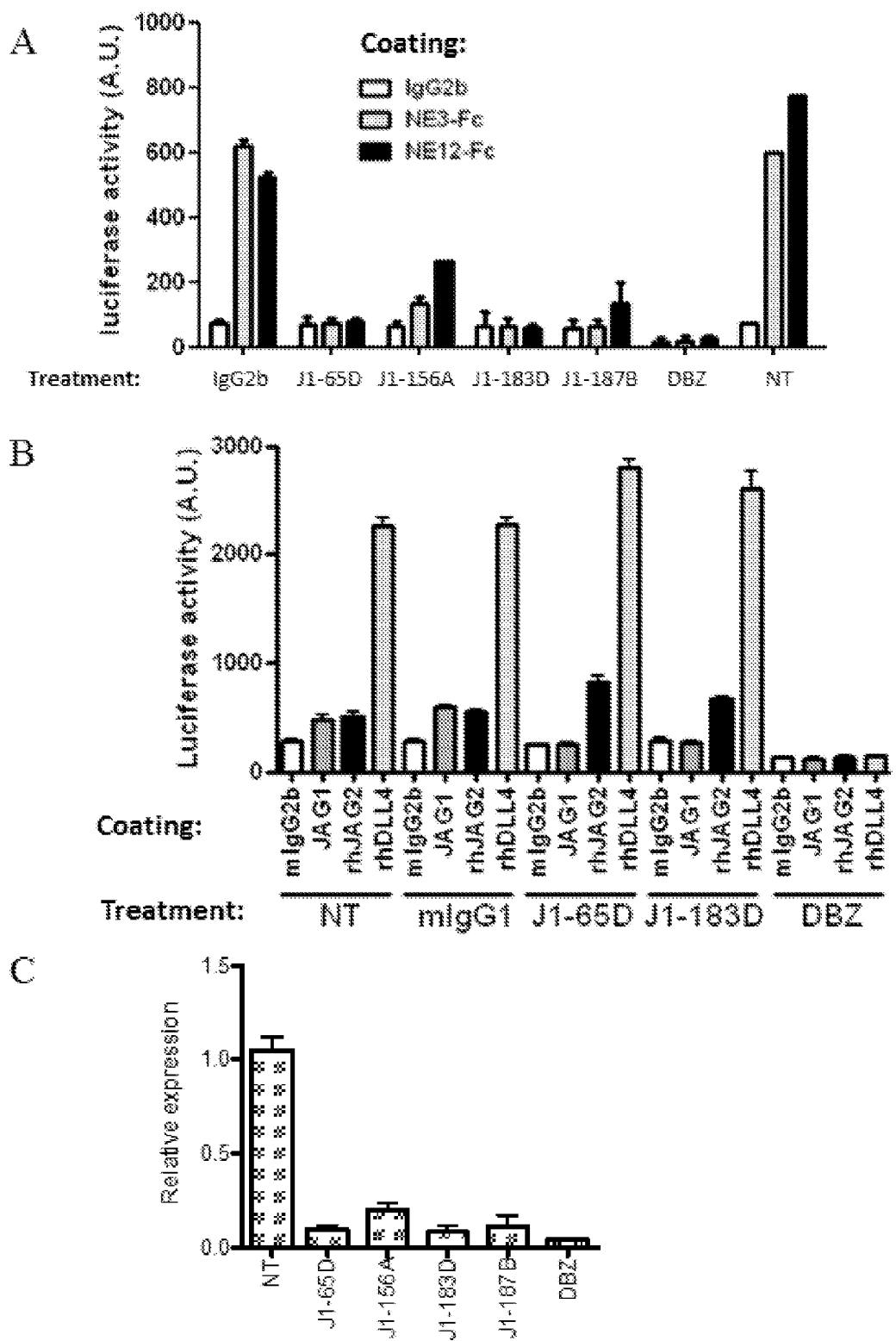
FIG. 9. Shows J1 blocking mAbs repressing endogenous Notch signalling. (A) The colorectal cancer cell line LS174T expressing luciferase under the control of Notch co-factor RBPJ was stimulated with mammalian cell-expressed soluble J1 proteins (NE3-Fc and NE12-Fc) or a control protein in the presence of J1 mAbs (10 µg/ml), and luciferase activity was measured. (B) The same cell line as in (A) was stimulated with different recombinant human Notch ligands: J1 (NE12-Fc), J2, DLL4 or a control protein (mIgG2b) in the presence of J1 mAbs (J1-65D and J1-183D) and luciferase activity was measured proving mAb ligand specificity as no inhibition was observed for J2 and DLL4 stimulations. (C) Breast cancer MDA-MB-231 cells were cultured with J1 mAbs. The expression level of the Notch target gene HES1 was measured by qPCR using $\beta 2m$ as the control gene. In all experiments the γ-secretase inhibitor DBZ was used as a positive control for pan Notch inhibition and a control mAb (IgG2b or IgG1) or no treatment (NT) were negative controls.
Figure 10:
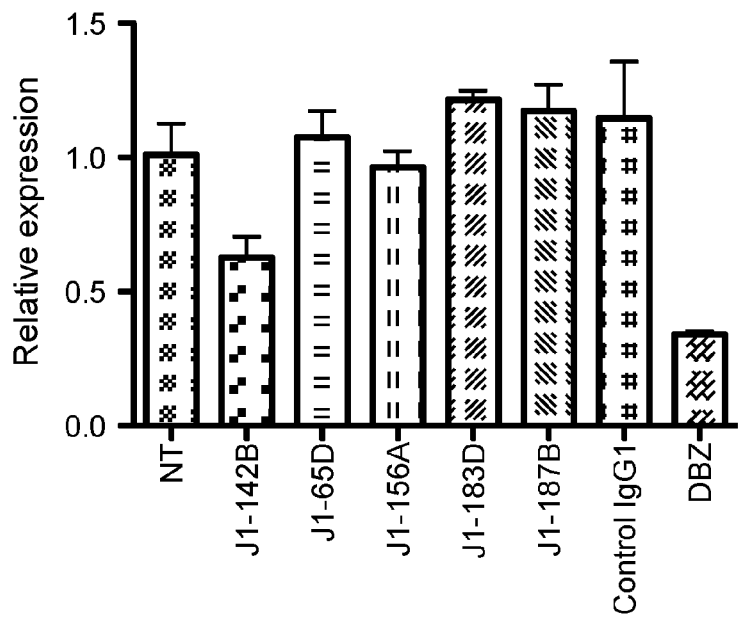
FIG. 10. Shows the effects of J1 mAb treatment on endogenous murine and recombinant rat Jagged1 ligand stimulated Notch signalling. (A) Mouse melanoma B16F10 cells stably expressing murine J1 were cultured with 10 µg/ml of each J1 mAb, or an IgG1 control antibody, for 7 days with fresh mAb supplemented every 2 days. The γ-secretase inhibitor DBZ (100 nM) was used as a control for Notch inhibition. Cells were harvested, total RNA extracted and cDNA was synthesised. Murine Hes1 expression levels were detected by real-time PCR normalised against GAPDH. The antibody denoted J1-142B is not an antibody according to the present invention, but acts as a positive control demonstrating the effect of an antibody which specifically recognises mJ1 and partially blocks mJ1-mN1 association, on murine Hes1 expression. (B) Human breast cancer (MDA-MB-231) and primary endothelial cells (HUVEC) were cultured over plates coated with recombinant rat Jagged1 (rrJag1-Fc) or a control protein (mIgG1) in the presence of 10 µg/ml of J1 mAbs or isotype control Ab. 24 hours later cells were harvested, total RNA extracted and cDNA was synthesised. Expression of the human Notch-target genes HES1 and HEY2 was analysed by real-time PCR and $\beta$2-microglobulin was used as control gene. Results from one representative experiment are shown.
Figure 10:
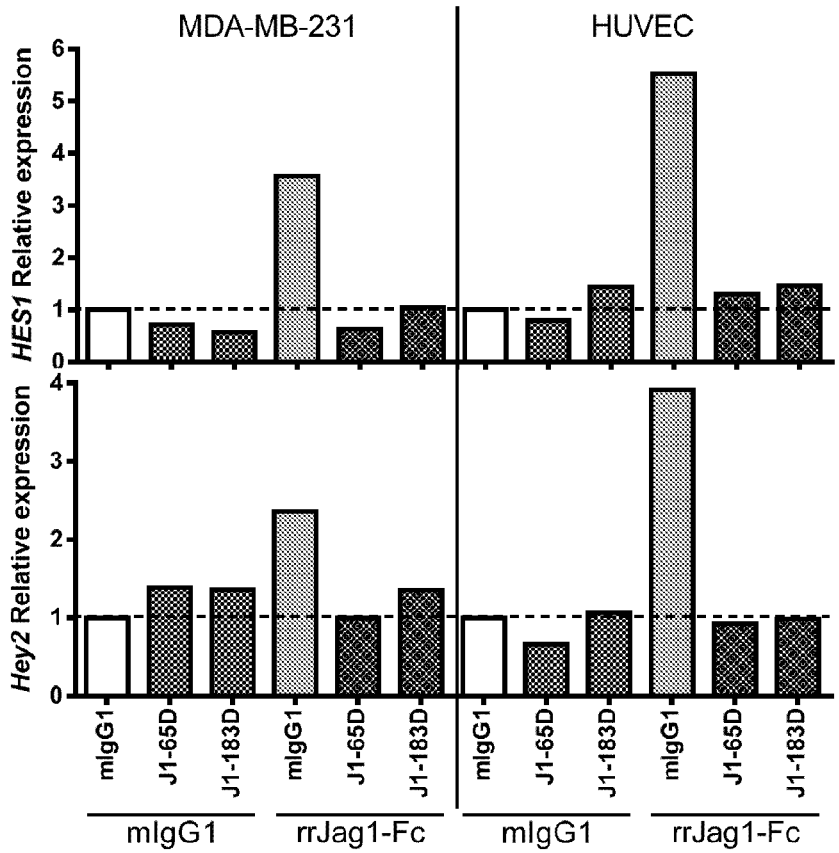
Figure 11:
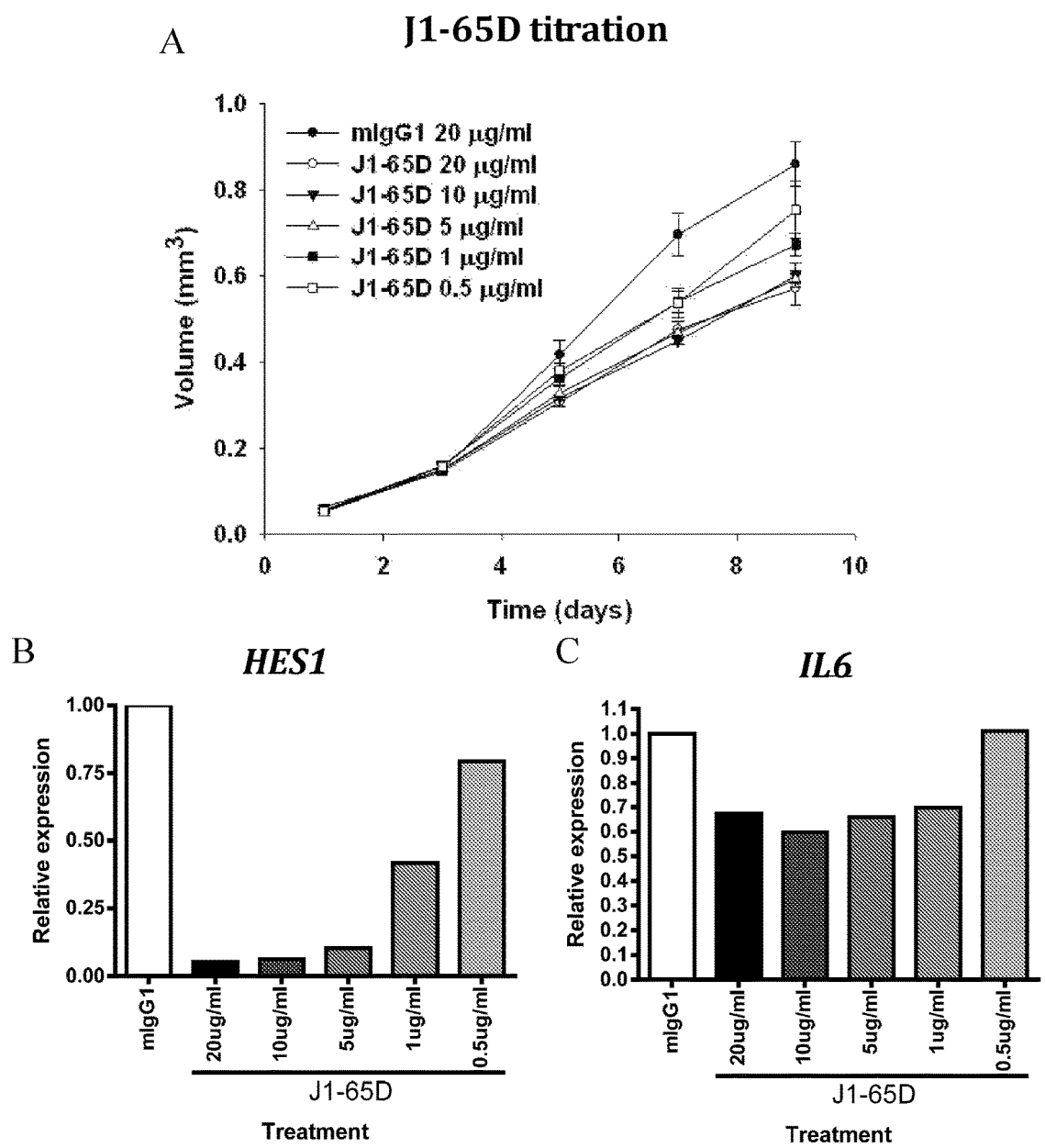
FIG. 11. Shows effects of antibody titration on MDA-MB-231 3-D growth. MDA-MB-231 breast cancer cells were grown as spheroids in the presence or absence of different concentrations of J1-65D (anti-Jagged 1 mAb) or a mIgG1: control mAb. (A) Growth curve of treated tumour cell spheroids. Size quantification was performed by image analysis. (B) HES1 Notch-target gene expression was analysed by qPCR as a readout of pathway inhibition. (C) qPCR analysis addressing treatment effect on the expression of the pro-tumorigenic cytokine IL6.
Figure 12:
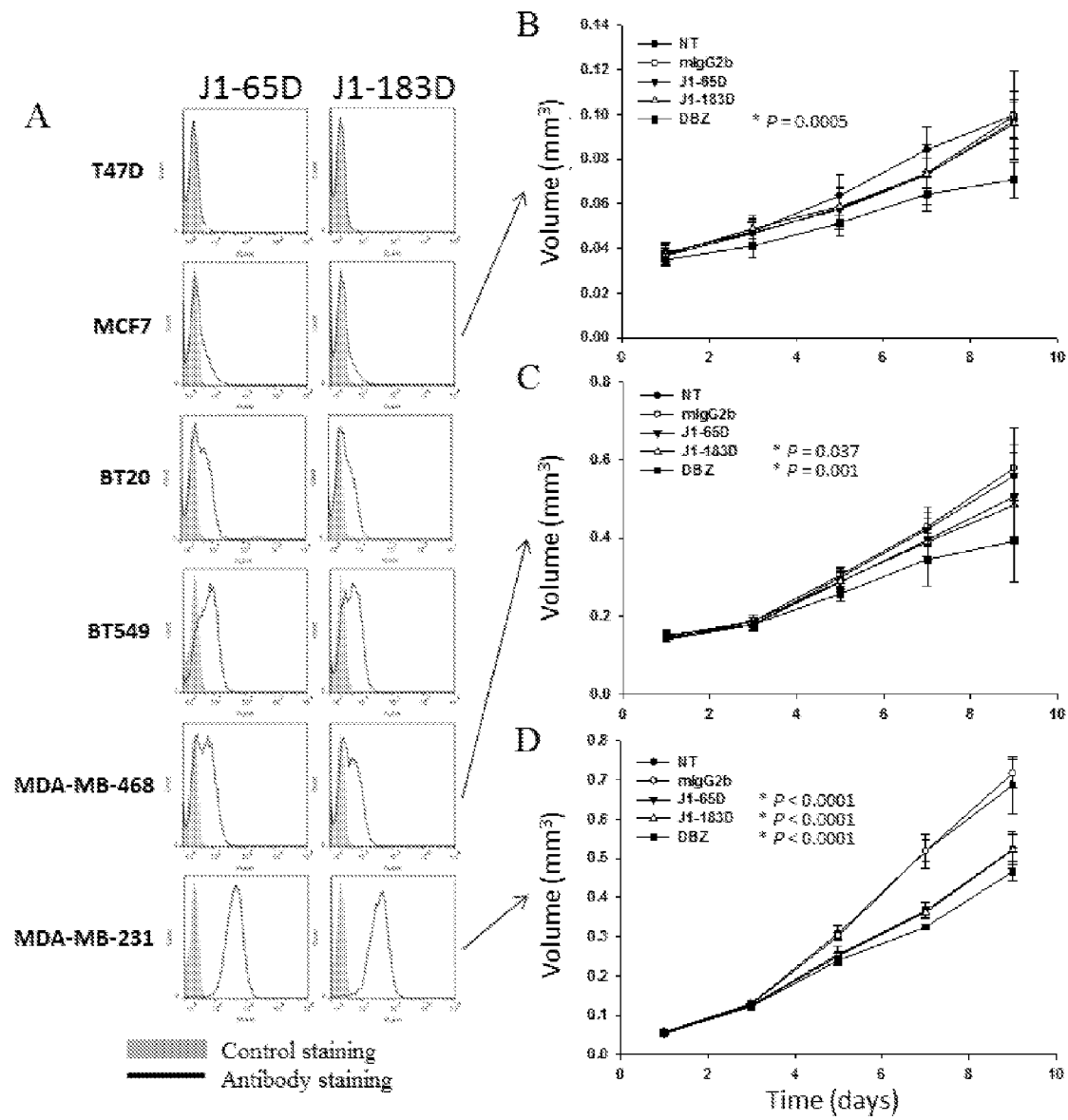
FIG. 12. Shows J1 expression in breast cancer cell lines and effects of J1 antibody treatment on 3-D spheroid growth. (A) J1 cell surface protein expression in a panel of breast cancer cell lines. FACS analysis was performed on six different cell lines using two J1 specific mAb, demonstrating great variability in J1 expression levels, from really high (MDA-MB-231) to negative (T47D). Secondary antibody only staining was used as a negative control. Cell lines representative of the different J1 levels were then grown in 3-D culture as spheroids and treated with anti-J1 mAbs (J1-65D and J1-183D; DBZ: γ-secretase inhibitor, positive control of Notch inhibition; mIgG2b: control mAb; NT: no treatment). One of at least 2 independent experiments is shown. (B) Treatment of MCF7 cells (almost negative for J1) did not show any significant effect on treatment with anti-J1 mAbs. (C) Treatment of MDA-MB-468 cells (low J1 levels) showed significant growth reduction on treatment with one of the anti-J1 mAbs (J1-183D) albeit much milder than DBZ treatment. (D) Treatment of the highly J1 expressing cell line MDA-MB-231 showed significant growth reduction as strong as with DBZ treatment with both mAbs (J1-65D and J1-183D).
Figure 13:
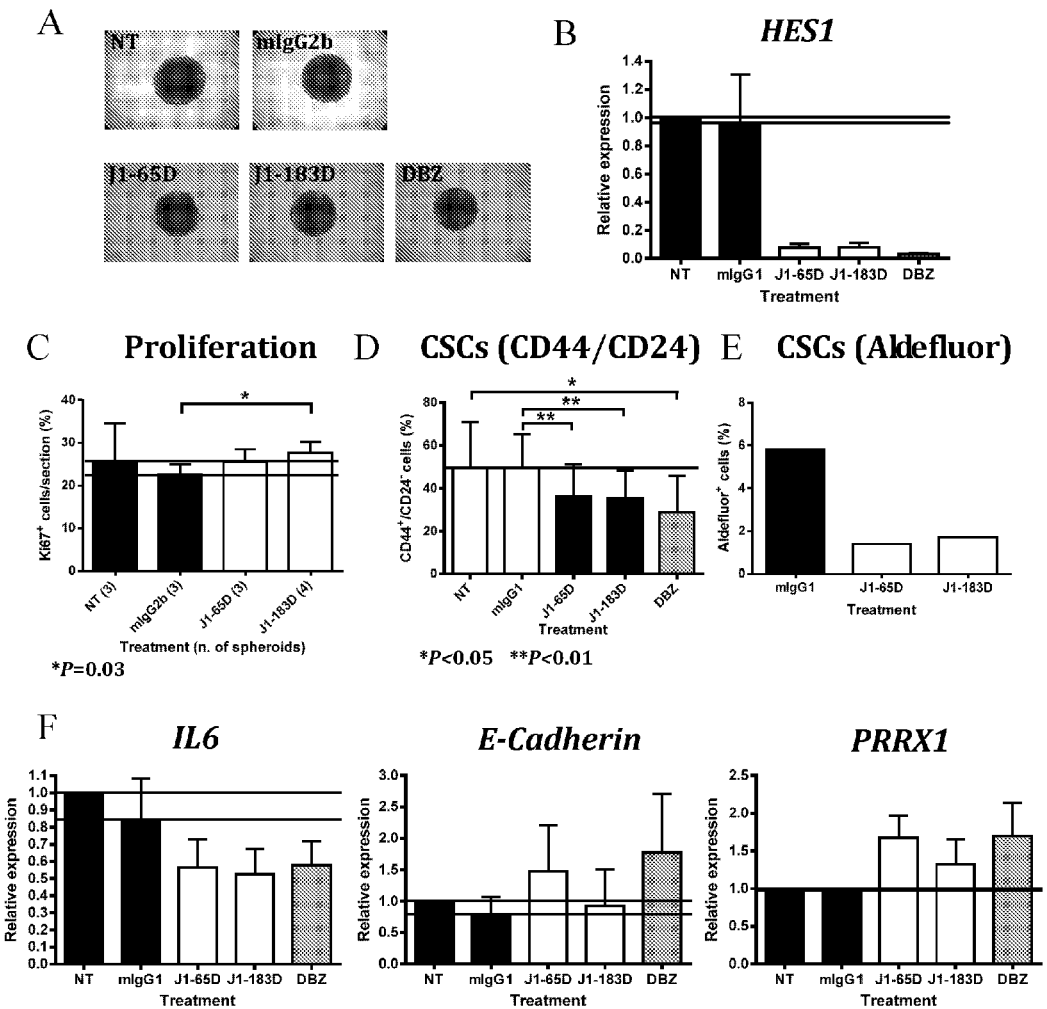
FIG. 13. Shows the analysis of MDA-MB-231 3-D growth inhibition in response to J1 mAb treatment. MDA-MB-231 breast cancer cells were grown as spheroids in the presence (10 mg/ml J1-65D or J1-183D: anti-Jagged1 mAbs; DBZ: γ-secretase inhibitor; mIgG2b or mIgG1: control mAb) or absence of treatment (NT: no treatment). (A) Representative images of spheroids at day 9 of treatment. (B) HES1 Notch-target gene expression was analysed by qPCR as a readout of pathway inhibition. (C) Proliferation, % Ki67$^+$ cells was evaluated by IHC on 3-5 spheroids/treatment from a single experiment. Quantification was performed by image analysis. Bars represent average of positive cell number (%) ±SD from multiple spheroids in a single experiment. (D) FACS analysis of the cancer stem cell (CSCs) enriched subpopulation CD44+/CD24− (%) in treated spheroids. Bars represent average of 3 independent experiments ±SD. (E) ALDEFLUOR™ staining of treated spheroids to quantify the population of breast cancer stem cells expressing aldehyde dehydrogenase (one representative experiment). (F) qPCR analysis addressing treatment effect on the gene expression of the pro-tumourigenic cytokine IL6 and the EMT related genes E-cadherin and PRRX1. Bars represent the average of 2 independent experiments ±SD.
Figure 18:
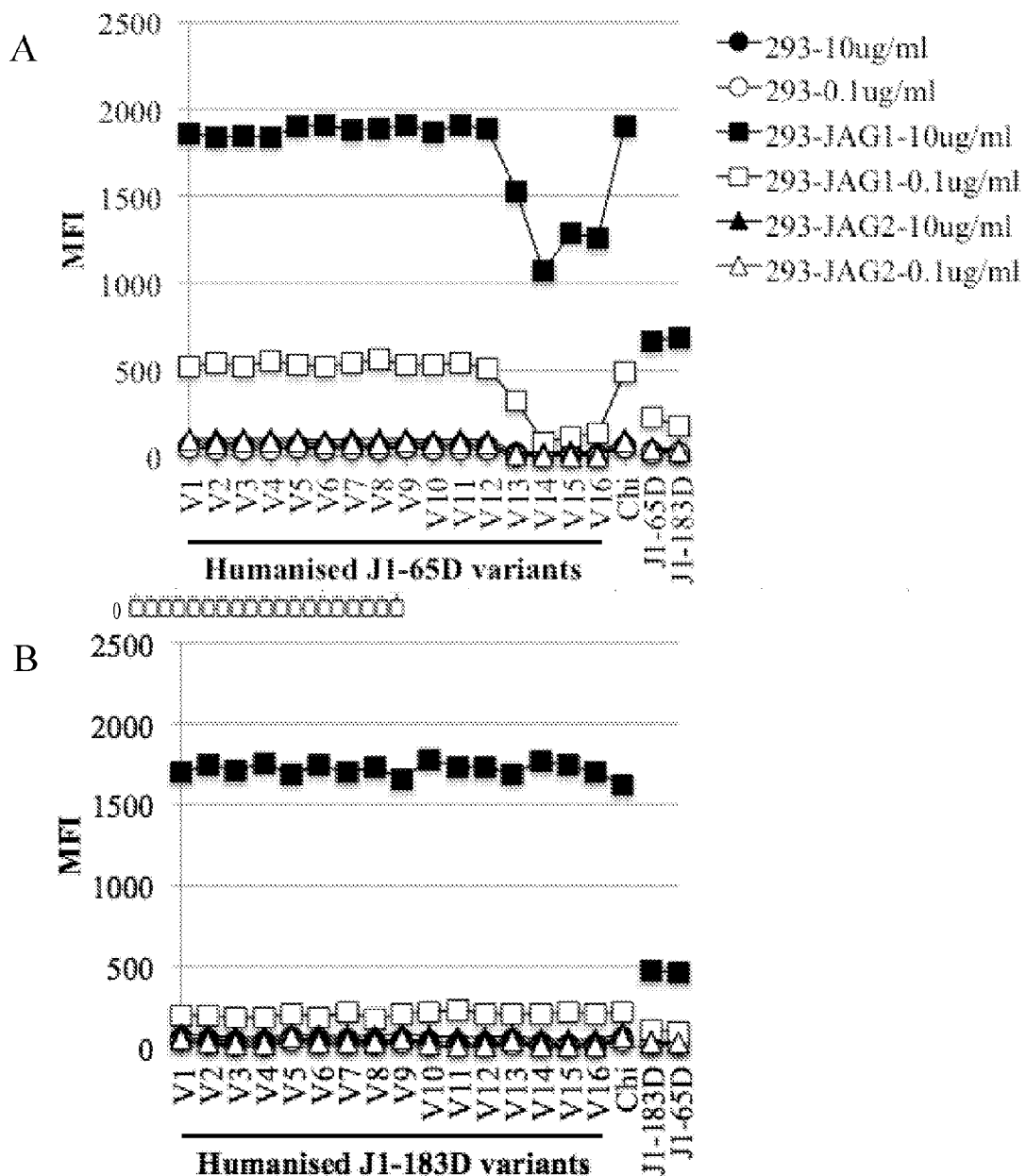
FIG. 18. Shows that humanised and de-immunised recombinant J1 mAb variants specifically bind cell surface over-expressed human J1 and not J2 protein. Sixteen humanised and de-immunised variants (V1-16) of each of the J1-65D (A) and J1-183D (B) antibodies, and a chimeric variant of each (Chi) were used to stain 293-JAG1 stable cells at the indicated concentrations followed by an anti-human-APC secondary antibody. Samples were analysed by FACS and the mean fluorescence intensities (MFI) were plotted. Parental cell 293 and control cell 293-JAG2 were also included as controls. Parental murine mAb (J1-65D, J-183D) staining was included as a positive control and detected using an anti-mouse-APC secondary antibody. With the exception of J1-65D variants 13-16, all the remaining antibodies effectively bound the human J1 protein.
Figure 19:
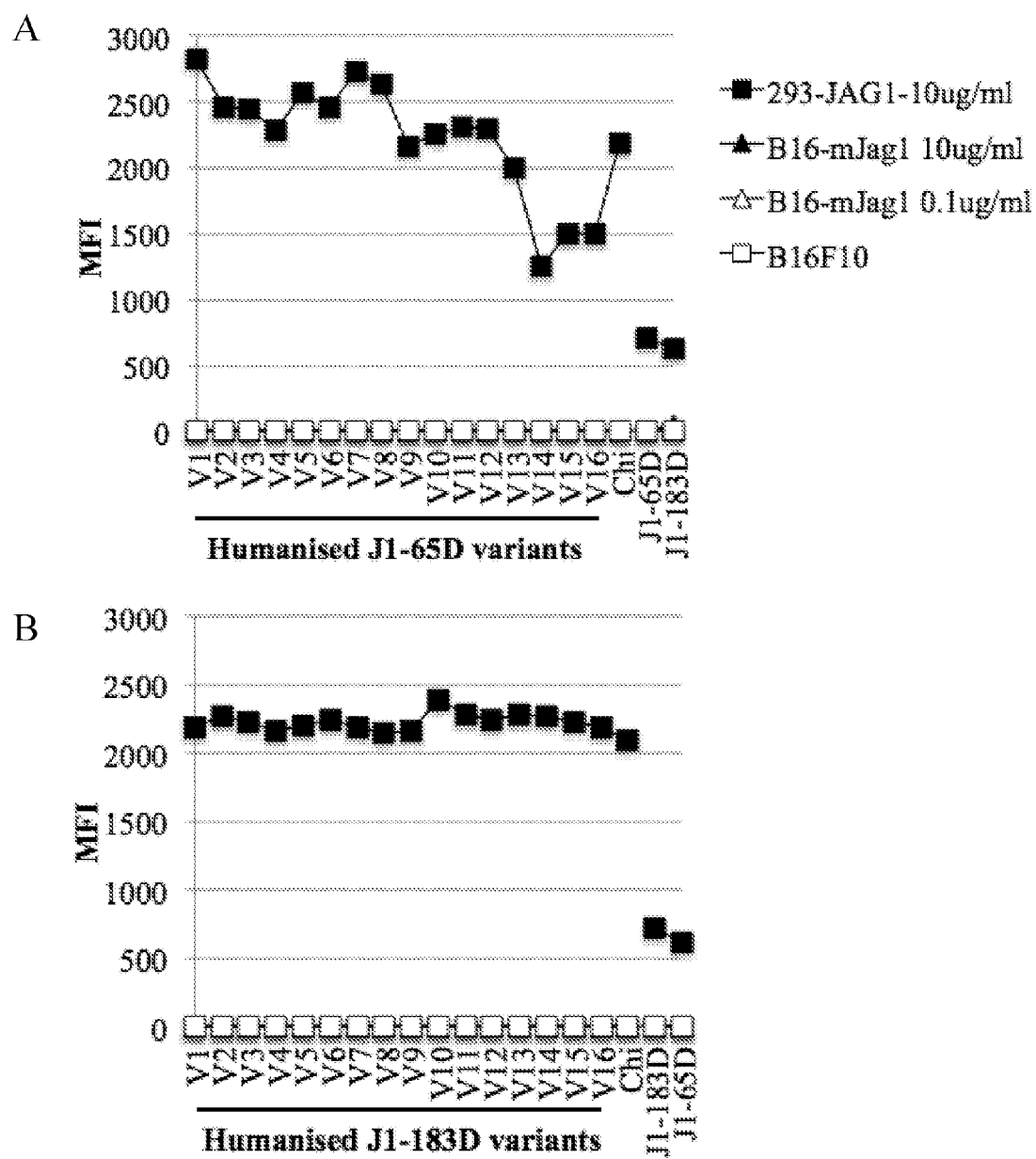
FIG. 19. Shows that humanised and de-immunised recombinant J1 mAb variants retain the specificity for human J1 and do not bind murine J1. Humanised J1-65D (A) and J1-183D (B) antibody variants, and a chimeric variant of each (Chi) were used to stain B16F10-mJAG1 over-expressing stable cells at the indicated concentrations followed by an anti-human-APC secondary antibody. Parental cell B16F10 and 293-JAG1 cells expressing human J1 were used as controls. Samples were analysed by FACS and the mean fluorescence intensities (MFI) were plotted. Original murine mAb (J1-65D, J1-183D) staining was detected by an anti-mouse-APC secondary antibody.

The four antibodies exhibit high specificity for the target protein, with minimal or no binding to two other human Notch ligands that also contain DSL domains: human Jagged 2 and human Delta-like ligand 4 (DLL4) (DSL domain sequence alignment may be found in Cordle et al. 2008 [65]), as demonstrated by immunocytochemical staining and FACS analysis (FIGS. 2 and 3). Accordingly, by producing a negative result in one or more binding assays (when compared with a positive control, see J2 Ab, FIG. 2 and hDLL4-GFP, FIG. 3), the antibodies of the present invention may be considered unable to specifically recognise either of two other DSL domain containing Notch ligands. Consequently, no inhibitory activity by the antibodies was observed on human Jagged 2 and DLL4-mediated signalling (FIG. 9B), indicating the likelihood of exclusive inhibition of Jagged 1-mediated signalling in a therapeutic context. Furthermore, in vitro blocking activity by the present antibodies is neither exhibited for mouse Jagged 1-mediated signalling (FIG. 10) nor the interaction between mouse Jagged 1 transfectants and recombinantly expressed human Notch 1 (FIG. 1). The molecular basis for the above observations was determined as the E228D substitution between human and mouse Jagged 1 (FIG. 7), thus demonstrating that the antibodies of the present invention all specifically recognise epitopes comprising residue E228 of human Jagged 1. Humanised and deimmunised variants of antibodies J1-65D and J1-183D retained these desirable characteristics (FIGS. 18 and 19).

Figure 14:
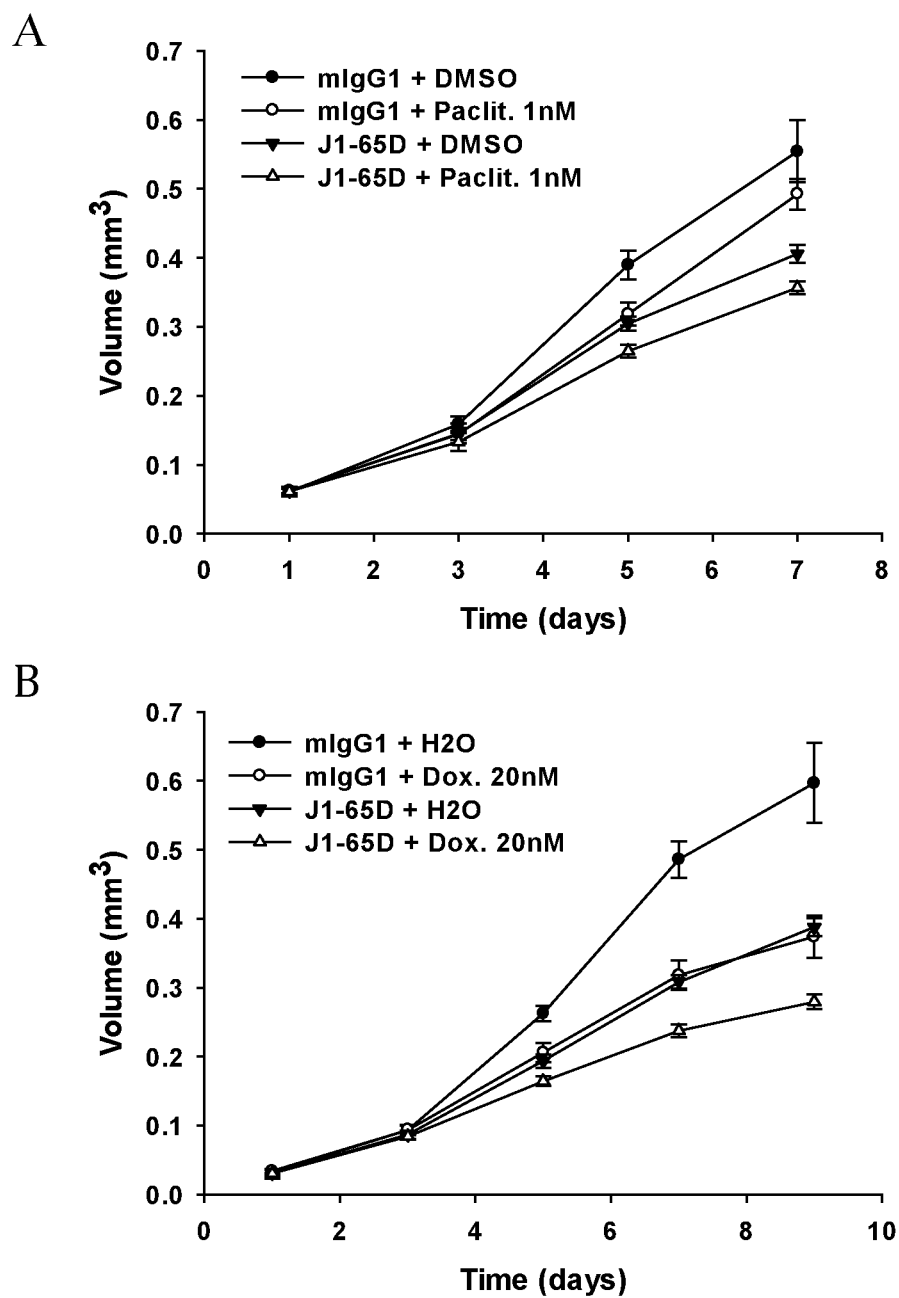
FIG. 14. Shows the effect of J1 mAb-chemotherapy treatment on 3-D growth of MDA-MB-231 spheroids in vitro. MDA-MB-231 breast cancer spheroids were treated with mAbs (10 µg/ml J1-65D or mIgG1 control mAb) in combination with sub lethal doses of breast cancer standard of care drugs (A) Paclitaxel (Paclit.) and (B) Doxorubicin (Dox.). Both combination treatments proved to be more effective at reducing spheroid growth than either single treatment alone.
Figure 15:
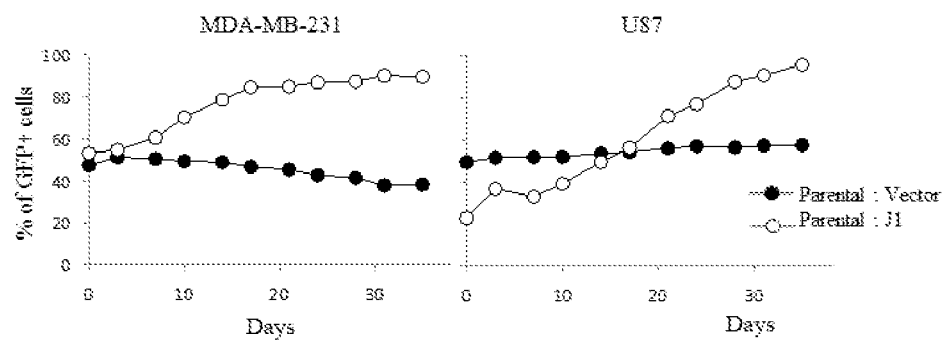
FIG. 15. Shows human J1 over-expression promotes tumour growth both in vitro and in vivo. (A) MDA-MB-231 and U87 cells were transduced with retrovirus encoding human J1 bi-cistronically with green fluorescence protein (GFP). J1 or vector transduced cells were mixed and co-cultured with parental cells and the GFP+ population was monitored by FACS regularly for 35 days. In both cell lines the J1 expressing cells exhibited a growth advantage over vector transduced cells in mixed co-culture with the parental cell line. (B) U87 cells transduced with J1 or vector alone were injected into BALB/c nu/nu mice (n=7) and tumour size was measured regularly to monitor tumour growth. U87 cells expressing human J1 exhibited a significant growth advantage in vivo.
Figure 15:
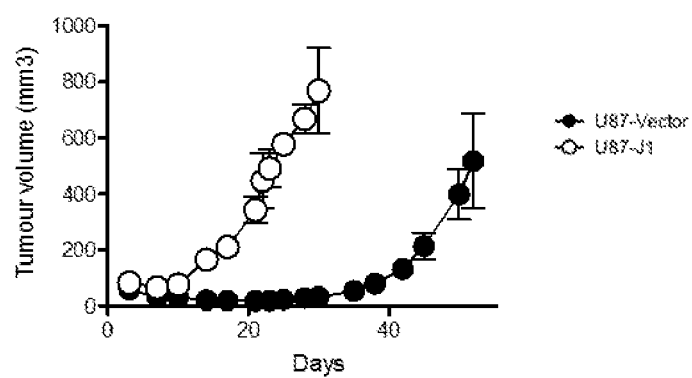
Figure 16:
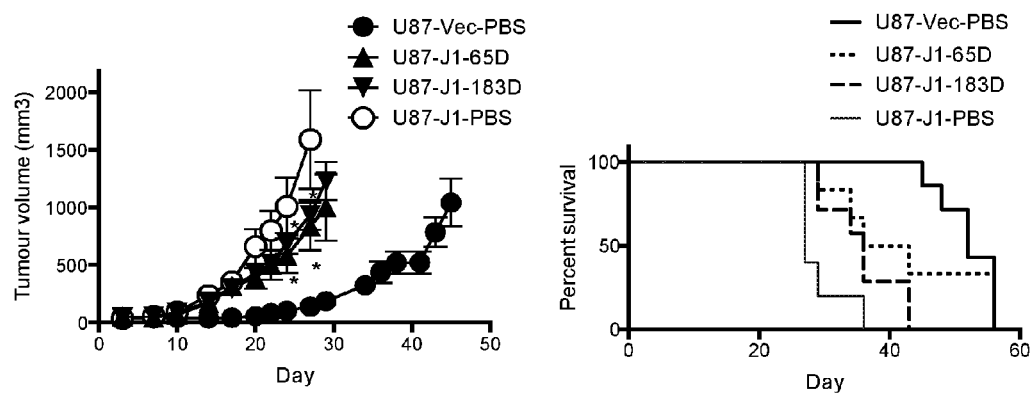
FIG. 16. Shows that at 10 mg/kg J1 mAbs delay J1 over-expression-induced tumour over-growth, while at 20 mg/kg they abolish J1 over-expression-induced tumour over-growth. (A, B) U87 cells transduced with J1 or vector alone were injected into BALB/c nu/nu mice (Experiment A U87-Vec-PBS and U87-J1-183D, n=7; U87-J1-PBS and U87-J1-65D, n=6; Experiment B U87-Vec-PBS, n=7; other groups: n=10). Animals were treated with intraperitoneal (i.p.) administration of J1-65D, or J1-183D mAb at (A) 10 mg/kg or (B) 20 mg/kg twice a week starting at the same time as tumour inoculation. Control groups were injected with equal volume of PBS, or 20 mg/kg of a control IgG1 mAb. Tumour size was measured regularly to monitor tumour growth. Survival curves were generated based on mouse sacrifice when tumour sizes reached geometric mean diameter (GMD) of 15 mm. *, $P<0.05$ comparing with (A) U87-J1-PBS group or (B) U87-J1-IgG1 group.
Figure 16:
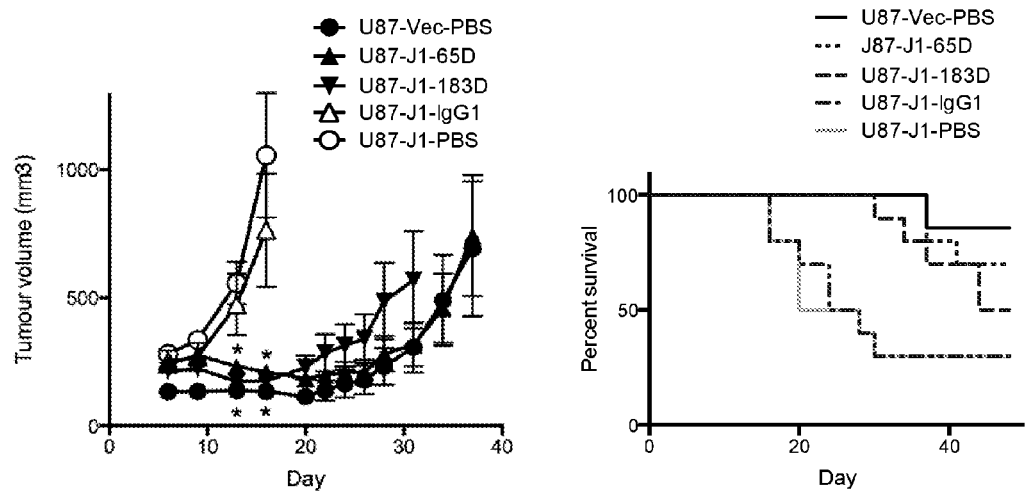

In contrast, with regard to human Jagged 1-mediated signalling, the antibodies of the present invention (in the form of hybridoma culture supernatants) exhibit effective in vitro blocking of the interaction between Jagged 1-transfected cells and recombinantly expressed, fluorescently labelled Notch 1, when analysed by FACS (FIG. 1). Furthermore, all antibodies (including selected humanised and de-immunised variants) demonstrate inhibition of Jagged 1-mediated Notch signalling in various tumour cell lines (FIGS. 9, 10B, 13, 17B and 20), in addition to the inhibition of tumour spheroid growth (FIGS. 11, 12, 13, 14, 21 and 22) which may be enhanced by combination treatment with standard of care chemotherapy drugs (FIG. 14); while tumoural Jagged 1 overexpression has been implicated as a critical factor enhancing tumour growth in vitro and in vivo (FIGS. 15 and 16). Notably, the present antibodies were able to effectively prevent tumour growth dependent on human Jagged 1 overexpression in vivo. Given the identification of CD46 as a novel receptor for Jagged 1 by Le Friec et al. (2012) [45] and the ability of the present antibodies to demonstrate inhibitory effects on Jagged 1-CD46 binding (FIG. 1B), this may also confer potential therapeutic benefit.

Further properties of the antibodies described herein are disclosed in the non-limiting examples.

The term "antibody" refers to an immunoglobulin which specifically recognises an epitope on a target as determined by the binding characteristics of the immunoglobulin variable domains of the heavy and light chains ($V_H$s and $V_L$s), more specifically the complementarity-determining regions (CDRs). The terms "monoclonal antibody" and "antibody" are herein used interchangeably, unless otherwise stated. Many potential antibody forms are known in the art, which may include, but are not limited to, a plurality of intact monoclonal antibodies or polyclonal mixtures comprising intact monoclonal antibodies, antibody fragments (for example $F_{ab}$, $F_{ab}'$, $F(_{ab}')_2$ and $F_v$ fragments, linear antibodies, single chain antibodies and multispecific antibodies comprising antibody fragments), single chain variable fragments ($scF_v$s), multispecific antibodies, chimeric antibodies, humanised antibodies and fusion proteins comprising the domains necessary for the recognition of a given epitope on a target. Antibodies may also be conjugated to various moieties for a therapeutic effect, including but not limited to cytotoxic drugs and radionuclides. An antibody may comprise $\gamma$, $\delta$, $\alpha$, $\mu$ and $\epsilon$ type heavy chain constant domains, wherein an antibody comprising said domains is designated the class IgG, IgD, IgA, IgM or IgE respectively. Classes may be further divided into subclasses according to variations in the sequence of the heavy chain constant domain (for example IgG1-4). Light chains are designated either $\kappa$ or $\lambda$ class, depending on the identity of the constant region.

The term "variable region" of an antibody refers to the variable region of the antibody light chain or the variable region of the antibody heavy chain, either alone or in combination. The variable regions of the heavy and light chains each consist of four framework regions (FR) connected by three complementarity determining regions (CDRs) also known as "hypervariable regions". The CDRs in each chain are held together in close proximity by the FRs and, with the CDRs from the other chain, contribute to the formation of the antigen-binding site of the antibody. There are at least two techniques for determining CDRs: (1) an approach based on cross-species sequence variability [79]; and (2) an approach based on crystallographic studies of antigen-antibody complexes [78]. In addition, combinations of these two approaches are sometimes used in the art to determine CDRs.

The term "monoclonal antibodies" refers to a homogenous population of antibodies (including the forms previously described, for example antibody fragments), which recognise a single epitope on a target. This is in contrast to polyclonal antibodies that typically include a mixture of different antibodies directed against different antigenic determinants. Furthermore, "monoclonal antibody" refers to such antibodies generated by any number of techniques including, but not limited to, hybridoma production, phage selection, recombinant expression, and transgenic animals.

The term "humanised antibody" refers to forms of non-human (e.g., murine) antibodies that are specific immunoglobulin chains, chimeric immunoglobulins, or fragments thereof that contain minimal non-human (e.g., murine) sequences.

The term "de-immunised antibody" refers to antibodies that are specific immunoglobulin chains, chimeric immunoglobulins, or fragments thereof that contain minimal sequences encoding potential T-cell epitopes.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammal (e.g., mouse, rat, rabbit, etc.) with the desired specificity, affinity, and/or capability while the constant regions are homologous to the sequences in antibodies derived from another species (usually human) to avoid eliciting an immune response in that species.

The term "epitope" refers to the portion of a target which is specifically recognised by a given antibody. In instances where the antigen is a protein, the epitope may be formed from either a contiguous or non-contiguous number of amino acids ('linear' or 'conformation' epitopes respectively), whereby in the case of the latter, residues comprising the epitope are brought together in the three-dimensional fold of the polypeptide. An epitope typically comprises, but is not limited to, 3-10 amino acids in specific positions and orientations with respect to one another. Techniques known in the art for determining the epitope recognised by an antibody (specifically whether or not an epitope comprises a given residue) include but are not limited to, site-directed mutagenesis or the use of suitable homologous proteins to the target protein, in combination with techniques for determining specific recognition or lack thereof, as exemplified below. By way of example and not limitation, an epitope may be determined as comprising a given residue by comparative analysis with a control comprising specific recognition of the native (non-substituted) target protein by said antibody; wherein diminished binding and/or lack of specific recognition by said antibody when compared with said control identifies a given residue as forming part of an epitope. Furthermore, structural analyses of antibody-target protein complexes via x-ray crystallography and/or nuclear magnetic resonance (NMR) spectroscopy, or suitable derivatives thereof, may also be used to determine the residues which constitute an epitope.

The term "portion" refers to anything less than the whole. By way of example, the DSL domain of Jagged 1 comprises 43 residues [65]. It would not be possible for an antibody to specifically recognise an epitope comprising the entire DSL domain as the CDRs of said antibody would have to substantially interact with each residue. Therefore the antibodies of the present invention may be described as specifically recognising a portion of the DSL domain of human Jagged 1. Human and mouse J1 DSL domains are shown as SEQ ID NOs 77 and 78, respectively.

The term "specifically recognises", in the context of antibody-epitope interactions, refers to an interaction wherein the antibody and epitope associate more frequently or rapidly, or with greater duration or affinity, or with any combination of the above, than when either antibody or epitope is substituted for an alternative substance, for example an unrelated protein. Generally, but not necessarily, reference to binding means specific recognition. Because of the sequence identity between orthologous proteins in different species, a monoclonal antibody may specifically recognise an epitope on a target such as a Jagged 1 protein in more than one species (by way of example, the antibodies of the present invention all specifically recognise human, rabbit, guinea pig and rat Jagged 1—FIG. 4). Likewise, because of homology between different Jagged proteins in certain regions of the polypeptide sequences of the proteins, specific recognition by a monoclonal antibody may include binding to an epitope on more than one Jagged protein (e.g., human Jagged 1 and human Jagged 2). Techniques known in the art for determining the specific recognition of a target by a monoclonal antibody or lack thereof include but are not limited to, FACS analysis, immunocytochemical staining, immunohistochemistry, western blotting/dot blotting, ELISA, affinity chromatography. By way of example and not limitation, specific recognition, or lack thereof, may be determined by comparative analysis with a control comprising the use of an antibody which is known in the art to specifically recognise said target and/or a control comprising the absence of, or minimal, specific recognition of said target (for example wherein the control comprises the use of a non-specific antibody). Said comparative analysis may be either qualitative or quantitative.

It is understood, however, that an antibody or binding moiety which demonstrates exclusive specific recognition of a given target is said to have higher specificity for said target when compared with an antibody which, for example, specifically recognises both the target and a homologous protein.

The terms "receptor" and "ligand" have their conventional meaning in the art.

The term "blocking", in the context of receptor-ligand interactions and antibody disruption thereof, refers to the ability of an antibody to disrupt the native interaction between a receptor and ligand, likely involving the specific recognition of an epitope on either the receptor or ligand. Techniques known in the art for determining the ability of an antibody to block a receptor-ligand interaction or lack thereof, include, but are not limited to, FACS analysis, cell-based assays comprising a reporter gene (for example luciferase) under the control of a downstream effector of ligand-mediated signalling, cell-based assays comprising analysis of transcription and/or translation of a target gene and/or protein of ligand-mediated signalling, cell-based assays comprising analysis of proteolytic processing, or otherwise modification, of at least one downstream component of ligand-mediated signalling. By way of example and not limitation, the ability to block, or lack thereof, may be determined by comparative analysis with a control comprising substantial inhibition of said receptor-ligand interaction and/or a control comprising the absence of, or minimal, inhibition of said receptor-ligand interaction. Said comparative analysis may be qualitative or quantitative. Said control comprising the absence of, or minimal, inhibition of said receptor-ligand interaction may comprise treatment with a non-specific protein or antibody.

The terms "polypeptide", "peptide" and "protein" are used interchangeably herein and have their conventional meaning in the art.

The terms "amino acid" and "residue" are herein used interchangeably and have their conventional meanings in the art. Specific amino acids are herein referred to by their conventional one and three letter codes; furthermore human Jagged 1 residues are numbered in accordance with Cordle et al. (2008) [65] and UniProt entry P78504 (http://www.uniprot.org).

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s), i.e., the one or more Jagged proteins to which the polypeptide or antibody binds. Methods of identifying nucleotide and amino acid conservative substitutions which do not eliminate antigen binding are well-known in the art.

The terms "identical" or percent "identity" in the context of two or more nucleic acids or polypeptides, refer to two or more sequences or sub-sequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software are known in the art that may be used to obtain alignments of amino acid or nucleotide sequences. These include, but are not limited to, BLAST and ALIGN. In some embodiments, two nucleic acids or polypeptides of the invention are substantially identical, meaning they have at least 70%, at least 75%, at least 80%, at least 85%, at least 90%, at least 95%, at least 96%, at least 97%, at least 98%, at least 99% nucleotide or amino acid residue identity, when compared and aligned for maximum correspondence, and measured using a sequence comparison algorithm or by visual inspection. In some embodiments, identity exists over a region of the sequences that is at least about 10, at least about 20, at least about 40-60 residues in length. In some embodiments, identity exists over a longer region than 60-80 residues, such as at least about 90-100 residues. In some embodiments the sequences are substantially identical over the full length of the sequences being compared, such as the coding region of a nucleotide sequence.

The terms "polynucleotide" and "nucleic acid," are used interchangeably herein and have their conventional meaning in the art.

The terms "cancer" and "cancerous" refer to or describe the physiological condition in mammals in which a population of cells are characterized by unregulated cell growth, proliferation and/or survival. Examples of cancer include, but are not limited to, carcinoma, lymphoma, blastoma, sarcoma, myeloma and leukaemia.

The terms "tumour" and "neoplasm" refer to any mass of tissue that results from excessive cell growth, proliferation and/or survival, either benign (noncancerous) or malignant (cancerous), including pre-cancerous lesions.

The terms "cancer cell" and "tumour cell" are grammatical equivalents referring to the total population of cells derived from a tumour or a pre-cancerous lesion, including both non-tumourigenic cells, which comprise the bulk of the tumour cell population, and tumourigenic stem cells (cancer stem cells, also described as CSCs). As used herein, the term "tumour cell" will be modified by the term "non-tumourigenic" when referring solely to those tumour cells lacking the capacity to renew and differentiate to distinguish those tumour cells from cancer stem cells.

The term "tumourigenic" refers to the functional features of a solid tumour stem cell including the properties of self-renewal (giving rise to additional tumourigenic cancer stem cells) and proliferation to generate all other tumour cells (giving rise to differentiated and thus non-tumourigenic tumour cells) that allow solid tumour stem cells to form a tumour. These properties of self-renewal and proliferation to generate all other tumour cells confer on cancer stem cells the ability to form palpable tumours upon serial transplantation into an immunocompromised host (e.g., a mouse) compared to non-tumourigenic tumour cells, which are unable to form tumours upon serial transplantation. It has been observed that non-tumourigenic tumour cells may form a tumour upon primary transplantation into an immunocompromised host after obtaining the tumour cells from a solid tumour, but those non-tumourigenic tumour cells do not give rise to a tumour upon serial transplantation.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The phrase "pharmaceutically acceptable excipient, carrier or adjuvant" refers to an excipient, carrier or adjuvant that can be administered to a subject, together with at least one antibody of the present disclosure, and which does not destroy the pharmacological and/or biological activity thereof and is nontoxic when administered in doses sufficient to deliver a therapeutic amount of the antibody.

The phrase "therapeutically effective amount" refers to an amount of an antibody, polypeptide, polynucleotide, small organic molecule, or other drug effective to "treat" a disease or disorder in a subject or elicit an effect on one or more cells in vitro. In the case of cancer, the therapeutically effective amount of the drug (e.g., an antibody) can reduce the number of cancer cells; reduce the tumour size; inhibit and/or stop cancer cell infiltration into peripheral organs including, for example, the spread of cancer into soft tissue and bone; inhibit and/or stop tumour metastasis; inhibit and/or stop tumour growth; relieve to some extent one or more of the symptoms associated with the cancer; reduce morbidity and mortality; improve quality of life; decrease tumourigenicity, tumourigenic frequency, or tumourigenic capacity of a tumour; reduce the number or frequency of cancer stem cells in a tumour; differentiate tumourigenic cells to a non-tumourigenic state; or a combination of such effects. To the extent the drug prevents growth and/or kills existing cancer cells, it can be referred to as cytostatic and/or cytotoxic. In the case of an effect on one or more cells in vitro, a therapeutically effective amount of antibody, polypeptide, polynucleotide, small organic molecule, or other drug may inhibit tumour cell growth when an immortalized cell line or a cancer cell line that expresses Jagged 1 on the cell surface, or tumour cells isolated from a patient sample such as, for example, a tissue biopsy, pleural effusion, bone marrow aspirate or blood sample is/are cultured in a medium containing said antibody, polypeptide, polynucleotide, small organic molecule, or other drug.

The terms "treating" and "treatment" and "to treat" and "alleviating" and "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of, or complete absence of, cancer cells; a reduction in the tumour size; inhibition of, or an absence of, cancer cell infiltration into peripheral organs including, for example, the spread of cancer into soft tissue and bone; inhibition of, or an absence of, tumour metastasis; inhibition of, or an absence of, tumour growth; relief of one or more symptoms associated with the specific cancer; reduced morbidity and mortality; improvement in quality of life; reduction in tumourigenicity, tumourigenic frequency, or tumourigenic capacity of a tumour; reduction in the number or frequency of cancer stem cells in a tumour; differentiation of tumourigenic cells to a non-tumourigenic state; or some combination of effects.

The term "and/or" as used in a phrase such as "A and/or B" herein is intended to include each of the following embodiments: A and B; A or B; A (alone) and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

In certain embodiments, a human Jagged 1-binding antibody according to the present invention is denoted J1-65D, which comprises a CDR-L1 having the amino acid sequence of SEQ ID NO: 1, CDR-L2 having the amino acid sequence of SEQ ID NO: 2, a CDR-L3 having the amino acid sequence of SEQ ID NO: 3, a CDR-H1 having the amino acid sequence of SEQ ID NO: 4, a CDR-H2 having the amino acid sequence of SEQ ID NO: 5 and a CDR-H3 having the amino acid sequence of SEQ ID NO: 6.

In certain embodiments, a human Jagged 1-binding antibody according to the present invention is denoted J1-156A, which comprises a CDR-L1 having the amino acid sequence of SEQ ID NO: 7, CDR-L2 having the amino acid sequence of SEQ ID NO: 8, a CDR-L3 having the amino acid sequence of SEQ ID NO: 9, a CDR-H1 having the amino acid sequence of SEQ ID NO: 10, a CDR-H2 having the amino acid sequence of SEQ ID NO: 11 and a CDR-H3 having the amino acid sequence of SEQ ID NO: 12. The antibody, unusually, also comprises a second light chain (VL2), comprising the following CDR amino acid sequences; CDR-L1 SEQ ID NO: 79, CDR-L2 SEQ ID NO: 80 and CDR-L3 SEQ ID NO:81. Antibodies having a single heavy chain but two light chains are described in [87].

In certain embodiments, a human Jagged 1-binding antibody according to the present invention is denoted J1-183D, which comprises a CDR-L1 having the amino acid sequence of SEQ ID NO: 13, CDR-L2 having the amino acid sequence of SEQ ID NO: 14, a CDR-L3 having the amino acid sequence of SEQ ID NO: 15, a CDR-H1 having the amino acid sequence of SEQ ID NO: 16, a CDR-H2 having the amino acid sequence of SEQ ID NO: 17 and a CDR-H3 having the amino acid sequence of SEQ ID NO: 18.

In certain embodiments, a human Jagged 1-binding antibody according to the present invention is denoted J1-187B, which comprises a CDR-L1 having the amino acid sequence of SEQ ID NO: 19, CDR-L2 having the amino acid sequence of SEQ ID NO: 20, a CDR-L3 having the amino acid sequence of SEQ ID NO: 21, a CDR-H1 having the amino acid sequence of SEQ ID NO: 22, a CDR-H2 having the amino acid sequence of SEQ ID NO: 23 and a CDR-H3 having the amino acid sequence of SEQ ID NO: 24.

The antibodies of the present invention may also have CDR sequences that differ from those disclose herein by way of amino acid substitution, deletion or insertion. The resulting antibody will retain the properties of specific recognition of an epitope comprising the DSL domain of human Jagged 1, including the residue E228, and blocking of the interaction between human Jagged 1 and its associated receptors. In certain embodiments the amino acid sequences of the CDRs of a human Jagged 1-binding antibody according to the present invention comprise 1, 2, 3, 4, 5, 6, 7, 8, 9 or 10 amino acid substitutions, deletions or insertions as compared to any one of SEQ ID NOs 1-6, preferably the amino acid sequences contain no more than 1, 2, 3 or 4 amino acid substitutions, deletions or insertions.

In certain embodiments the amino acid sequences of the CDRs of a human Jagged 1-binding antibody according to the present invention comprise 1, 2, 3, 4, 5, 6, 7, 8, 9 or 10 amino acid substitutions, deletions or insertions as compared to any one of SEQ ID NOs 7-12, optionally including those of SEQ ID NOs: 79-81, preferably the amino acid sequences contain no more than 1, 2, 3 or 4 amino acid substitutions, deletions or insertions.

In certain embodiments the amino acid sequences of the CDRs of a human Jagged 1-binding antibody according to the present invention comprise 1, 2, 3, 4, 5, 6, 7, 8, 9 or 10 amino acid substitutions, deletions or insertions as compared to any one of SEQ ID NOs 13-18, preferably the amino acid sequences contain no more than 1, 2, 3 or 4 amino acid substitutions, deletions or insertions.

In certain embodiments the amino acid sequences of the CDRs of a human Jagged 1-binding antibody according to the present invention comprise 1, 2, 3, 4, 5, 6, 7, 8, 9 or 10 amino acid substitutions, deletions or insertions as compared to any one of SEQ ID NOs 19-24, preferably the amino acid sequences contain no more than 1, 2, 3 or 4 amino acid substitutions, deletions or insertions.

In certain embodiments the amino acid sequences of the CDRs of a human Jagged 1-binding antibody according to the present invention are substantially identical when compared with SEQ ID NOs 1-6.

In certain embodiments the amino acid sequences of the CDRs of a human Jagged 1-binding antibody according to the present invention are substantially identical when compared with SEQ ID NOs 7-12, optionally including SEQ ID NOs: 79-81.

In certain embodiments the amino acid sequences of the CDRs of a human Jagged 1-binding antibody according to the present invention are substantially identical when compared with SEQ ID NOs 13-18.

In certain embodiments the amino acid sequences of the CDRs of a human Jagged 1-binding antibody according to the present invention are substantially identical when compared with SEQ ID NOs 19-24.

Specific variant CDR sequences are shown in Table 5, and antibodies constructed with one or more of these sequences are within the scope of the invention, with the exception of variants containing J1-65D-$V_L$-4. Antibodies constructed with combinations of the variant CDR sequences are shown in Table 6, and these are within the scope of the invention, again with the exception of J1-65D-$V_L$-4. The full-length $V_L$ and $V_H$ sequences are shown in FIGS. 23 and 24 (SEQ ID NOs 57-76) which show variations outside of the CDR sequences carried out for humanisation and/or deimmunisation.

All CDR sequences have been defined using the Kabat numbering system [79].

It is known in the art that insertion, substitution and/or deletion of CDR residues may result in increased or decreased affinity and/or specificity of an antibody for a given target. The effect of said insertions, substitutions and/or deletions is dependent upon variables including the nature of the epitope recognised by the antibody, the sequence and length of the CDRs prior to alteration, and in the case of substitutions, the properties of the new amino acid relative to that previously occupying the same position. Said alterations may be performed by the skilled person in order to improve binding properties such as affinity and/or specificity, using methods which are known in the art.

The skilled person would appreciate that the properties of specific recognition of an epitope comprising the DSL domain of human Jagged 1, including the residue E228, and blocking of the interaction between human Jagged 1 and its associated receptors, possessed by the antibodies of the present invention, may be substantially maintained or improved by the substitution of residues in 3 or fewer, 2 or fewer CDRs in a variable domain; wherein all residues, all residues except 1 of the CDR are substituted; wherein all substitutions, all substitutions except 1, all substitutions except 2 are non-conservative.

CDRs of varying length to those of the antibodies of the present invention may also confer the properties of specific recognition of an epitope comprising the DSL domain of human Jagged 1, including the residue E228, and blocking of the interaction between human Jagged 1 and its associated receptors. Insertions, substitutions and/or deletions of residues comprising the CDRs may also be performed by the skilled person for the purpose of humanising and/or de-immunising an antibody according to the present invention.

The present invention further provides pharmaceutical compositions comprising one or more of the human Jagged 1-binding antibodies described herein. In certain embodiments, the pharmaceutical compositions further comprise a pharmaceutically acceptable vehicle or diluent, examples of which are known in the art. These pharmaceutical compositions find use in inhibiting tumour growth and treating cancer in a subject (e.g., a human patient).

In certain embodiments, compositions are prepared for storage and use by combining a purified antibody of the present invention with a pharmaceutically acceptable vehicle (e.g., a carrier or excipient). Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propylparaben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG).

The pharmaceutical compositions of the present invention can be administered in any conventional way. Administration can be by parenteral administration, more particularly by intravenous administration. However, other routes of administration are also envisaged.

In certain embodiments, in addition to comprising a human Jagged 1-binding antibody, the pharmaceutical compositions of the present invention further comprise at least one additional therapeutic agent. In certain embodiments, the at least one additional therapeutic agent comprises 1, 2, 3, or more additional therapeutic agents.

In certain embodiments, an additional therapeutic agent can be administered prior to, concurrently with, and/or subsequently to, administration of the human Jagged 1-binding antibody during therapy (combination therapy). In some embodiments, the at least one additional therapeutic agent comprises 1, 2, 3, or more additional therapeutic agents. Combination therapy with at least two therapeutic agents often involves agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects. Combination therapy may decrease the likelihood that resistant cancer cells will develop. Combination therapy may allow for one therapeutic agent to be targeted to tumourigenic cancer stem cells, while a second therapeutic agent may be targeted to non-tumourigenic cancer cells.

It will be appreciated that the combination of a human Jagged 1-binding antibody and an additional therapeutic agent may be administered in any order or concurrently. In some embodiments, the human Jagged 1-binding antibody will be administered to patients that have previously undergone treatment with a second therapeutic agent. In certain other embodiments, the human Jagged 1-binding antibody and a second therapeutic agent will be administered substantially simultaneously or concurrently. For example, a subject may be given the human Jagged 1-binding antibody (e.g., an antibody) while undergoing a course of treatment with a second therapeutic agent (e.g., chemotherapy). In certain embodiments, the human Jagged 1-binding antibody will be administered within 1 year of the treatment with a second therapeutic agent. In certain alternative embodiments, the human Jagged 1-binding antibody will be administered within 10, 8, 6, 4, or 2 months of any treatment with a second therapeutic agent. In certain other embodiments, the human Jagged 1-binding antibody will be administered within 4, 3, 2, or 1 weeks of any treatment with a second therapeutic agent. In some embodiments, the human Jagged 1-binding antibody will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

Useful classes of therapeutic agents include, for example, antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an antimetabolite, an antimitotic, a topoisomerase inhibitor, or an angiogenesis inhibitor.

Therapeutic agents that may be administered in combination with the human Jagged 1-binding antibody include chemotherapeutic agents. Thus, in some embodiments, the method or treatment involves the combined administration of a human Jagged 1-binding antibody or antibody of the present invention and a chemotherapeutic agent or cocktail of multiple different chemotherapeutic agents. Treatment with an antibody can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously.

Chemotherapeutic agents useful in the instant invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethane; vindesine; dacarbazine; mannomustine; mitobronitol; mitolactol; pipobroman; gacytosine; arabinoside ("Ara-C"); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylomithine (DMFO); retinoic acid; esperamicins; capecitabine; and pharmaceutically acceptable salts, acids or derivatives of any of the above. Chemotherapeutic agents also include anti-hormonal agents that act to regulate or inhibit hormone action on tumours such as antiestrogens including for example tamoxifen, raloxifene, aromatase inhibiting 4(5)-imidazoles, 4-hydroxytamoxifen, trioxifene, keoxifene, LY1170 18, onapristone, and toremifene (Fareston); and antiandrogens such as flutamide, nilutamide, bicalutamide, leuprolide, and goserelin; and pharmaceutically acceptable salts, acids or derivatives of any of the above.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In certain embodiments, the second therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Antimetabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the second therapeutic agent is gemcitabine.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinca alkaloid, such as vincristine, binblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or PlkI. In certain embodiments, where the chemotherapeutic agent administered in combination with the human Jagged 1-binding antibody is an anti-mitotic agent, the cancer or tumour being treated is breast cancer or a breast tumour.

In certain embodiments, combination therapy involves the combined administration of a human Jagged 1-binding antibody of the present invention and radiation therapy. Treatment with the human Jagged 1-binding antibody can occur prior to, concurrently with, or subsequent to administration of radiation therapy by the skilled medical practitioner.

In some embodiments, a second therapeutic agent comprises an antibody. Thus, treatment can involve the combined administration of a human Jagged 1-binding antibody of the present invention with other antibodies against additional tumour-associated antigens including, but not limited to, antibodies that bind to EGFR, ErbB2, HER2, DLL4, Notch and/or VEGF. In certain embodiments, a second therapeutic agent is an antibody that is an angiogenesis inhibitor (e.g., an anti-VEGF antibody). In certain embodiments, a second therapeutic agent is bevacizumab (AVASTIN), trastuzumab (HERCEPTIN), panitumumab (VECTIBIX), or cetuximab (ERBITUX). Combined administration can include co-administration, either in a single pharmaceutical formulation or using separate formulations, or consecutive administration in either order but generally within a time period such that all active agents can exert their biological activities simultaneously.

Furthermore, combination therapy with the human Jagged 1-binding antibodies described herein can include treatment with one or more cytokines (e.g., lymphokines, interleukins, tumour necrosis factors, and/or growth factors)

Furthermore, treatment with the human Jagged-binding antibodies described herein can be accompanied by surgical removal of tumours, cancer cells or any other therapy deemed necessary by a treating physician.

The antibodies of the present invention may be used in the treatment of tumours/cancer. Said tumours/cancers include, but are not limited to, those comprising tumoural Jagged 1 expression and/or Jagged 1-mediated signalling, preferably wherein said expression and/or signalling is associated with pathological effects. Tumours/cancer comprising tumoural Jagged 1 expression and/or Jagged 1-mediated signalling include, but are not limited to: pancreatic cancer, B-cell chronic lymphocytic leukaemia, tongue squamous cell carcinoma, glioma, renal cancer, acute leukaemia, acute myeloid leukaemia, endometrial cancer, colorectal cancer, glioblastoma, breast cancer, prostate cancer, ovarian cancer, gastric cancer, ameloblastoma, Barrett's esophageal adenocarcinoma, lung cancer, medulloblastoma, multiple myeloma, neuroblastoma, head and neck cancer, cervical cancer, B-cell chronic lymphocytic leukaemia, diffuse large B-cell lymphoma, primary cutaneous $CD30^+$ lymphoproliferative disorders, Hodgkin's lymphoma, melanoma, hepatocellular carcinoma, tumours/cancer comprising cancer stem cells.

Tumours/cancer to be treated by the antibodies of the present invention will also include, but are not limited to, those comprising one or more tumour microenvironmental processes in which Jagged 1 and/or Notch-mediated signalling has been implicated, preferably wherein said processes are associated with pathological effects. Tumour microenvironmental processes in which Jagged 1 and/or Notch-mediated signalling has been implicated are relevant to multiple cancer types and include, but are not limited to: vascular maturation, angiogenesis, T cell-mediated immunosuppression, follicular dendritic cells, immune modulation by regulatory T cells, Epithelial-to-mesenchymal transition, CD46 signalling.

Tumours/cancer to be treated by the antibodies of the present invention will also include, but are not limited to, those comprising Jagged 1-mediated signalling between cells of the tumour/cancer and cells which comprise the tumour microenvironment.

The antibodies of the present invention may be expressed in recombinant form. Suitable host cells for expression of a recombinant human Jagged 1-binding antibody include prokaryotes, yeast, insect or higher eukaryotic cells under the control of appropriate promoters. Prokaryotes include gram-negative or gram-positive organisms, for example, E. coli or Bacilli. Higher eukaryotic cells include established cell lines of mammalian origin as described below. Cell-free translation systems can also be employed.

Various mammalian or insect cell culture systems are used to express recombinant protein. Expression of recombinant proteins in mammalian cells may be preferred because such proteins are generally correctly folded, appropriately modified and completely functional. Examples of suitable mammalian host cell lines include COS-7 (monkey kidney-derived), L-929 (murine fibroblast-derived), C127 (murine mammary tumour-derived), 3T3 (murine fibroblast-derived), CHO (Chinese hamster ovary derived), HeLa (human cervical cancer-derived) and BHK (hamster kidney fibroblast-derived) cell lines. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Baculovirus systems for production of heterologous proteins in insect cells are known to those of skill in the art.

An antibody of the invention may also be administered to a patient via gene therapy techniques, where by the patient is administered a polynucleotide that encodes the antibody. For example, a gene therapy vector, comprising a polynucleotide that encodes the antibody, may be administered, such that the antibody is expressed in vivo. The delivery of an antibody by such suitable techniques will be apparent to the skilled person [88], [89].

An antibody of the invention may also be delivered in conjunction with an oncolytic virus in the treatment of cancer. This may improve the bystander killing effect of such therapy.

The antibodies of the invention do not bind adequately to mouse Jagged 1, but do bind to rat Jagged 1. Accordingly, the antibodies of the invention can be used to block paracrine signalling between endogenous rat cell-derived Jagged 1 and a human cell line within a xenograft. This may be useful to test whether the antibodies are toxic and/or have increased efficacy. Accordingly, the present invention provides an assay for testing endogenously the toxicity and/or efficacy of an anti-Jagged 1 antibody, comprising administering the test antibody to a rat comprising a xenograft with a human cancer cell line and determining the toxicity effect, or determining the level of Notch signalling inhibition, where the antibody is as defined in claim 1.

The invention is now further described in the following non-limiting Examples.

Example 1—Generation of Anti-J1 Monoclonal Antibodies

To generate human J1-specific mAbs with the potential to block the binding of J1 to the Notch receptors, three human J1 antigens of different lengths were generated. These comprised the bacterially expressed and refolded DSL-EGF3 (DSL+EGF1-3) and DSL domain recombinant proteins, and a DSL domain-derived 18mer peptide corresponding to the region that was reported to mediate direct contact with the Notch protein [65]. These were used as immunogens to immunise MF1 mice. Hybridoma cell lines were generated through a standard fusion technique using the spleen cells from the immunised animals and a murine myeloma fusion partner cell line NS0. Screening by ELISA against the immunogens identified 99 reactive antibodies. Immunostaining and FACS against J1 transfected cells identified only 21 hybridomas that were able to recognise cell surface J1 (Table 1).

TABLE 1

Generation of anti-J1 monoclonal antibodies

| Immunogen | Fusion | ELISA positive | FACS positive |
|---|---|---|---|
| DSL-EGF3 | 4 | 74 | 20 |
| DSL | 2 | 9 | 1 |
| DSL peptide | 2 | 16 | 0 |

Example 2—Blocking and Binding Specificity of J1 mAbs

To functionally identify mAbs with the capacity to disrupt the J1-N1 protein:protein interaction, hybridoma culture supernatants were tested in a FACS-based binding assay. Biotinylated soluble human N1 EGF11-13 recombinant protein was bound to avidin-coated beads and used to stain J1-expressing cells in the presence or absence of each mAb that recognised cell surface hJ1 by FACS. Five (J1-65D, -156A, -183D, -187B and -142B, the latter of which is not an antibody according to the present invention) of the 21 mAbs were able to block N1 binding to J1 with different efficiencies: J1-65D, -183D and -156A completely blocked the binding, whereas J1-187B and -142B partially blocked binding (FIG. 1A). The four blocking antibodies of the invention were also able to block the binding of recombinant CD46 to a biotin-tagged J1 DSL-EGF3 recombinant protein in an ELISA assay (FIG. 1B). Thus demonstrating their ability to block J1 binding to multiple receptors. The four blocking mAbs of the invention were purified from serum-free culture supernatants and equal concentrations of purified antibodies were used to compare their activity in subsequent assays (unless hybridoma supernatant was specified). Sequence conservation across the DSL domain raised the possibility that the J1 mAbs may also be able to bind the Jagged 2 (J2) protein. Antibody binding specificity was initially tested by immunocytochemical labelling of cytospin samples of hJ1 and hJ2 transfectants (FIG. 2). All antibodies stained J1 transfectants but none stained the J2 transfected cells, and J2 expression in the same experiment was confirmed using a commercial anti-J2 antibody. The specificity of the purified mAbs was further investigated in mammalian cells transfected with hJ2, human Delta-like ligand 4 (hDLL4), or mJ1 (FIG. 3). Transfectants were FACS stained with 10 μg/ml of each of the four blocking mAbs. As seen previously all the mAbs stained hJ1 transfectants. Only weak binding of the J1-65D and J1-183D mAbs to mJ1 was observed which was consistent with these reagents being unable to functionally block binding of mJ1 to N1 (FIG. 1). None of the mAbs showed significant binding to hDLL4 while very weak binding to J2 was observed for J1-156A and J1-187B (FIG. 3).

To test the blocking efficiencies of the J1 mAbs, purified mAbs were titrated to determine the concentration required to block recombinant N1 binding to cell surface expressed hJ1. Beads coated with a bacterially-expressed N1 EGF11-13 protein were used to stain the hJ1-expressing cells in the presence of various concentrations of mAbs. As shown in Table 2, all mAbs tested were able to block N1 binding to J1 at lower than a therapeutically relevant concentration of 10 μg/ml. J1-65D and J1-183D showed the strongest inhibitory effect, being able to completely inhibit N1 binding at 1 μg/ml.

TABLE 2

Titration of J1 mAbs for blocking J1-N1 interaction

| | 0.2 μg/ml | 1.0 μg/ml | 2.0 μg/ml | 5.0 μg/ml |
|---|---|---|---|---|
| J1-65D | X | +++ | | |
| J1-183D | X | +++ | | |
| J1-156A | X | + | +++ | |
| J1-187B | X | X | + | +++ |

+++ Complete blocking
+ Partial blocking
X No effect

To quantify the binding affinity of these mAbs towards J1 protein, Surface Plasmon Resonance (SPR) was performed to investigate the binding of J1 mAbs with three different forms of J1 soluble protein: the bacterially-expressed immunogen DSL-EGF3 (J1-DE3), and two eukaryotically expressed longer forms that include the entire N-terminus until the third EGF domain (J1-NE3) or the entire N-terminus to EGF12 (J1-NE12). $K_D$ of each binding was measured as shown in Table 3. Consistent with data from the above-described binding and blocking experiments, J1-183D and J1-65D exhibited the highest binding affinity to all three forms of J1 proteins.

TABLE 3

Dissociation constants (Kd) of J1 mAbs to hJ1 proteins

| | J1-DE3 | J1-NE3 | J1-NE12 |
|---|---|---|---|
| J1-65D | 9.7 nM | 3.3 nM | 3.0 nM |
| J1-156A | 15.0 nM | 48.0 nM | 36.0 nM |
| J1-183D | 4.9 nM | 5.2 nM | 4.4 nM |
| J1-187B | 75.0 nM | 94.0 nM | 70.0 nM |

Figure 4:
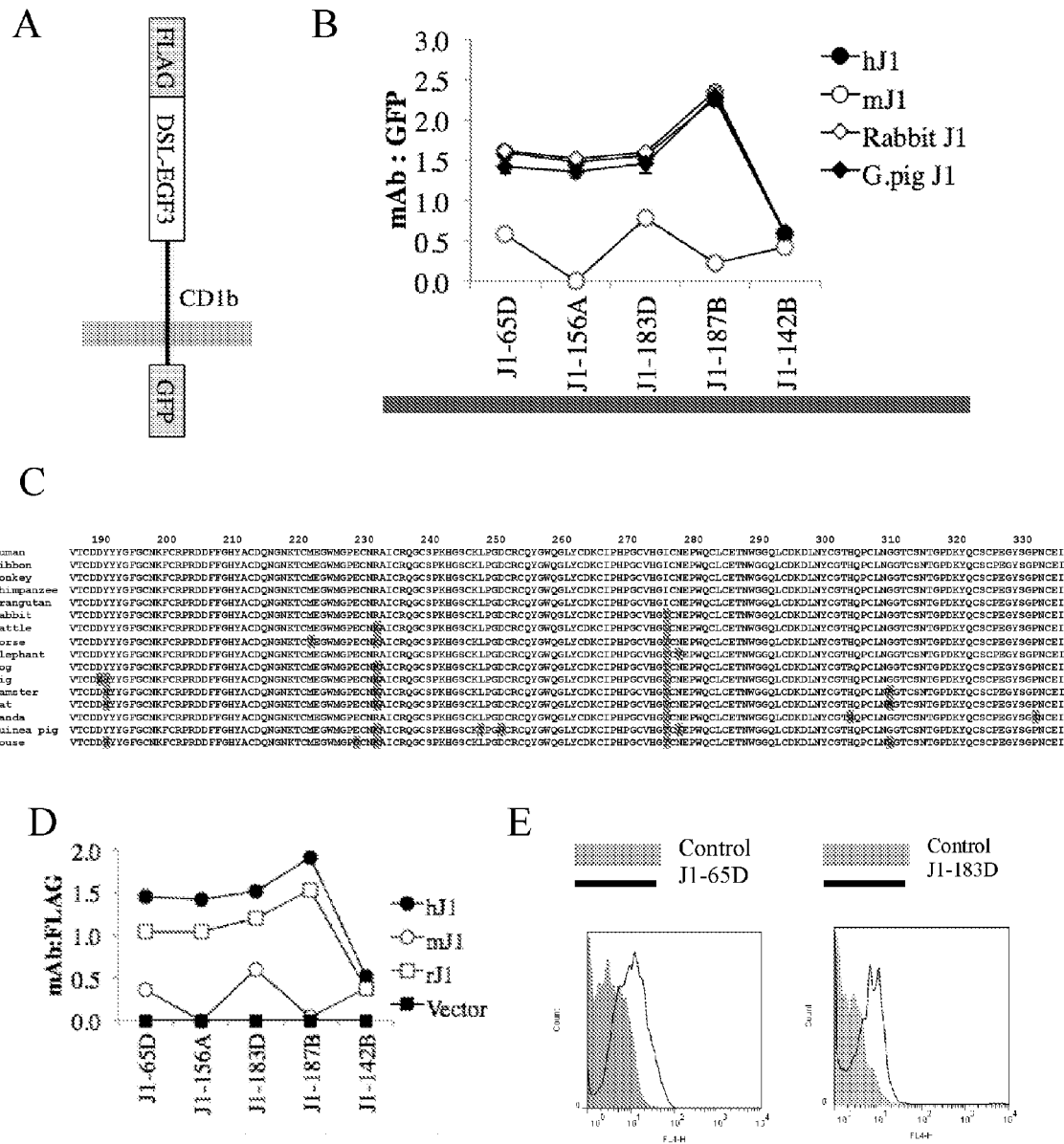
FIG. 4. Shows orthologous species binding specificity of J1 mAbs. (A) The DSL domain and the adjacent 3 EGF repeats (DSL-EGF3) with sequences corresponding to human (hJ1), murine (mJ1), rabbit, guinea pig and rat (rJ1) J1 proteins were expressed on cell surface by fusing with part of the CD1b molecule. An N-terminal FLAG tag and a C-terminal GFP tag were added. (B) HEK293T cells were transfected with the above hybrid constructs and cells were stained 48 h later. The intensity of mAb binding (MFI) was compared with that of anti-FLAG mAb staining to the same sample (n=2). (D) The experiment illustrated in panel B was then repeated to compare antibody binding to the human, murine or rat J1 proteins. (C) Alignment of DSL-EGF3 sequences across species (SEQ ID NOS 83-98, respectively, in order of appearance). (E) Primary adherent cells from rat spleen were immunolabelled with APC-conjugated mAb J1-65D or J1-183D and Jagged 1 expression was detected by FACS. The antibody denoted J1-142B is not an antibody according to the present invention, but acts as a positive control exemplifying specific recognition of mJ1.

The lack of blocking activity against murine J1 (FIG. 1) was potentially explained by DSL domain sequence differences between human and murine J1 proteins. Sequence alignment of J1 protein sequences corresponding to the DSL domain and EGF repeats from a range of species showed complete conservation in primates while DSL domain sequences were identical to the human in several species, including rodents such as rabbits and guinea pigs. To further investigate cross species reactivity the DSL domain and three EGF domains for human, murine, rabbit, guinea pig and rat J1 were epitope tagged and expressed on the cell surface and then tested for their ability to bind the J1 mAbs (FIG. 4). All four antibodies effectively bound rabbit, guinea pig and rat J1. The four antibodies bound mJ1 less effectively than the human protein and no binding was observed for J1-156A. Antibody binding to primary adherent cells isolated from rat spleen was confirmed for J1-65D and J1-183D, indicating binding of the native J1 protein in this species (FIG. 4).

Example 3—Recognition of J1 Expressed by Human Cancer Cell Lines

Most of the previous experiments were performed using recombinantly expressed J1. The ability of the J1 mAbs to bind endogenously expressed J1 was tested by FACS staining cancer cell lines derived from different tissue types, including breast cancer, leukaemia, lymphoma, myeloma, and colorectal cancer (Table 4 and FIG. 12A). The four J1 mAbs generally behaved similarly, although J1-65D and J1-183D stained a slightly broader cell line panel. This is consistent with their higher affinity for J1. The staining profiles demonstrating cell surface J1 expression were largely consistent with results from previous publications that detected J1 expression with other techniques such as RT-PCR and Western blotting [58, 59].

Interestingly multiple cell lines derived from diffuse large B-cell lymphoma (DLBCL), including DB, Karpas 422, OCI-Ly3, RIVA, SUDHL-10 and U-2932, were labelled using the J1 mAbs. DLBCL comprises 30-40% of adult non-Hodgkins lymphomas in Western countries and is heterogeneous both morphologically and clinically. Patients are commonly treated with CHOP (cyclophosphamide, doxorubicin, vincristine and prednisone) chemotherapy and the anti-CD20 monoclonal antibody rituximab (R-CHOP). There have been many different strategies for risk stratification in this patient group; examples include the International Prognostic index, cell-of-origin [poor prognosis activated B-cell-like (ABC) DLBCL or germinal centre B cell-like (GCB) DLBCL] and stromal signatures in the microenvironment (reviewed in [60]). Interestingly a poor prognosis stromal-2 signature implicated angiogenesis and blood vessel density as a predictor of adverse clinical outcome [61]. Microvessel density (MVD) has also been reported as an adverse prognostic factor in DLBCL [62].

Clinical trials combining R-CHOP with bevacizumab (anti-VEGF) have been tested in DLBCL patients as a strategy to target angiogenesis but have not been promising in terms of improved outcome and have resulted in increased serious toxicities [63]; despite bevacizumab having some promising activity a single agent [64]. Unfavourable risk-benefit assessment led Roche to accept the recommendation of an independent Data and Safety Monitoring Board to stop enrolment into their MAIN trial of bevacizumab+R-CHOP in DLBCL on 3 Jun. 2010. Notch2 gain of copy number and gain of function mutations have been reported in DLBCL [18] but there do not appear to be reports implicating J1 in the pathogenesis of this malignancy. Thus this is a Jagged 1 expressing malignancy where there is an unmet clinical need for additional drugs to target angiogenesis.

TABLE 4

Staining of human cancer cell lines and normal cells by J1 mAbs

|  |  | J1-65D | J1-156A | J1-183D | J1-187B |
|---|---|---|---|---|---|
| T-ALL | CEM | − | − | − | − |
|  | Jurkat | + | + | + | + |
|  | MOLT-4 | − | − | − | − |
| Myeloma | H929 | + | + | + | + |
|  | JJN3 | + | + | + | + |
|  | RPMI8226 | + | + | + | + |
|  | Thiel | + | + | + | + |
| Breast cancer | MDA-MB-231 | + | + | + | + |
|  | MDA-MB-453 | + | + | + | + |
|  | MDA-MB-468 | + | − | + | − |
|  | T47D | − | − | − | − |
|  | BT20 | + |  | + |  |
|  | BT459 | + |  | + |  |
|  | HCC1143 | + |  | + |  |
|  | HCC1806 | + |  | + |  |
|  | CAL-51 | + |  | + |  |
|  | MCF7 | +/− | − | +/− | − |
| B-NHL | DB | + | − | + | + |
|  | FL-18 | − | − | − | − |
|  | Granta 519 | + | − | + | − |
|  | Karpas 422 | + | + | + | + |
|  | Mieu | − | − | − | − |
|  | OCI-Ly1 |  |  |  |  |
|  | OCI-Ly3 | + | + | + | + |
|  | OCI-Ly8 | − | − | − | − |
|  | RIVA | + | + | + | + |
|  | SU-DHL10 | + | + | + | + |
|  | SU-DHL4 | − | − | − | − |
|  | SU-DHL6 | − | − | − | − |
|  | SU-DHL9 | − | − | − | − |
|  | U-2932 | + | + | + | + |
| HL | KM-H2 | − | − | − | − |
| Colorectal Cancer | LS174T | + |  | + |  |
|  | HCT116 | + | + | + | + |
|  | DLD-1 | + | + | + | + |
|  | HT-29 | + | + | + | + |
| Prostate Cancer | DU145 | − |  |  |  |
|  | PC3 | + | + | + | + |
| Ovarian Cancer | OVCAR-3 | + | + | + | + |
| Liver Cancer | HepG2 | + |  | + |  |
| Lung Cancer | H1993 | + |  | + |  |
|  | H1435 | + |  | + |  |
|  | H460 | + |  | + |  |
| Primary endothelial cells | HUVEC | + |  | + |  |

Figure 5:
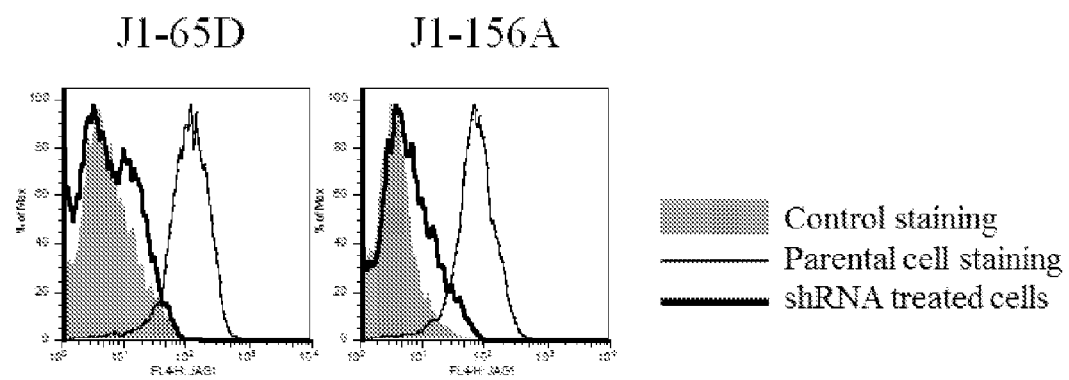
FIG. 5. Shows staining of endogenous J1 and knock down of J1 protein expression by shRNA. MDA-MB-231 cells were transduced with lentivirus encoding a Mission J1 shRNA, and J1 level of expression was detected by FACS at day 7 post transduction. J1 shRNA successfully knocked down Jagged-1 expression as visualised by J1 mAb staining.

To further validate the specificity of the J1 mAbs for detecting endogenous J1, gene knockdown was performed on a breast cancer cell line MDA-MB-231 using lenti-virus J1 shRNA (FIG. 5). As shown by FACS staining, J1 silencing completely abrogated binding with the two mAbs tested, thus confirming their specificity for J1.

Example 4—Epitope Mapping

Figure 6:
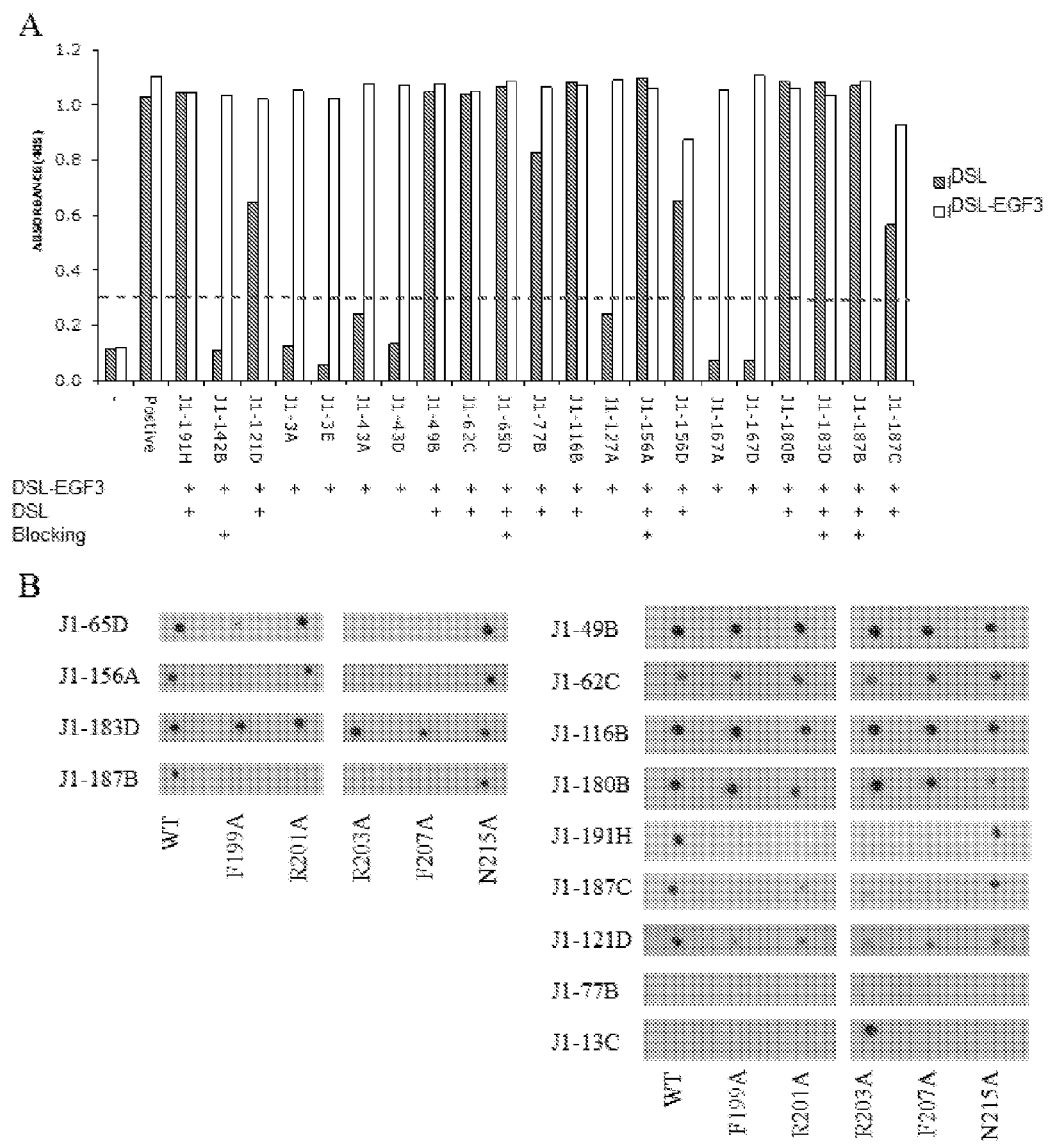
FIG. 6. Shows epitope mapping for J1 mAbs. (A) ELISA screening for mAbs binding to the J1 DSL domain. Hybridoma supernatants were screened by ELISA for binding to soluble bacterially expressed and in vitro refolded J1 recombinant proteins comprising the DSL domain alone (DSL) and/or the DSL domain and the first three EGF repeats (DSL-EGF3). Of the 21 FACS positive antibodies, 13 were able to bind the DSL domain alone, of which only four exhibited blocking activity. (B) Dot blot mapping J1 mAb epitopes. The key amino acids within DSL domain were mutated and soluble DSL-EGF3 recombinant proteins were used in dot blots to identify the amino acids responsible for mAb binding. Blocking mAbs (shown in the left panel) were used at 1:500 dilution of hybridoma supernatant and 10 ng mutant protein was used.

A conserved face of the DSL domain had been identified as being critical for Notch receptor binding [65]. Of the 21 anti-J1 mAbs that recognised J1 on the cell surface by FACS, 13 recognised epitopes contained within the DSL domain by ELISA (FIG. 6A). The remaining antibodies are likely to have epitopes within the EGF domains, epitopes that span the DSL-EGF domain boundary or those that are conformation sensitive and require a flanking domain.

As only four of the 13 anti-DSL domain targeting antibodies exhibited blocking activity our data clearly demonstrate that generating antibodies capable of binding to the DSL domain of J1 is not in itself sufficient to confer their ability to disrupt receptor-ligand binding.

Key amino acids in J1 (F199, R201, R203, D205, F207) are exposed on one face of the DSL domain and form a putative Notch binding site [65]. Mutant J1 proteins with alanine substitutions of the predicted key residues were then tested for their ability to prevent J1 mAb binding by dot blotting. None of the mutants prevented J1-183D mAb binding, but substitutions of F199, R201, R203, and F207 inhibited the binding of the other three mAbs (FIG. 6B, left panel). These results suggest that although all the mAbs were able to block receptor-ligand binding, they each may contact J1 protein at distinct amino acid residues.

Some of the non-blocking mAbs were also tested for their binding to these key residues (FIG. 6B, right panel). Most of these mAbs did not interact with the key amino acids, as their binding to the protein was not affected by the DSL domain substitutions (J1-49B, J1-62C, J1-116B, J1-180B, and J1-121D). This suggests that these non-blocking mAbs bind to J1 outside of the putative Notch binding site. But the binding of the other 4 mAbs, J1-191H, J1-187C, J1-77B and J1-13C, was clearly affected by these key residue substitutions, suggesting binding to these residues alone is not sufficient for blocking Notch interaction. Some antibodies (J1-62C, J1-191H, J1-187C, J1-121D, J1-77B and J1-13C)

required considerably higher concentrations of recombinant J1 protein to enable dot blot detection, thus a likely possibility is that the affinity of these mAbs for the J1 protein was too low to enable functional blockade of its binding to N1.

The four J1 blocking mAbs with epitopes within the DSL domain show functional species specificity by being able to block human J1, but not murine J1, binding to N1. Sequence alignment shows that there are only two amino acid differences between human and mouse J1 in their DSL domains, at positions 190 and 228 (FIG. 7A). An adjacent amino acid in the first EGF repeat (position 231) is also different. These further point mutations were used to determine whether or not the human-specific blocking effects of the mAbs were mediated by antibody binding to these key residues. Binding of all four DSL domain targeting J1 antibodies was prevented when the human glutamic acid residue at amino acid 228 was mutated to the murine aspartic acid residue (E228D). Mutation of Y190 in the DSL domain or R231 in EGF1 did not block binding, indicating that human J1 specificity is conferred primarily by E228 binding (FIG. 7B). The four J1 DSL domain targeting antibodies described here thus bind to a novel epitope/interface on the human J1 DSL protein (that includes amino acid E228) which is not conserved in the murine J1 protein and which is also absent in the human J2 protein. The E228D substitution did not prevent the binding of J1-142B mAb (not an antibody according to the present invention) which recognises human and murine J1 proteins.

Figure 8:
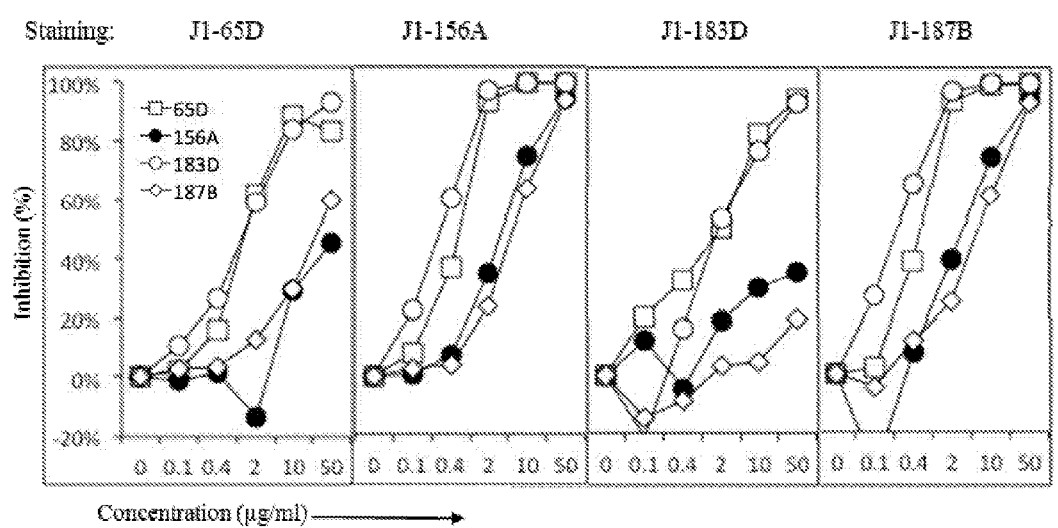
FIG. 8. Shows J1 blocking mAbs recognising closely related epitopes. HEK293-J1 stable cells were stained with biotinylated J1 mAbs in the presence of blocking mAbs at the indicated concentrations. The results suggest that the mAb epitopes are distinct but in sufficiently close physical proximity to prevent binding of multiple mAbs.

When the mAbs were each tested for their ability to block binding of the other mAbs to J1, all of them showed some ability to block binding of both themselves and the other mAbs (FIG. 8). The DSL domain epitopes all appeared to be physically close enough to prevent two different mAbs binding effectively to J1 at the same time. Thus while they may make contact with differing individual amino acids they all bind within a similar interface on the J1 DSL domain. The results suggest that there is unlikely to be any gain initially in using these antibodies together in combination therapy. However, as J1-65D and J1-183D both show good functional activity and recognise distinct amino acids within the DSL domain then there might be some value in using a second antibody within the context of acquired resistance to the first reagent if the binding activity of the second antibody remains effective.

Example 5—Functional Testing of mAb Blockade of Endogenous Notch Signalling

Having established that the J1 mAbs were able to block the binding of the J1 ligand to its receptor N1 their effect on the activity of the Notch signalling pathway was investigated. The human colorectal cancer cell line LS174T, stably expressing a luciferase reporter gene under control of Notch co-factor RBPJ, was stimulated with two forms of immobilised J1 protein: N-terminus to EGF3 and N-terminus to EGF12. Both proteins were found to activate luciferase reporter gene activity efficiently, and this induction was blocked by the γ-secretase inhibitor DBZ, a pan Notch inhibitor which also inhibited basal Notch signalling (FIG. 9A). When J1 mAbs were added to the culture system, luciferase activity was significantly inhibited, with J1-65D and J1-183D showing the strongest inhibition. Importantly, the best two J1 mAbs (J1-65D and J1-183D) were also tested against other Notch ligands in order to verify ligand specificity. As shown in FIG. 9B, none of these mAbs was able to prevent Notch activation induced by other tested ligands (J2 and DLL4).

The ability of the J1 mAbs to block Notch activation of an endogenous target gene, HES1, was also investigated (FIG. 9C). MDA-MB-231 cells, which express significant levels of N1 and J1, were treated with the J1 mAbs and the levels of Notch target gene activity were investigated. Similarly to the luciferase assay, all the J1 mAbs showed significant ability to reduce expression of a Notch regulated target gene. J1-65D and J1-183D were most effective at repressing HES1 transcription. To test whether any of the J1 mAbs could modulate expression of the Notch target Hes1 in murine cells, murine melanoma B16F10 cells overexpressing mJ1 were cultured in the presence of each J1 mAb, J1-142B mAb (as a positive control which binds the mJ1 protein), a negative control IgG1 mAb or the pan Notch inhibitor DBZ (FIG. 10A). Repression of Hes1 expression was observed using DBZ and to a lesser extent the J1-142B antibody. No repression was observed for the other anti-J1 antibodies or the control IgG1 antibody. The inability of antibodies J1-65D, J1-156A, J1-183D and J1-187B to block N1 signalling mediated via mJ1 in a fully murine system is consistent with their reduced binding to murine versus human J1 (FIGS. 3 & 4), as a consequence of E228 contributing to the epitope, and their functional inability to effectively block binding of mJ1 to N1 (FIG. 1). These data suggest that the four DSL domain targeting antibodies are functionally specific for blocking N1 binding and signalling mediated by human rather than murine J1 despite their weak binding to murine J1. The ability of the antibodies to bind rat J1 (FIG. 4D) suggested that they might be capable of inhibiting Notch signalling induced by rat J1. Indeed both J1-65D and J1-183D antibodies efficiently inhibited Notch signalling in both MDA-MB-231 and HUVEC cells stimulated with recombinant rat Jagged 1-Fc fusion protein (FIG. 10B). These data demonstrate that the ability of the antibodies to bind the rat J1 ligand is sufficient to block its Notch signalling activity.

Example 6—Tumour Growth Inhibition In Vitro Using a 3-D Spheroid-Based Assay

Under standard 2-D growth conditions the J1 mAbs did not inhibit growth of MDA-MB-231 breast cancer cells (data not shown). Similar findings were also reported for the Merck anti-N1 mAbs when tested on the LS-1034 cell line [66]. As cell-cell contact is required to activate Notch signalling a spheroid-based 3-D growth model was used to test the ability of the J1 mAbs to block tumour growth. Furthermore, the 3-D model better mimics in vivo conditions including hypoxia and acidosis, allowing evaluation of the mAbs effect in a more realistic setting. Spheroids were generated from MDA-MB-231 breast cancer cells and the ability of different concentrations of the J1-65D mAb to inhibit their growth was evaluated. Maximum growth inhibition was observed at a minimum antibody concentration of 5 µg/ml (FIG. 11A). As 10 µg/ml gave slightly better transcriptional repression of the Notch target gene HES1 and the pro-tumorigenic cytokine IL6 (FIGS. 11B and 11C, respectively) this concentration was selected for subsequent experiments.

Spheroids were generated with breast cancer cell lines expressing different levels of J1 (FIG. 12A), and their growth was monitored under J1 mAb treatment. It was found that the level of growth inhibition by J1 mAbs was strictly correlated with J1 expression levels. In fact, no significant effect was observed for MCF7 cells (almost undetectable J1 levels) (FIG. 12B) while gradually increasing growth inhibitory effect was observed for MDA-MB-468 (intermediate J1) and MDA-MB-231 (high J1) cell lines (FIG. 12C, D). In MDA-MB-231, both the J1-65D and J1-183D mAbs blocked spheroid growth with comparable effectiveness to the pan Notch inhibitor DBZ (FIG. 12D and FIG. 13A). Notch signalling inhibition was confirmed by qPCR for repression of expression of the Notch-target gene HES1 (FIG. 13B).

The mechanism by which the J1 antibodies inhibited tumour growth was investigated by immunolabelling, flow cytometric and qPCR analysis of spheroids harvested at the end of the experiment. Immunohistochemical studies identified minimal effects on proliferation, measured by the percentage of Ki67$^+$ cells (FIG. 13C). A reduction in the frequency of CD44+/CD24− cells (FIG. 13D), a population enriched in cancer stem cells, and in stem and progenitor cells expressing aldehyde dehydrogenase was observed (FIG. 13E). These data suggest that the Jagged 1 blocking antibodies deplete breast cancer stem cells in treated MDA-MB-231 spheroids. Analysis of the expression of other genes previously implicated in breast cancer biology, by qPCR, identified reduced expression of genes involved in growth and survival, IL6 (FIG. 13F) [67, 68] and CA9 (data not shown) [69, 70]. Increased expression of the epithelial marker E-cadherin and of PRRX1 (FIG. 13F) was a possible indication of reversal of the epithelial to mesenchymal transition [71-73], as also suggested by IL6 reduction itself.

Example 7—Additive Effects of Combination with Chemotherapy on Tumour Growth Inhibition In Vitro Using a 3-D Spheroid-Based Assay MDA-MD-231 breast cancer 3-D spheroids were treated with the J1-65D or J1-183D antibody in combination with sub lethal doses of the breast cancer standard of care drugs Paclitaxel (FIG. 14A) or Doxorubicin (FIG. 14B). Both combination treatments proved to be more effective at reducing spheroid growth than either single treatment alone.

Example 8—Inhibition of Tumour Growth Promotion Mediated by Human J1 Over-Expression In Vitro and In Vivo MDA-MB-231 breast cancer cells and U87 glioma cells were stably transduced with retrovirus encoding human J1 protein. Their growth in vitro was investigated by co-culturing the parental cells with J1-over-expressing cells. Vector-transduced cells were used as a control (FIG. 15A). In both cell lines, J1 over-expression significantly promoted cell growth as J1-transduced cells, but not the vector-transduced cells, over-grew their parental cells over time. In an in vivo model in which BALB/c nude mice were xenografted with U87 stable cells, the human J1 protein conferred a significant in vivo growth advantage on the growth of U87 xenografts (FIG. 15B).

The ability of the J1 blocking mAbs (J1-65D and J1-183D) to inhibit enhanced tumour growth dependent on human Jagged 1 overexpression was investigated (FIG. 16). At a dose of 10 mg/kg the blocking mAbs significantly delayed J1-induced tumour growth (FIG. 16A). While at 20 mg/kg the J1-65D completely abolished the enhanced tumour growth promoted by human Jagged 1 overexpression and the J1-183D antibody was considerably more effective than when given at a lower dose (FIG. 16B).

Example 9—Tumour Xenograft Growth Inhibition In Vivo

Figure 17:
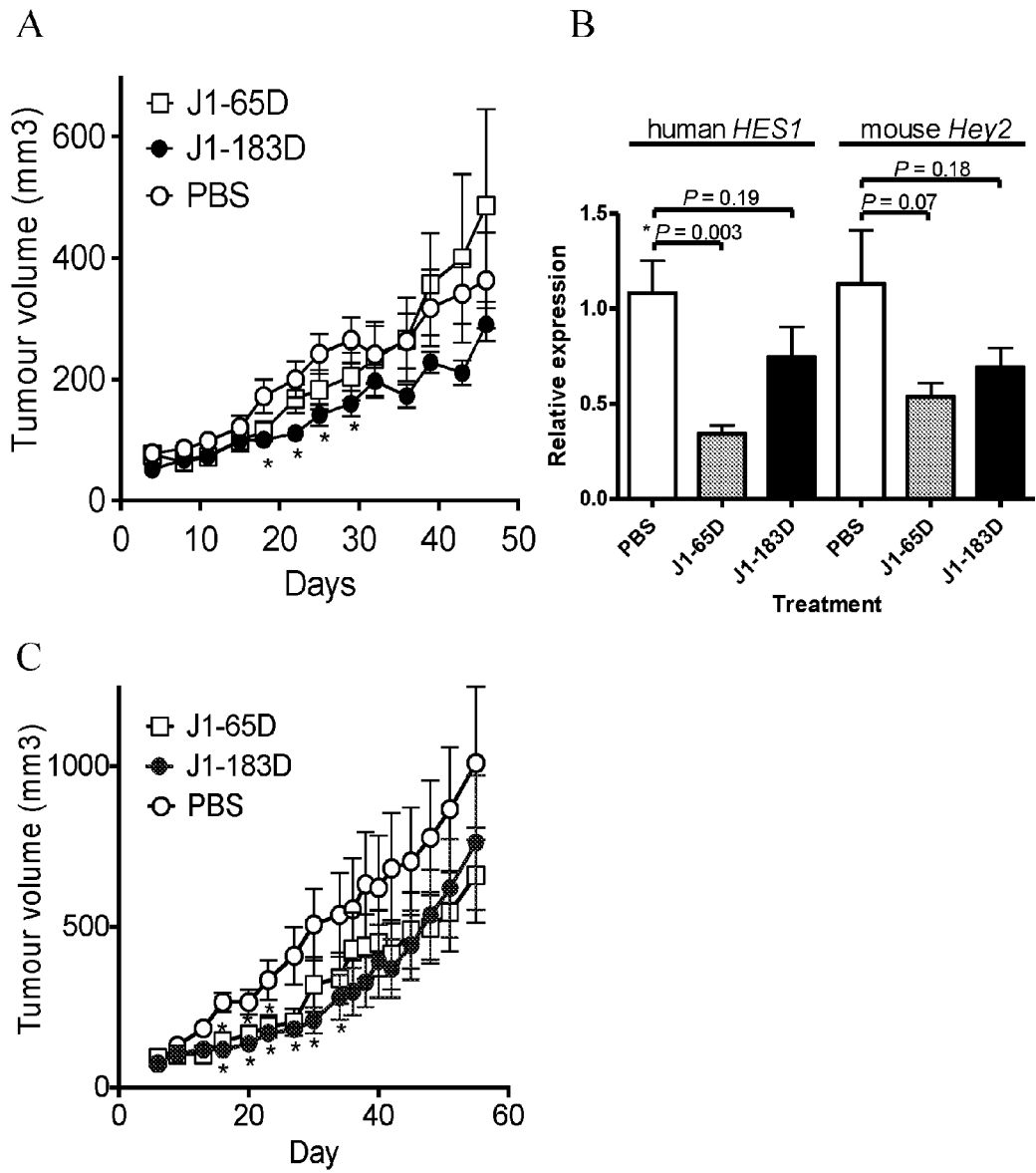
FIG. 17. Shows that J1 mAbs delay the early stages of MDA-MB-231 xenograft tumour growth in vivo. MDA-MB-231 cells were inoculated into BALB/c nu/nu mice (A, B n=7; C n=10). Animals were treated with intraperitoneal (i.p.) administration of J1-65D, or J1-183D mAb at either 10 mg/kg (A, B) or 20 mg/kg (C) twice a week starting at the same time as tumour inoculation. Control groups were injected with equal volume of PBS. Tumour size was measured regularly to monitor tumour growth. *, $P<0.05$ compared with PBS group. (B) Notch pathway inhibition in the 10 mg/kg treatment group was confirmed by qPCR analysis on RNA extracted from tumours. Reduction in both human and murine Notch-target genes was observed. Bars represent average of all tumours per group ±SE.

A xenograft model in which human breast cancer cell line MDA-MB-231 cells injected into BALB/c nude mice was used to investigate the effect of the J1 blocking mAbs (J1-65D and J1-183D) on tumour growth in vivo. When the mAbs were injected at the same time of tumour grafting followed by injecting once every 3 or 4 days, at 10 mg/kg dose blocking mAbs were able to slow down the tumour growth compared with the control group (FIG. 17A). The blocking mAb J1-183D showed the strongest inhibition (with significant growth reduction over 30 days), and J1-187B and J1-65D showed modest inhibition. At 20 mg/kg both blocking mAbs (J1-65D and J1-183D) significantly inhibited tumour growth during the first 36 days (FIG. 17C).

Species-specific PCR primers were developed and tested to individually analyse the expression of human or murine Notch target genes in the MDA-MD-231 xenografts harvested at the end of the experiment illustrated in FIG. 17A (FIG. 17B). Human Notch target genes are expressed in the xenografted tumour cells, while murine Notch target genes are expressed in murine cells in the tumour microenvironment and vasculature. Irrespective of whether the antibodies functionally inhibit only the human J1 protein or whether they also act on the murine J1 protein, cross-talk between the murine and human receptors/ligand and effects on tumour vascularity offers the opportunity for even human J1 specific antibodies to alter murine Notch target gene expression.

Initial analysis indicates that human HES-1 transcript expression was significantly repressed by both the J1-65D antibody, while a non-significant repression was observed using J1-183D. A non-significant trend towards murine Hey2 repression was observed in xenografts treated with each J1 mAb, suggesting that stromal Notch signalling mediated by murine J1 is not effectively targeted. These data confirm in vivo repression of the Notch pathway in breast cancer xenografts treated with J1 mAbs but suggest that the degree of repression of HES1 does not indicate which mAbs have the most effect on tumour growth.

Example 10—Humanised and De-Immunised Antibodies Retain their Specificity and Functionality In Vitro Humanisation and de-immunisation was outsourced to Lonza Biologics plc. Further protein engineering included avoidance/removal of potential post translational modifications and minimisation of changes to the iso-electric point. Four light chain and four heavy chain variants were designed in silico and combined to generate 16 antibody variants for both J1-65D and J1-183D (Table 5). A chimeric antibody containing the unaltered CDRs was also constructed.

TABLE 5

CDR region sequences of humanised/deimmunised J1-65D and J1-183D antibodies

| | CDR1 | CDR2 | CDR3 |
|---|---|---|---|
| J1-65D_VL Wildtype | RASGNIHNYLA (SEQ ID NO. 1) | NAKTLADDI (SEQ ID NO. 2) | QHFWSAPWT (SEQ ID NO. 3) |
| J1-65D_VL_1 | RASGNIHNYLA (SEQ ID NO. 1) | NAKTLADD<u>V</u> (SEQ ID NO. 26) | QHFWSAPWT (SEQ ID NO. 3) |
| J1-65D_VL_2 | RASGNIHNYLA (SEQ ID NO. 1) | NAKTLAD<u>A</u>V (SEQ ID NO. 27) | QHFWSAPWT (SEQ ID NO. 3) |

TABLE 5-continued

CDR region sequences of humanised/deimmunised J1-65D and J1-183D antibodies

| | CDR1 | CDR2 | CDR3 |
|---|---|---|---|
| J1-65D_VL_3 | RASGNIHNYLA (SEQ ID NO. 1) | NAKTLA<u>A</u>V (SEQ ID NO. 27) | QHFWSAPWT (SEQ ID NO. 3) |
| J1-65D_VL_4 NB non-functional | RAS<u>Q</u>GIHNYLA (SEQ ID NO. 25) | NAKTLADAV (SEQ ID NO. 27) | QQ FWSAPWT (SEQ ID NO. 28) |
| J1-65D_VH wildtype | DYEMH (SEQ ID NO. 4) | QPGGGGTAYNQKFKG (SEQ ID NO. 5) | RGYDDYPFAY (SEQ ID NO. 6) |
| J1-65D_VH_1 | DYEMH (SEQ ID NO. 4) | QPG<u>G</u>GGT<u>A</u>YNQKFKG (SEQ ID NO. 5) | RGYDDYPFAY (SEQ ID NO. 6) |
| J1-65D_VH_2 | DYEMH (SEQ ID NO. 4) | QPGGGGTAY<u>A</u>QKFKG (SEQ ID NO. 29) | RGYDDYPFAY (SEQ ID NO. 6) |
| J1-65D_VH_3 | DYEMH (SEQ ID NO. 4) | QPGGGGTAY<u>A</u>QKF<u>Q</u>G (SEQ ID NO. 30) | RGYDDYPFAY (SEQ ID NO. 6) |
| J1-65D_VH_4 | DYEMH (SEQ ID NO. 4) | QPGGGGTAY<u>A</u>QKF<u>Q</u>G (SEQ ID NO. 30) | RGYDDYPFAY (SEQ ID NO. 6) |
| J1-183D_VL Wildtype | RTSENIYSYLT (SEQ ID NO. 13) | NAKILAAGV (SEQ ID NO. 14) | QHHYDIPWT (SEQ ID NO. 15) |
| J1-183D_VL_1 | RTSENIYSYLT (SEQ ID NO. 13) | NAKILAAGV (SEQ ID NO. 14) | QHHYDIPWT (SEQ ID NO. 15) |
| J1-183D_VL_2 | RTSENIYSYLT (SEQ ID NO. 13) | NAKTLA<u>S</u>GV (SEQ ID NO. 31) | QHHYDIPWT (SEQ ID NO. 15) |
| J1-183D_VL_3 | RTSENIYSYLT (SEQ ID NO. 13) | NAKIL<u>D</u>SGV (SEQ ID NO. 32) | QHHYDIPWT (SEQ ID NO. 15) |
| J1-183D_VL_4 | RTSENIYSYLT (SEQ ID NO. 13) | <u>H</u>AKIL<u>D</u>SGV (SEQ ID NO. 33) | QHHYDIPWT (SEQ ID NO. 15) |
| J1-183D_VH wildtype | DYAIH (SEQ ID NO. 16) | NTYYGDSKYNQKFKD (SEQ ID NO. 17) | GYDGFAY (SEQ ID NO. 18) |
| J1-183D_VH_1 | DYAIH (SEQ ID NO. 16) | NTYYGDSKYNQKFKD (SEQ ID NO. 17) | GYDGFAY (SEQ ID NO. 18) |
| J1-183D_VH_2 | DYAIH (SEQ ID NO. 16) | NTYYGDSKY<u>A</u>QKFQG (SEQ ID NO. 34) | GYDGFAY (SEQ ID NO. 18) |
| J1-183D_VH_3 | DYAIH (SEQ ID NO. 16) | NTYYGDSKY<u>A</u>QKFQG (SEQ ID NO. 34) | GYDGFAY (SEQ ID NO. 18) |
| J1-183D_VH_4 | DYAIH (SEQ ID NO. 16) | NTYYGDSKY<u>A</u>QKFQG (SEQ ID NO. 34) | GYDGFAY (SEQ ID NO. 18) |

Underlining indicates amino acid differences from original CDR sequences.

The protein yield of these antibodies, their levels of soluble aggregates and their binding affinity to the immunogen (J1-DE3) are illustrated in (Table 6). With the exception of J1-65D variants containing the VL4 light chain (which lacked suitable affinity for the J1 antigen), all the antibodies demonstrated acceptable yields, levels of aggregates and affinity.

TABLE 6

Summary of transiently expressed J1-65D and J1-183D humanisation variants

| J1-65D Variant | Heavy chain | Light chain | Conc. (μg/ml) | Yield (mg) | % soluble aggregate | $K_D$(pM) |
|---|---|---|---|---|---|---|
| J1-65D murine | — | — | 1000 | — | 0.93 | 130 |
| J1-65D chimeric | J1-65D_VL | J1-65D_VH | 295 | 5.3 | 0 | 18.8--106 |
| J1-65D variant 1 | J1-65D_VL_1 | J1-65D_VH_1 | 200 | 3.6 | 0 | 150 |
| J1-65D variant 2 | J1-65D_VL_1 | J1-65D_VH_2 | 165 | 3.0 | 0 | 165 |
| J1-65D variant 3 | J1-65D_VL_1 | J1-65D_VH_3 | 295 | 5.3 | 1.67 | 158 |
| J1-65D variant 4 | J1-65D_VL_1 | J1-65D_VH_4 | 200 | 3.6 | 0 | 94.9 |
| J1-65D variant 5 | J1-65D_VL_2 | J1-65D_VH_1 | 170 | 3.1 | 0 | 44.6 |
| J1-65D variant 6 | J1-65D_VL_2 | J1-65D_VH_2 | 230 | 4.1 | 0 | 223 |
| J1-65D variant 7 | J1-65D_VL_2 | J1-65D_VH_3 | 250 | 4.5 | 0 | 151 |
| J1-65D variant 8 | J1-65D_VL_2 | J1-65D_VH_4 | 250 | 4.5 | 0 | 71.7 |
| J1-65D variant 9 | J1-65D_VL_3 | J1-65D_VH_1 | 160 | 2.9 | 0 | 13.9 |
| J1-65D variant 10 | J1-65D_VL_3 | J1-65D_VH_2 | 285 | 5.1 | 0.59 | 293 |
| J1-65D variant 11 | J1-65D_VL_3 | J1-65D_VH_3 | 310 | 5.6 | 1.00 | 243 |
| J1-65D variant 12 | J1-65D_VL_3 | J1-65D_VH_4 | 315 | 5.7 | 0.47 | 80.6 |
| J1-65D variant 13 | J1-65D_VL_4 | J1-65D_VH_1 | 130 | 2.3 | 2.82 | 14200 |
| J1-65D variant 14 | J1-65D_VL_4 | J1-65D_VH_2 | 305 | 5.5 | 6.61 | 58300 |
| J1-65D variant 15 | J1-65D_VL_4 | J1-65D_VH_3 | 255 | 4.6 | 5.29 | 39800 |
| J1-65D variant 16 | J1-65D_VL_4 | J1-65D_VH_4 | 245 | 4.4 | 5.60 | 52100 |

TABLE 6-continued

Summary of transiently expressed J1-65D and J1-183D humanisation variants

| J1-183D Variant | Heavy chain | Light chain | Conc. (μg/ml) | Yield (mg) | % soluble aggregate | $K_D$(nM) |
|---|---|---|---|---|---|---|
| J1-183D murine | — | — | 1000 | — | 2.32 | 0.58 |
| J1-183D chimeric | J1-183D_VL | J1-183D_VH | 180 | 3.2 | 1.41 | 0.39–1.35 |
| J1-183D variant 1 | J1-183D_VL_1 | J1-183D_VH_1 | 260 | 4.7 | 3.65 | 0.77 |
| J1-183D variant 2 | J1-183D_VL_1 | J1-183D_VH_2 | 260 | 4.7 | 3.58 | 2.19 |
| J1-183D variant 3 | J1-183D_VL_1 | J1-183D_VH_3 | 260 | 4.7 | 2.87 | 2.55 |
| J1-183D variant 4 | J1-183D_VL_1 | J1-183D_VH_4 | 210 | 3.8 | 0.85 | 2.76 |
| J1-183D variant 5 | J1-183D_VL_2 | J1-183D_VH_1 | 250 | 4.5 | 4.38 | 2.75 |
| J1-183D variant 6 | J1-183D_VL_2 | J1-183D_VH_2 | 240 | 4.3 | 4.6 | 1.39 |
| J1-183D variant 7 | J1-183D_VL_2 | J1-183D_VH_3 | 230 | 4.1 | 3.92 | 1.26 |
| J1-183D variant 8 | J1-183D_VL_2 | J1-183D_VH_4 | 205 | 3.7 | 0.93 | 1.48 |
| J1-183D variant 9 | J1-183D_VL_3 | J1-183D_VH_1 | 290 | 5.2 | 3.49 | 0.68 |
| J1-183D variant 10 | J1-183D_VL_3 | J1-183D_VH_2 | 290 | 5.2 | 2.89 | 1.77 |
| J1-183D variant 11 | J1-183D_VL_3 | J1-183D_VH_3 | 350 | 6.3 | 2.5 | 2.82 |
| J1-183D variant 12 | J1-183D_VL_3 | J1-183D_VH_4 | 290 | 5.2 | 0.66 | 2.61 |
| J1-183D variant 13 | J1-183D_VL_4 | J1-183D_VH_1 | 300 | 5.4 | 3.43 | 1.50 |
| J1-183D variant 14 | J1-183D_VL_4 | J1-183D_VH_2 | 300 | 5.4 | 3.02 | 3.91 |
| J1-183D variant 15 | J1-183D_VL_4 | J1-183D_VH_3 | 250 | 4.5 | 2.21 | 5.47 |
| J1-183D variant 16 | J1-183D_VL_4 | J1-183D_VH_4 | 290 | 5.2 | 0.72 | 4.86 |

The ability of the humanised antibody variants J1-65DV1-16 (FIG. 18A) and J1-183DV1-16 (FIG. 18B) to bind cell surface human J1 was compared to that of the chimeric antibody, which retained the parental CDR sequences. With the exception of J1-65DV13-16 (common VL4 light chain), all the variants retained comparable J1 binding activity and specificity to the chimeric antibody. None of the variants displayed J2 binding activity. The humanised antibody variants J1-65DV1-16 (FIG. 19A) and J1-183DV1-16 (FIG. 19B) also retained their specificity for human J1 and did not bind the murine J1 protein.

The FACS-based binding assay using biotinylated soluble human N1 EGF11-13 recombinant protein bound to avidin-coated fluorescent beads to stain J1-expressing cells was performed using a dilution series of each variant mAb to test their ability to block J1 binding to N1 by FACS (Table 7). With the exception of J1-65DV13-16 (common VL4 light chain), all the variants retained comparable in vitro blocking activity to their parental and chimeric antibody. Thus 12/16 J1-65D1 variants V1-12 and all J1-183D variants have the desired binding and blocking activity.

TABLE 7

Blocking of Notch1 binding to cell surface Jagged 1

| | Final antibody concentration | | | | |
|---|---|---|---|---|---|
| | 0.2 μg/ml | 0.4 μg/ml | 0.6 μg/ml | 1.0 μg/ml | 2.0 μg/ml |
| J1-65D murine | X | + | ≤+ | + | ND |
| Chimeric | X | + | + | + | ND |
| V1 | X | + | + | + | ND |
| V2 | X | + | + | + | ND |
| V3 | X | + | + | + | ND |
| V4 | X | + | + | + | ND |
| V5 | X | + | + | + | ND |
| V6 | X | + | + | + | ND |
| V7 | X | + | + | + | ND |
| V8 | X | + | + | + | ND |
| V9 | X | + | + | + | ND |
| V10 | X | + | + | + | ND |
| V11 | X | + | + | + | ND |
| V12 | X | + | + | + | ND |
| V13 | ND | ND | ND | Slight inhib$^n$ | Partial |
| V14 | ND | ND | ND | X | Partial |
| V15 | ND | ND | ND | X | Partial |
| V16 | ND | ND | ND | X | Partial |
| J1-183D murine | X | + | ≤+ | + | ND |
| Chimeric | X | + | + | + | ND |
| V1 | X | + | + | + | ND |
| V2 | X | + | + | + | ND |
| V3 | X | + | + | + | ND |
| V4 | X | + | + | + | ND |
| V5 | X | + | + | + | ND |
| V6 | X | + | + | + | ND |
| V7 | X | + | + | + | ND |
| V8 | X | + | + | + | ND |
| V9 | X | + | + | + | ND |
| V10 | X | + | + | + | ND |
| V11 | X | + | + | + | ND |
| V12 | X | + | + | + | ND |
| V13 | X | + | + | + | ND |
| V14 | X | + | + | + | ND |
| V15 | X | + | + | + | ND |
| V16 | X | + | + | + | ND |

ND, Not determined
+, Complete blocking
X, No blocking

Figure 20:
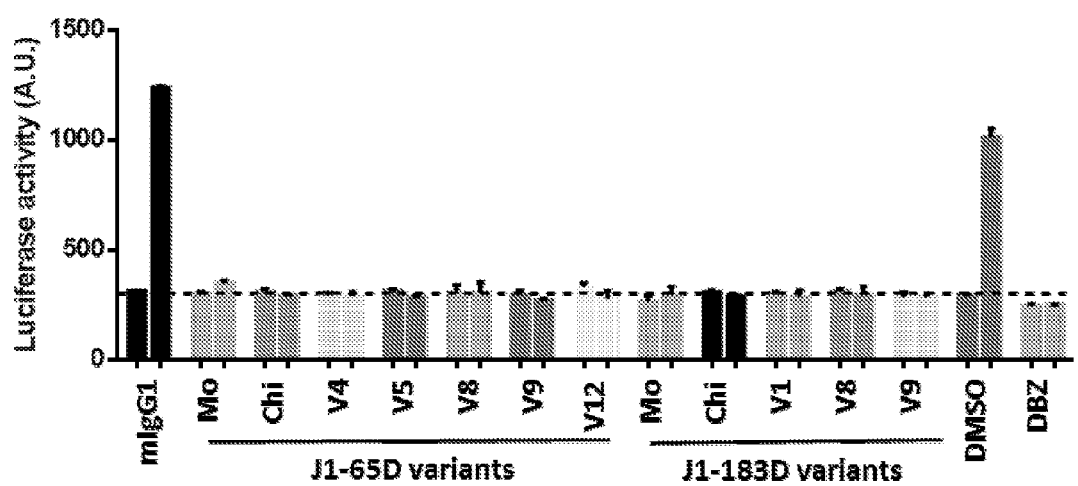
FIG. 20. Inhibition of human Jagged 1/Notch signalling by humanised and de-immunised J1-mAbs in vitro. The colorectal cancer cell line LS174T expressing luciferase under the control of Notch co-factor RbPJ was stimulated with mammalian cell-expressed recombinant J1 protein (NE3-Fc protein, right bar for each treatment) or a control protein (left bar) in the presence of J1 mAbs (10 μg/ml), and luciferase activity was measured. The parental murine monoclonal antibody (Mo), Murine IgG1, DMSO and DBZ were used as controls. All tested J1-65D and J1-183D antibody variants, including a chimeric antibody (Chi) effectively blocked J1 induced Notch signalling.
Figure 21:
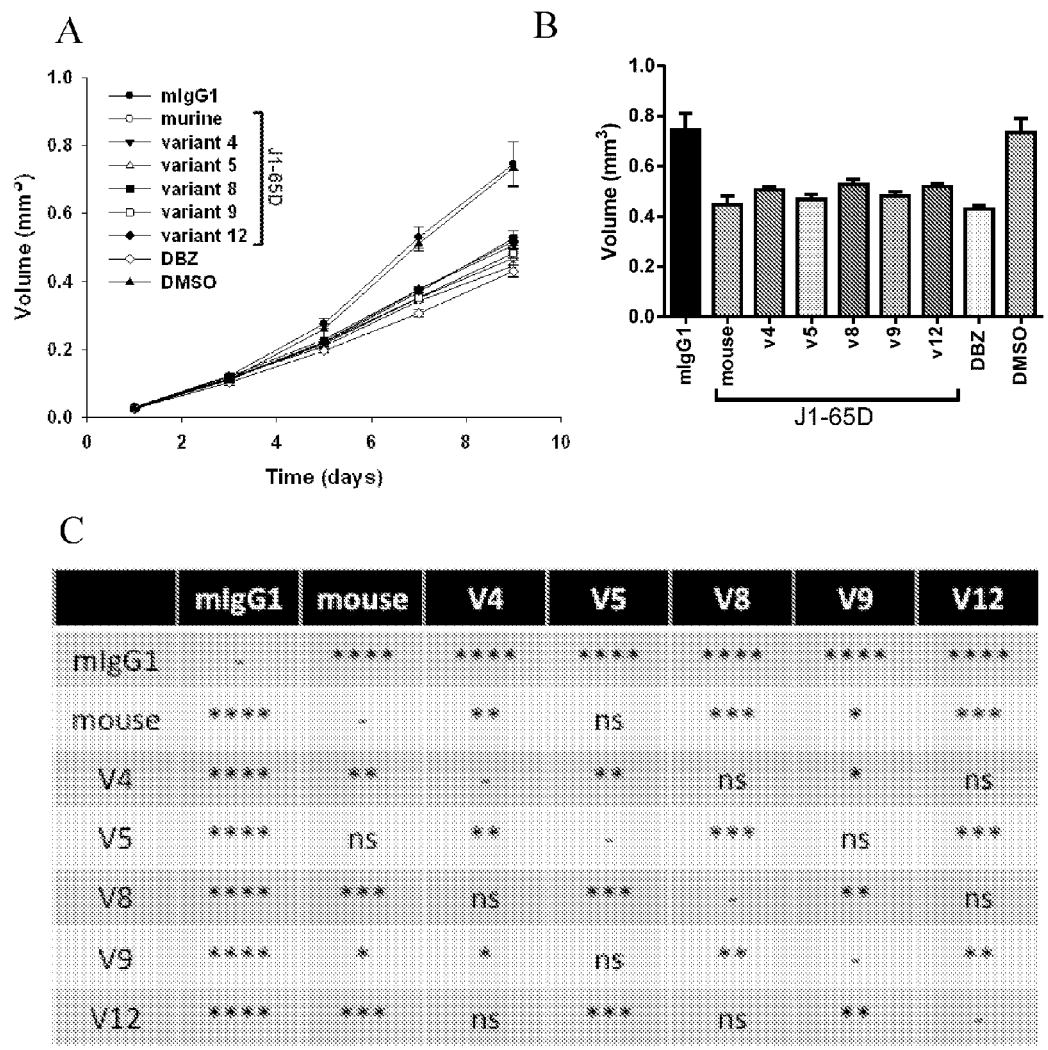
FIG. 21. Shows effects of humanised and deimmunised J1-65D antibodies on MDA-MB-231 3-D growth. MDA-MB-231 breast cancer cells were grown as spheroids in the presence or absence of J1-65D (anti-Jagged 1 mAb) or a mIgG1 (control mAb), All antibodies were used at 5 μg/ml, the lowest concentration inducing the maximal growth reduction (see FIG. 11). The original murine antibody (murine or mouse) or DBZ were included as positive controls, while DMSO and mIgG1 were used as negative controls. (A) Growth curve of treated tumour cell spheroids. (B) Spheroid size at culture day 9 (5-6 spheroids per group). (C) Statistical analysis comparing each pair of antibodies.

Having established that the humanised and deimmunised J1 mAbs were able to block the binding of the J1 ligand to its receptor N1 their effect on the activity of the Notch signalling pathway was investigated. The human colorectal cancer cell line LS174T, stably expressing a luciferase reporter gene under control of Notch co-factor RBPJ, was stimulated with immobilised J1 protein (N-terminus to EGF3) which activated luciferase reporter gene activity efficiently, and this induction was blocked by the γ-secretase inhibitor DBZ, a pan Notch inhibitor (FIG. 20). When selected humanised J1 mAbs (J1-65DV4, V5, V8, V9, V12 or J1-183DV1, V8, V9) or chimeric antibodies were added to the culture system, luciferase activity was inhibited as effectively as by the parental murine mAb.

Figure 22:
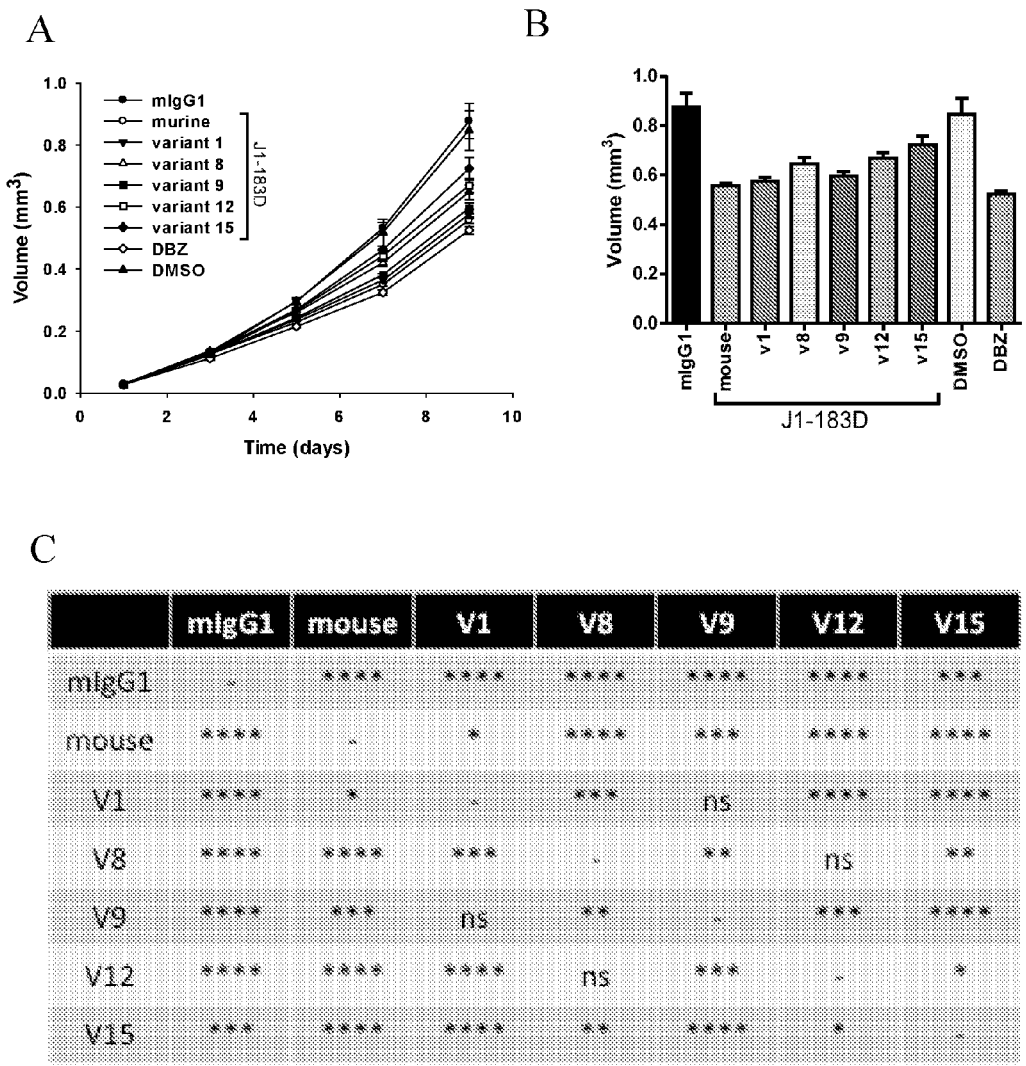
FIG. 22. Shows effects of humanised and deimmunised J1-183D antibodies on MDA-MB-231 3-D growth. MDA-MB-231 breast cancer cells were grown as spheroids in the presence or absence of J1-183D (anti-Jagged 1 mAb) or a mIgG1 (control mAb), All antibodies were used at 5 μg/ml, the lowest concentration inducing the maximal growth reduction (see FIG. 11). The original murine antibody (murine or mouse) or DBZ were included as positive controls, while DMSO and mIgG1 were used as negative controls. (A) Growth curve of treated tumour cell spheroids. (B) Spheroid size at culture day 9 (5-6 spheroids per group). (C) Statistical analysis comparing each pair of antibodies.

The ability of the humanised and deimmunised antibodies to inhibit the 3-D growth of MDA-MB-231 breast cancer spheroids was also investigated. An antibody concentration of 5 μg/ml was selected for this experiment to determine whether reducing the mAb concentration would help to identify functional differences between the humanised variants. For the J1-65D variants (FIG. 21), all those tested significantly reduced spheroid growth compared to the mIgG1 control. The ability of J1-65DV5 and J1-65DV9 to inhibit spheroid growth was most comparable to the parental mAb (FIG. 21), while variants J1-65DV4, 8 and 12 showed slightly reduced ability to inhibit spheroid growth. For the J1-183D variants (which generally exhibited lower affinity for J1 than the J1-65D variants) all those tested significantly reduced spheroid growth compared to the mIgG1 control, but overall there were more noticeable differences in their ability to inhibit spheroid growth (FIG. 22). J1-183DV1 exhibited most comparable efficacy to the original murine antibody, while variants 9, 8, 12 and 15 showed increasingly less effect. This corresponded closely to their affinity for Jagged 1 highlighting its functional importance in this assay. Overall these data identify a panel of J1 binding and blocking humanised antibodies that retain the functional ability of the parental murine mAb to inhibit Notch signalling and tumour growth in vitro.

The following materials and methods exemplify those used by the present inventors.

Generation of Anti-J1 Monoclonal Antibodies

Part of the human J1 extracellular region that contains the DSL domain and the 3 adjacent EGF repeats (amino acids 185-335) was expressed with an N-terminal His6 tag (SEQ ID NO: 82) and a C-terminal biotinylation tag in E. coli NM554 as described previously [65]. A similar construct encoding DSL domain (amino acids 185-230) was expressed in similar way. The proteins were purified from cell lysate by $Ni^{2+}$-affinity chromatography, refolded in vitro and further purified with anion exchange FPLC and reverse phase HPLC. A reduced peptide derived from DSL domain (amino acids 197-214 NKFCRPRDDFFGHYACDQ (SEQ ID NO.35)) was synthesised commercially by GenScript, refolded and conjugated with Keyhole limpet hemocyanin.

MF1 mice (6-8 week old female) were immunised with the purified proteins or peptide following standard protocol, i.e., 100 μg per immunisation each mouse every 10 days for three times. Forty days post the first immunisation, boost immunisation was given and fusions were performed two days later. Standard fusion protocol was followed with NS0 cells as a fusion partner and hybridomas were allow to growth under hypoxanthine, aminopterin and thymidine (HAT) selection.

Hybridoma supernatants were screened for the presence of secreted antibodies that were reactive with the immunogen, by ELISA. Positive cell lines were then cloned by limiting dilution. Supernatants from hybridomas were further screened for binding to HEK293T cells transfected with human J1 and for blocking the binding of human N1 soluble protein to J1 transfected cells.

Purified antibodies were produced by either adapting the hybridoma cells to serum-free medium or by bulk culturing cells in serum-free medium followed by protein A or protein G purification. Purified antibodies were again tested specificity for binding and blocking by ELISA and FACS assays.

ELISA for Identifying mAbs that Bind Jagged 1

Ninety-six well MaxiSorp plates were coated with the appropriate J1 antigen at 10 μg/ml in PBS at 4° C. overnight. The plates were then washed with PBS/0.1% Tween-20 and blocked with 1% BSA in PBS for 2 h at room temperature. The plates were washed again before adding hybridoma supernatants and incubated for 1 h. After washing, HRP conjugated anti-mouse secondary antibody was added at 1:1000 dilution to each well and incubated for 1 h. Substrate ABTS was added to each well after washing and OD405 nm was measured with a plate reader within 5-30 min.

Expression Constructs

IMAGE clone for full-length human J1 was purchased from SourceBioscience and the open reading frame sequence was amplified by PCR and directionally cloned into pEGFP-N1 expression vector. Myc-DDK-tagged human J2 full-length expression vector was purchased from Origene Technologies. Human DLL4 and mJ1 were described previously [25]. To express human and murine J1-DSL-EGF3 on cell surface, an expression vector based on pEGFP-N1 was constructed to express an N-terminal-tagged CD1 b molecule (including its α3 domain, the transmembrane region, and the cytoplasmic tail) fused with EGFP at the C-terminus. cDNA sequences encoding human and murine J1-DSL-EGF3 were PCR amplified, and directionally cloned into the above vector. Rabbit and guinea pig J1 amino acid sequences were compared with that of human, and the FLAG-EGFP-tagged human J1 construct was mutated accordingly to generate rabbit (I275T) and guinea pig J1 (R231K, L247I, D250N, I275T, N277I) constructs. The FLAG-EGFP-tagged murine J1 construct was mutated to generate the rat construct (D228E).

FACS Analysis with Anti-J1 Antibody

HEK293 cells transfected with human J1, J2 or FLAG-EGFP-tagged DSL-EGF3 constructs, B16F10 cells transfected with human DLL4 or mouse J1, and human cancer cell lines, were stained with either purified anti-J1 antibodies at 10 μg/ml diluted in FACS wash buffer (2% FBS in PBS+0.1% sodium azide) or neat hybridoma supernatants followed by a allophycocyanin (APC)-conjugated secondary antibody at 1:200 dilution: for murine primary antibodies, used goat anti-mouse-APC (eBioscience); for humanised and chimeric antibodies used goat anti-human IgG (H+L) secondary antibody (Jackson ImmunoResearch Laboratories). After washing, samples were fixed with 1% paraformaldehyde (in PBS) and acquired with a FACSCalibur. FACS data were analysed with FlowJo software (TreeStar Inc.). On some occasions APC-conjugated J1-65D and J1-183D antibodies were used (eg FIG. 4E).

Immunostaining Analysis of Anti-J1 Antibodies

Acetone fixed cytospin cell preparations of J1 and J2 HEK293 transfectants were incubated with the undiluted hybridoma supernatant for 30 min at RT. J2 monoclonal antibody MHJ2-523 (Biologend) was used as a positive control for J2 staining at a 1:50 dilution. After two washes in PBS, the slides were incubated with 1:50 dilution of polyclonal goat anti-mouse Immunoglobulins/HRP antibody (Dako, P0447) for 30 min at RT. The polyclonal rabbit anti-goat Immunoglobulins/HRP antibody (Dako, P0449) was used for the J1 goat polyclonal antibody stained slide at a 1:25 dilution. After two washes in PBS, the colour reaction was developed using REAL Envision Detection System, Peroxidase/DAB+, Rabbit/Mouse kit (Dako, K5007). The slides were washed and counterstained in Harris haematoxylin before mounting in Aquatex Mounting Agent (BDH/VWR, 63123S).

Immunohistochemistry

In brief, paraffin-embedded spheroid sections were de-waxed and subjected to heat-induced antigen retrieval under pressure in a microwave oven at 750 W for 10 minutes (citrate pH6 retrieval buffer; Dako). Sections were incubated with the Ki67-specific Ab (M7240; Dako; 1:50) at room temperature for 1 hour. Bound Ab was detected using the Envision system (DAKOCytomation, Ely, Cambridgeshire, UK), visualized by using 2, 3-diaminobenzidine chromogen and counterstained with hematoxylin.

Notch Binding Blocking Assay

Human N1 EGF11-13 (411-526) was expressed in E. coli, refolded in vitro and labelled with purple fluorescent avidin-coated beads (Spherotech) as previously described [74]. HEK293 cells transfected with human J1 or B16F10 cells transfected with mouse J1 were stained with N1 fluorescent beads in the presence of J1 antibody supernatants or purified antibody (murine, chimeric or humanised) diluted in HBBS/ 10% FCS. Cells were washed and re-suspended in staining buffer before being analysed with a FACSCalibur and data analysis with CellQuest. HEK293 cells transfected with human Jagged 2 and B16F10 cells transfected with human and mouse DLL4 were stained similarly to test blocking specificity.

CD46 Binding Blocking Assay

A 96-well MaxiSorp plate was coated with CD46 (CCP1-CCP3) at a concentration of 5 µg/ml in Tris buffered saline and incubated at 4° C. overnight. The plate was blocked at 4° C. in 20 mM HEPES, pH 7.4, 1% BSA overnight. It was then incubated for 2 h at room temperature in ELISA buffer: 20 mM HEPES pH 7.4, 10 mM $CaCl_2$, 0.005% Tween 20, 0.25% NP40, 4% BSA containing biotinylated J1 DSL-EGF3 (0.5 µg/ml) in the absence or presence of a 1:10 dilution of each hybridoma supernatant. After 5 washes with ELISA buffer the plate was incubated with 1:1000 dilution of Neutravidin HRP conjugate (Invitrogen). The plate was washed 6 times and developed with 2,2'-Azino-bis(3-ethylbenzothiazoline-6-sulfonic acid) diammonium salt (Sigma-Aldrich).

Antibody Binding Blocking Assay

Purified J1 mAbs were biotinylated using an EZ-link Micro Sulfo-NHS-Biotinylation kit (Fisher Scientific) according to manufacturer's manual. Biotinylated mAbs were used to stain HEK293 cells stably transfected with J1 at 1.0 µg/ml in the presence of non-biotinylated J1 mAbs at various concentrations for 20 min at 4° C. After washing Streptavidin-PE (Sigma-Aldrich, 1:200) was used to detect biotinylated J1 mAb staining and incubated for 20 min at 4° C. in dark. The samples were then washed, fixed with 1% paraformaldehyde before analysis with a FACSCalibur. FACS data was analysed with Flowjo software (TreeStar, California).

Surface Plasmon Resonance

Binding affinities of murine J1 mAbs towards different forms of J1 soluble protein were tested with a BIACore T-3000. J1 mAbs were immobilised through primary amine coupling to the chip surface. J1 soluble proteins were passed over the chip in 10 mM HEPES (pH 7.4), 150 mM NaCl, 3 mM EDTA, 0.005% Surfactant P20. Titrations were performed over 0.8 nM to 10 nM concentration range (with 7.8 nM to 100 nM for J1-187B), with a flow rate of 10 µl/min at 25° C.

J1 Stable Cell Line Generation

J1 full-length cDNA was cloned into a retrovirus vector LZRSpBMN-linker-IRES-EGFP. HEK293T cells were transfected with the virus construct and packaging mix and virus particles were harvested at 24, 48 and 72 h post transfection. Virus containing culture supernatants were filtered with 0.45 µm syringe filter units and were applied to target cells MDA-MB-231 and U87. The cells were cultured for 7 days, split and changed medium when needed. GFP high-expressing populations were then FACS sorted and expanded in culture. J1 expression was confirmed to correlate with GFP expression by FACS staining. Empty vector transduced cells were also generated in parallel.

J1 Knockdown

Mission shRNA (sequence CCGGGTGCACCTCT-GACTCCTATTACT CGAGTAATAGGAGTCAGAGGTG-CACTTTTTG (SEQ ID NO. 36)) in lentivirus vector TRC2 was purchased (Sigma-Aldrich) and lentivirus particles were generated by co-transfecting HEK293T cells with packaging plasmids (Invitrogen) and the lentivirus plasmids. Culture supernatants containing virus particles were harvested at 24, 48 and 72 h post-transfection, filtered with 0.45 µm syringe filter units. Virus particles were then applied to target cell MDA-MB-231 and the cells were cultured for 7 days, split and changed medium when needed, before their J1 level of expression was tested by FACS as described above.

Dot Blot Epitope Mapping of J1 mAbs

Missense mutations to generate Y190H, F199A, R201A, R203A, F207A, N215A, E228D and R231K in the J1 DSL-EGF3 construct were introduced into pQE30 recombinant plasmid containing the cDNA sequence of the wild-type construct by PCR-based site-directed mutagenesis with Pfu DNA polymerase. Generation of the desired mutation was confirmed by DNA sequencing. The mutant constructs were purified as described for the wild-type J1 DSL-EGF3 BirA. Masses were confirmed by Electrospray Ionisation Mass Spectral analysis (ESI-MS). Wild-type and mutant constructs were prepared at a concentration suitable for detection and 1 µl spotted on to nitrocellulose. The proteins were detected with diluted hybridoma supernatants or purified mAb at the concentrations given in figure legends followed by anti-mouse HRP conjugate (1:1000) and visualised by chemiluminescence (Amersham ECL Plus Western Blotting Detection System).

Total RNA Extraction, Reverse Transcription and Quantitative Real Time PCR

Total RNA from cell cultures/spheroids was isolated using RNeasy mini kit (Qiagen, UK) according to the manufacturer's instructions. Complementary DNA (cDNA) was synthesized from 0.5-1 µg of total RNA using Superscript III first-strand system (Invitrogen). Quantitative PCR (qPCR) analysis was performed in triplicate using the SYBR GreenER qPCR SuperMix Universal (Invitrogen) and Chromo4 fluorescence detector (MJ Research, USA). Relative quantification was done using the ΔΔCt method normalizing to β2-microglobulin gene or murine β-Actin expression. For primer sequences see following Table.

| Gene | Primer sequence |
|---|---|
| Human β2-microglobulin | forward 5'-TGCTGTCTCCATGTTTGATGTATCT-3' (SEQ ID NO. 37) reverse 5'-TCTCTGCTCCCCACCTCTAAGT-3' (SEQ ID NO. 38) |
| Human HES1 (used for in vitro samples) | forward 5'-GCTGGAGAAGGCGGACATTC-3' (SEQ ID NO. 39) reverse 5'-AAGCGGGTCACCTCGTTCAT-3' (SEQ ID NO. 40) |

-continued

| Gene | Primer sequence |
|---|---|
| Human HES1 (used for in vivo samples) | forward 5'-TGCTCTGAAGAAAGATAGCTCG-3' (SEQ ID NO. 41) reverse 5'-CGGAGGTGCTTCACTGTCAT-3' (SEQ ID NO. 42) |
| Human IL6 | forward 5'-AGTGAGGAACAAGCCAGAGC-3' (SEQ ID NO. 43) reverse 5'-GGCATTGTGGTTGGGTCAG-3' (SEQ ID NO. 44) |
| Human E-cadherin | forward 5'-CCCACCACGTACAAGGGTC-3' (SEQ ID NO. 45) reverse 5'-CTGGGGTATTGGGGGCATC-3' (SEQ ID NO. 46) |
| Human PRRX1 | forward 5'-CTGATGCTTTTGTGCGAGAA-3' (SEQ ID NO. 47) reverse 5'-ACTTGGCTCTTCGGTTCTGA-3' (SEQ ID NO. 48) |
| Murine β-Actin | forward 5'-CTAAGGCCAACCGTGAAAAG-3' (SEQ ID NO. 49) reverse 5'-ACCAGAGGCATACAGGGACA-3' (SEQ ID NO. 50) |
| Murine Hes1 | forward 5'-AAAGCCTATCATGGAGAAGAGG-3' (SEQ ID NO. 51) reverse 5'-TGCCGGGAGCTATCTTTCTT-3' (SEQ ID NO. 52) |
| Murine Hey2 | forward 5'-GTGGGGAGCGAGAACAATTA-3' (SEQ ID NO. 53) reverse 5'-GTTGTCGGTGAATTGGACCT-3' (SEQ ID NO. 54) |
| Murine Gapdh | forward 5'-ATGGTGAAGGTCGGTGTGA-3' (SEQ ID NO. 55) reverse 5'-AATCTCCACTTTGCCACTGC-3' (SEQ ID NO. 56) |

Luciferase Assay

Prior to experiment, clear bottom 96-well plates (CELL-STAR) wells were coated with either J1-ECD fragments (NE3-Fc and NE12-Fc), other Notch-ligands (J2 or DLL4; both from R&D) or control protein (mIgG2b) at the concentration of 5 µg/ml in 0.1% BSA-PBS (overnight incubation at 4° C.). LS174T colorectal cancer cells, expressing the luciferase gene under control of the Notch cofactor RbPJ, were then plated ($4 \times 10^4$ cells/well) in the presence of different mAbs (10 µg/ml) or DBZ (100 nM). Luciferase activity was then quantified 24 hours later using the Bright-Glo Luciferase Assay System (Promega).

Spheroid Assay

Cells were harvested and resuspended in 2.5% Matrigel (BD)-complete DMEM medium. Cell suspension was plated on low-adherence 96-well plates (Corning) (200 µl/well) and spheroids, of approximately fixed cell number ($5 \times 10^3$ cells for MDA-MB-231 and MDA-MB-468 cell lines; $2 \times 10^3$ for MCF7 cells) were then generated by spinning plates at 1800 rpm for 10 minutes. The following day, pictures of the spheroids were taken (day 1) and treatments were added (mAbs were used at 10 µg/ml [5 µg/ml for humanised antibodies] while DBZ was used at the concentration of 100 nM). In some experiments Paclitaxel (1 nM) and Doxorubicin (20 nM) were used in combination with J1-65D mAb treatment. Every 2 days pictures were taken and half of the medium was replaced with fresh one containing mAb/drug. At the end of the experiment, spheroids were either lysed for RNA extraction, were processed and paraffin-embedded for immunohistochemical analysis or were dissociated by pipetting and trypsinization into single cell suspensions for FACS analysis. Spheroid size was evaluated by image analysis using ImageJ software.

Cancer Stem Cell Quantification

After spheroid dissociation, cells were either analysed for CD44-CD24 surface expression (a combination of markers able to identify a cancer stem cell-enriched population in MDA-MB-231 cell line [75]) or for aldehyde dehydrogenase 1 activity (a more general approach to identify stem cells [76]). For CD44-CD24 analysis, cells were stained with a phycoerythrin (PE)-conjugated anti-human CD44 antibody (Clone 2C5; R&D Systems) according to manufacturer's guidelines. After washing, samples were fixed with 1% paraformaldehyde (in PBS) and acquired with a FACSCalibur. For aldehyde dehydrogenase 1 activity, cells were prepared and analysed as for manufacturer's protocol (ALDEFLUOR™ Kit; STEMCELL Technologies).

J1 Stable Cell Line Co-Culture Experiment

J1- or vector-transduced MDA-MB-231 and U87 cells were co-cultured with their parental cells in a 6 well plate for 5 weeks. Cells were split twice every week and GFP positive populations (representing transduced cells) were measured by FACS after every split.

Xenograft Experiments

MDA-MB-231 cells ($1 \times 10^7$) or U87 stable cell lines ($1 \times 10^7$ vector or human J1 transduced) in 100 µl Matrigel were injected subcutaneously into the flank of BALB/c nu/nu mice. J1 blocking mAbs, control IgG1 mAb, at the indicated concentrations, or PBS of equal volume were injected at the same time intraperitoneally as tumour grafting and every 3 or 4 days afterwards. Tumour dimensions were measured and tumour volume was calculated as L×W×H×π/6 as described [77]. Geometric Mean Diameter (GMD) was calculated as $(L \times W \times H)^{1/3}$.

J1 mAb Humanisation and Deimmunisation

J1 mAbs (J1-65D and J1-183D) were humanised and deimmunised by Lonza Biologics. Briefly, In silico humanisation and deimmunisation were performed on both mAb sequences using CDR grafting technology and T-cell epitope reduction. Heavy chain and light chain variable region cDNAs were synthesised and cloned into expression vectors encoding human IgG1 framework. In total 16 variants were generated for each mAb. Transient transfection was performed in CHOK1SV GS-KO cells and humanised antibodies were purified from 200 ml culture supernatants via Protein A chromatography.

SEQ IDs:

| | |
|---|---|
| RASGNIHNYLA | SEQ ID NO: 1 |
| NAKTLADDI | SEQ ID NO: 2 |
| QHFWSAPWT | SEQ ID NO: 3 |
| DYEMH | SEQ ID NO: 4 |
| QPGGGGTAYNQKFKG | SEQ ID NO: 5 |
| RGYDDYPFAY | SEQ ID NO: 6 |
| KSSQSLLNSSNQKNYLA | SEQ ID NO: 7 |
| FASTRESGV | SEQ ID NO: 8 |
| QQHYSTPYT | SEQ ID NO: 9 |
| DYAMH | SEQ ID NO: 10 |
| NTYYGDASYNQKFKG | SEQ ID NO: 11 |
| LYDYDGGFAY | SEQ ID NO: 12 |
| RTSENIYSYLT | SEQ ID NO: 13 |
| NAKILAAGV | SEQ ID NO: 14 |
| QHHYDIPWT | SEQ ID NO: 15 |
| DYAIH | SEQ ID NO: 16 |
| NTYYGDSKYNQKFKD | SEQ ID NO: 17 |
| GYDGFAY | SEQ ID NO: 18 |
| RASENIYSYLA | SEQ ID NO: 19 |
| NAKTLAEW | SEQ ID NO: 20 |
| QHHYGTPLT | SEQ ID NO: 21 |
| DYAMH | SEQ ID NO: 22 |
| NTYYGDARYNQKFKG | SEQ ID NO: 23 |
| GLEGFAY | SEQ ID NO: 24 |
| QQHYSTPYT | SEQ ID NO79 |
| NAKTLAEGV | SEQ ID NO: 80 |
| QHHYGTPWT | SEQ ID NO: 81 |

REFERENCES

1. Carmeliet P, Jain R K: Molecular mechanisms and clinical applications of angiogenesis. *Nature* 2011, 473(7347): 298-307.
2. Li J L, Harris A L: Crosstalk of VEGF and Notch pathways in tumour angiogenesis: therapeutic implications. *Front Biosci* 2009, 14:3094-3110.
3. Jain R K, Duda D G, Clark J W, Loeffler J S: Lessons from phase III clinical trials on anti-VEGF therapy for cancer. *Nat Clin Pract Oncol* 2006, 3(1):24-40.
4. Kerbel R S: Tumor angiogenesis. *N Engl J Med* 2008, 358(19):2039-2049.
5. Sainson R C, Harris A L: Regulation of angiogenesis by homotypic and heterotypic notch signalling in endothelial cells and pericytes: from basic research to potential therapies. *Angiogenesis* 2008, 11(1):41-51.
6. Swiatek P J, Lindsell C E, del Amo F F, Weinmaster G, Gridley T: Notch1 is essential for postimplantation development in mice. *Genes Dev* 1994, 8(6):707-719.
7. Hrabe de Angelis M, McIntyre J, 2nd, Gossler A: Maintenance of somite borders in mice requires the Delta homologue DII1. *Nature* 1997, 386(6626):717-721.
8. Xue Y, Gao X, Lindsell C E, Norton C R, Chang B, Hicks C, Gendron-Maguire M, Rand E B, Weinmaster G, Gridley T: Embryonic lethality and vascular defects in mice lacking the Notch ligand Jagged1. *Hum Mol Genet* 1999, 8(5):723-730.
9. Gale N W, Dominguez M G, Noguera I, Pan L, Hughes V, Valenzuela D M, Murphy A J, Adams N C, Lin H C, Holash J et al: Haploinsufficiency of delta-like 4 ligand results in embryonic lethality due to major defects in arterial and vascular development. *Proc Natl Acad Sci USA* 2004, 101(45):15949-15954.
10. Joutel A, Corpechot C, Ducros A, Vahedi K, Chabriat H, Mouton P, Alamowitch S, Domenga V, Cecillion M, Marechal E et al: Notch3 mutations in CADASIL, a hereditary adult-onset condition causing stroke and dementia. *Nature* 1996, 383(6602):707-710.
11. Oda T, Elkahloun A G, Pike B L, Okajima K, Krantz I D, Genin A, Piccoli D A, Meltzer P S, Spinner N B, Collins F S et al: Mutations in the human Jagged1 gene are responsible for Alagille syndrome. *Nat Genet* 1997, 16(3):235-242.
12. Bray S J: Notch signalling: a simple pathway becomes complex. *Nat Rev Mol Cell Biol* 2006, 7(9):678-689.

13. Purow B: Notch inhibition as a promising new approach to cancer therapy. *Adv Exp Med Biol* 2012, 727:305-319.
14. Weng A P, Ferrando A A, Lee W, Morris J Pt, Silverman L B, Sanchez-Irizarry C, Blacklow S C, Look A T, Aster J C: Activating mutations of NOTCH1 in human T cell acute lymphoblastic leukemia. *Science* 2004, 306(5694): 269-271.
15. Fabbri G, Rasi S, Rossi D, Trifonov V, Khiabanian H, Ma J, Grunn A, Fangazio M, Capello D, Monti S et al: Analysis of the chronic lymphocytic leukemia coding genome: role of NOTCH1 mutational activation. *J Exp Med* 2011, 208(7):1389-1401.
16. Puente X S, Pinyol M, Quesada V, Conde L, Ordonez G R, Villamor N, Escaramis G, Jares P, Bea S, Gonzalez-Diaz M et al: Whole-genome sequencing identifies recurrent mutations in chronic lymphocytic leukaemia. *Nature* 2011, 475(7354):101-105.
17. Kridel R, Meissner B, Rogic S, Boyle M, Telenius A, Woolcock B, Gunawardana J, Jenkins C, Cochrane C, Ben-Neriah S et al: Whole transcriptome sequencing reveals recurrent NOTCH1 mutations in mantle cell lymphoma. *Blood* 2012, 119(9):1963-1971.
18. Lee S Y, Kumano K, Nakazaki K, Sanada M, Matsumoto A, Yamamoto G, Nannya Y, Suzuki R, Ota S, Ota Y et al: Gain-of-function mutations and copy number increases of Notch2 in diffuse large B-cell lymphoma. *Cancer Sci* 2009, 100(5):920-926.
19. Shi W, Harris A L: Notch signaling in breast cancer and tumor angiogenesis: cross-talk and therapeutic potentials. *J Mammary Gland Biol Neoplasia* 2006, 11(1):41-52.
20. Lobry C, Oh P, Aifantis I: Oncogenic and tumor suppressor functions of Notch in cancer: it's NOTCH what you think. *J Exp Med* 2011, 208(10):1931-1935.
21. Ranganathan P, Weaver K L, Capobianco A J: Notch signalling in solid tumours: a little bit of everything but not all the time. *Nat Rev Cancer* 2011, 11(5):338-351.
22. Li K, Li Y, Wu W, Gordon W R, Chang D W, Lu M, Scoggin S, Fu T, Vien L, Histen G et al: Modulation of Notch signaling by antibodies specific for the extracellular negative regulatory region of NOTCH3. *J Biol Chem* 2008, 283(12):8046-8054.
23. Wu Y, Cain-Horn C, Choy L, Hagenbeek T J, de Leon G P, Chen Y, Finkle D, Venook R, Wu X, Ridgway J et al: Therapeutic antibody targeting of individual Notch receptors. *Nature* 2010, 464(7291):1052-1057.
24. Pellegrinet L, Rodilla V, Liu Z, Chen S, Koch U, Espinosa L, Kaestner K H, Kopan R, Lewis J, Radtke F: Dll1- and dll4-mediated notch signaling are required for homeostasis of intestinal stem cells. *Gastroenterology* 2011, 140(4):1230-1240 e1231-1237.
25. Li J L, Sainson R C, Shi W, Leek R, Harrington L S, Preusser M, Biswas S, Turley H, Heikamp E, Hainfellner J A et al: Delta-like 4 Notch ligand regulates tumor angiogenesis, improves tumor vascular function, and promotes tumor growth in vivo. *Cancer Res* 2007, 67(23): 11244-11253.
26. Noguera-Troise I, Daly C, Papadopoulos N J, Coetzee S, Boland P, Gale N W, Lin H C, Yancopoulos G D, Thurston G: Blockade of Dll4 inhibits tumour growth by promoting non-productive angiogenesis. *Nature* 2006, 444(7122): 1032-1037.
27. Ridgway J, Zhang G, Wu Y, Stawicki S, Liang W C, Chanthery Y, Kowalski J, Watts R J, Callahan C, Kasman I et al: Inhibition of Dll4 signalling inhibits tumour growth by deregulating angiogenesis. *Nature* 2006, 444 (7122):1083-1087.
28. Scehnet J S, Jiang W, Kumar S R, Krasnoperov V, Trindade A, Benedito R, Djokovic D, Borges C, Ley E J, Duarte A et al: Inhibition of Dll4-mediated signaling induces proliferation of immature vessels and results in poor tissue perfusion. *Blood* 2007, 109(11):4753-4760.
29. Harrington L S, Sainson R C, Williams C K, Taylor J M, Shi W, Li J L, Harris A L: Regulation of multiple angiogenic pathways by Dll4 and Notch in human umbilical vein endothelial cells. *Microvasc Res* 2008, 75(2):144-154.
30. Reedijk M, Odorcic S, Chang L, Zhang H, Miller N, McCready D R, Lockwood G, Egan S E: High-level coexpression of JAG1 and NOTCH1 is observed in human breast cancer and is associated with poor overall survival. *Cancer Res* 2005, 65(18):8530-8537.
31. Hellstrom M, Phng L K, Hofmann J J, Wallgard E, Coultas L, Lindblom P, Alva J, Nilsson A K, Karlsson L, Gaiano N et al: Dll4 signalling through Notch1 regulates formation of tip cells during angiogenesis. *Nature* 2007, 445(7129):776-780.
32. Limbourg F P, Takeshita K, Radtke F, Bronson R T, Chin M T, Liao J K: Essential role of endothelial Notch1 in angiogenesis. *Circulation* 2005, 111(14):1826-1832.
33. Benjamin L E, Hemo I, Keshet E: A plasticity window for blood vessel remodelling is defined by pericyte coverage of the preformed endothelial network and is regulated by PDGF-B and VEGF. *Development* 1998, 125(9): 1591-1598.
34. Bergers G, Song S, Meyer-Morse N, Bergsland E, Hanahan D: Benefits of targeting both pericytes and endothelial cells in the tumor vasculature with kinase inhibitors. *J Clin Invest* 2003, 111(9):1287-1295.
35. Erber R, Thurnher A, Katsen A D, Groth G, Kerger H, Hammes H P, Menger M D, Ullrich A, Vajkoczy P: Combined inhibition of VEGF and PDGF signaling enforces tumor vessel regression by interfering with pericyte-mediated endothelial cell survival mechanisms. *FASEB J* 2004, 18(2):338-340.
36. High F A, Lu M M, Pear W S, Loomes K M, Kaestner K H, Epstein J A: Endothelial expression of the Notch ligand Jagged1 is required for vascular smooth muscle development. *Proc Natl Acad Sci USA* 2008, 105(6): 1955-1959.
37. Msaouel P, Dispenzieri A, Galanis E: Clinical testing of engineered oncolytic measles virus strains in the treatment of cancer: an overview. *Curr Opin Mol Ther* 2009, 11(1):43-53.
38. Anderson B D, Nakamura T, Russell S J, Peng K W: High CD46 receptor density determines preferential killing of tumor cells by oncolytic measles virus. *Cancer Res* 2004, 64(14):4919-4926.
39. McDonald C J, Erlichman C, Ingle J N, Rosales G A, Allen C, Greiner S M, Harvey M E, Zollman P J, Russell S J, Galanis E: A measles virus vaccine strain derivative as a novel oncolytic agent against breast cancer. *Breast cancer research and treatment* 2006, 99(2):177-184.
40. Studebaker A W, Kreofsky C R, Pierson C R, Russell S J, Galanis E, Raffel C: Treatment of medulloblastoma with a modified measles virus. *Neuro Oncol* 2010, 12(10): 1034-1042.
41. Nandi S, Ulasov I V, Rolle C E, Han Y, Lesniak M S: A chimeric adenovirus with an Ad 3 fiber knob modification augments glioma virotherapy. *J Gene Med* 2009, 11(11): 1005-1011.
42. Galanis E, Hartmann L C, Cliby W A, Long H J, Peethambaram P P, Barrette B A, Kaur J S, Haluska P J, Jr., Aderca I, Zollman P J et al: Phase I trial of intraperitoneal administration of an oncolytic measles virus strain engineered to express carcinoembryonic antigen for recurrent ovarian cancer. *Cancer Res* 2010, 70(3):875-882.
43. Wang Y, Ma L, Wang S, Bao Y, Ni C, Guan N, Zhao J, Fan X: Assessment of CAR– or CD46-dependent adenoviral vector-mediated TRAIL gene therapy in clinical adenocarcinoma lung cancer cells. *Oncology* 2009, 77(6):366-377.
44. Msaouel P, Iankov I D, Allen C, Aderca I, Federspiel M J, Tindall D J, Morris J C, Koutsilieris M, Russell S J, Galanis E: Noninvasive imaging and radiovirotherapy of prostate cancer using an oncolytic measles virus expressing the sodium iodide symporter. *Mol Ther* 2009, 17(12):2041-2048.
45. Le Friec G, Sheppard D, Whiteman P, Karsten C M, Shamoun S A, Laing A, Bugeon L, Daliman M J, Melchionna T, Chillakuri C et al: The CD46-Jagged1 interaction is critical for human T(H)1 immunity. *Nat Immunol* 2012.
46. Kolev M, Towner L, Donev R: Complement in cancer and cancer immunotherapy. *Arch Immunol Ther Exp (Warsz)* 2011, 59(6):407-419.
47. Gancz D, Fishelson Z: Cancer resistance to complement-dependent cytotoxicity (CDC): Problem-oriented research and development. *Mol Immunol* 2009, 46(14):2794-2800.
48. Varela J C, Atkinson C, Woolson R, Keane T E, Tomlinson S: Upregulated expression of complement inhibitory proteins on bladder cancer cells and anti-MUC1 antibody immune selection. *Int J Cancer* 2008, 123(6):1357-1363.
49. Ravindranath N M, Shuler C: Expression of complement restriction factors (CD46, CD55 & CD59) in head and neck squamous cell carcinomas. *J Oral Pathol Med* 2006, 35(9):560-567.
50. Ong H T, Timm M M, Greipp P R, Witzig T E, Dispenzieri A, Russell S J, Peng K W: Oncolytic measles virus targets high CD46 expression on multiple myeloma cells. *Exp Hematol* 2006, 34(6):713-720.
51. Lee C N, Heidbrink J L, McKinnon K, Bushman V, Olsen H, FitzHugh W, Li A, Van Orden K, He T, Ruben S M et al: RNA interference characterization of proteins discovered by proteomic analysis of pancreatic cancer reveals function in cell growth and survival. *Pancreas* 2012, 41(1):84-94.
52. Maciejczyk A, Szelachowska J, Szynglarewicz B, Szulc R, Szulc A, Wysocka T, Jagoda E, Lage H, Surowiak P: CD46 Expression is an unfavorable prognostic factor in breast cancer cases. *Appl Immunohistochem Mol Morphol* 2011, 19(6):540-546.
53. Surowiak P, Materna V, Maciejczyk A, Kaplenko I, Spaczynski M, Dietel M, Lage H, Zabel M: CD46 expression is indicative of shorter revival-free survival for ovarian cancer patients. *Anticancer Res* 2006, 26(6C):4943-4948.
54. Cui W, Zhang Y, Hu N, Shan C, Zhang S, Zhang W, Zhang X, Ye L: miRNA-520b and miR-520e sensitize breast cancer cells to complement attack via directly targeting 3'UTR of CD46. *Cancer Biol Ther* 2010, 10(3):232-241.
55. Geis N, Zell S, Rutz R, Li W, Giese T, Mamidi S, Schultz S, Kirschfink M: Inhibition of membrane complement inhibitor expression (CD46, CD55, CD59) by siRNA sensitizes tumor cells to complement attack in vitro. *Curr Cancer Drug Targets* 2010, 10(8):922-931.
56. Gao L J, Guo S Y, Cai Y Q, Gu P Q, Su Y J, Gong H, Liu Y, Chen C: Cooperation of decay-accelerating factor and membrane cofactor protein in regulating survival of human cervical cancer cells. *BMC Cancer* 2009, 9:384.
57. Zell S, Geis N, Rutz R, Schultz S, Giese T, Kirschfink M: Down-regulation of CD55 and CD46 expression by anti-sense phosphorothioate oligonucleotides (S-ODNs) sensitizes tumour cells to complement attack. *Clin Exp Immunol* 2007, 150(3):576-584.
58. Sethi N, Dai X, Winter C G, Kang Y: Tumor-derived JAGGED1 promotes osteolytic bone metastasis of breast cancer by engaging notch signaling in bone cells. *Cancer Cell* 2011, 19(2):192-205.
59. Jundt F, Probsting K S, Anagnostopoulos I, Muehlinghaus G, Chatterjee M, Mathas S, Bargou R C, Manz R, Stein H, Dorken B: Jagged1-induced Notch signaling drives proliferation of multiple myeloma cells. *Blood* 2004, 103(9):3511-3515.
60. Perry A M, Cardesa-Salzmann T M, Meyer P N, Colomo L, Smith L M, Fu K, Greiner T C, Delabie J, Gascoyne R D, Rimsza L et al: A new biologic prognostic model based on immunohistochemistry predicts survival in patients with diffuse large B-cell lymphoma. *Blood* 2012, 120(11):2290-2296.
61. Lenz G, Wright G, Dave S S, Xiao W, Powell J, Zhao H, Xu W, Tan B, Goldschmidt N, Iqbal J et al: Stromal gene signatures in large-B-cell lymphomas. *N Engl J Med* 2008, 359(22):2313-2323.
62. Cardesa-Salzmann T M, Colomo L, Gutierrez G, Chan W C, Weisenburger D, Climent F, Gonzalez-Barca E, Mercadal S, Arenillas L, Serrano S et al: High microvessel density determines a poor outcome in patients with diffuse large B-cell lymphoma treated with rituximab plus chemotherapy. *Haematologica* 2011, 96(7):996-1001.
63. Stopeck A T, Unger J M, Rimsza L M, LeBlanc M, Farnsworth B, Iannone M, Glenn M J, Fisher R I, Miller T P: A phase 2 trial of standard-dose cyclophosphamide, doxorubicin, vincristine, prednisone (CHOP) and rituximab plus bevacizumab for patients with newly diagnosed diffuse large B-cell non-Hodgkin lymphoma: SWOG 0515. *Blood* 2012, 120(6):1210-1217.
64. Stopeck A T, Unger J M, Rimsza L M, Bellamy W T, Iannone M, Persky D O, Leblanc M, Fisher R I, Miller T P: A phase II trial of single agent bevacizumab in patients with relapsed, aggressive non-Hodgkin lymphoma: Southwest oncology group study S0108. *Leuk Lymphoma* 2009, 50(5):728-735.
65. Cordle J, Johnson S, Tay J Z, Roversi P, Wilkin M B, de Madrid B H, Shimizu H, Jensen S, Whiteman P, Jin B et al: A conserved face of the Jagged/Serrate DSL domain is involved in Notch trans-activation and cis-inhibition. *Nat Struct Mol Biol* 2008, 15(8):849-857.
66. Aste-Amezaga M, Zhang N, Lineberger J E, Arnold B A, Toner T J, Gu M, Huang L, Vitelli S, Vo K T, Haytko P et al: Characterization of Notch1 antibodies that inhibit signaling of both normal and mutated Notch1 receptors. *PLoS One* 2010, 5(2):e9094.
67. Knupfer H, Preiss R: Significance of interleukin-6 (IL-6) in breast cancer (review). *Breast cancer research and treatment* 2007, 102(2):129-135.
68. Korkaya H, Kim G I, Davis A, Malik F, Henry N L, Ithimakin S, Quraishi A A, Tawakkol N, D'Angelo R, Paulson A K et al: Activation of an IL6 Inflammatory Loop Mediates Trastuzumab Resistance in HER2+ Breast Cancer by Expanding the Cancer Stem Cell Population. *Molecular cell* 2012.

69. Robertson N, Potter C, Harris A L: Role of carbonic anhydrase IX in human tumor cell growth, survival, and invasion. *Cancer research* 2004, 64(17):6160-6165.
70. Winum J Y, Scozzafava A, Montero J L, Supuran C T: Inhibition of carbonic anhydrase IX: a new strategy against cancer. *Anti-cancer agents in medicinal chemistry* 2009, 9(6):693-702.
71. Kang Y, Massague J: Epithelial-mesenchymal transitions: twist in development and metastasis. *Cell* 2004, 118(3):277-279.
72. Moreno-Bueno G, Portillo F, Cano A: Transcriptional regulation of cell polarity in EMT and cancer. *Oncogene* 2008, 27(55):6958-6969.
73. Ocana O H, Corcoles R, Fabra A, Moreno-Bueno G, Acloque H, Vega S, Barrallo-Gimeno A, Cano A, Nieto M A: Metastatic colonization requires the repression of the epithelial-mesenchymal transition inducer Prrx1. *Cancer cell* 2012, 22(6):709-724.
74. Cordle J, Redfieldz C, Stacey M, van der Merwe P A, Willis A C, Champion B R, Hambleton S, Handford P A: Localization of the delta-like-1-binding site in human Notch-1 and its modulation by calcium affinity. *J Biol Chem* 2008, 283(17):11785-11793.
75. Marotta L L, Almendro V, Marusyk A, Shipitsin M, Schemme J, Walker S R, Bloushtain-Qimron N, Kim J J, Choudhury S A, Maruyama R at al: The JAK2/STAT3 signaling pathway is required for growth of CD44(+)CD24(−) stem cell-like breast cancer cells in human tumors. *The Journal of clinical investigation* 2011, 121(7):2723-2735.
76. Yu F, Li J, Chen H, Fu J, Ray S, Huang S, Zheng H, Ai W: Kruppel-like factor 4 (KLF4) is required for maintenance of breast cancer stem cells and for cell migration and invasion. *Oncogene* 2011, 30(18):2161-2172.
77. Tomayko M M, Reynolds C P: Determination of subcutaneous tumor size in athymic (nude) mice. Cancer Chemother Pharmacol 1989, 24(3):148-154.
78. Al-Lazikani B., Lesk A. M., Chothia C. (1997). Standard conformations for the canonical structures of immunoglobulins. *J Mol Biol.* 273. 927-948.
79. Kabat et al., *J. Immunol.,* 1991; 147(5): 1709-1719.
80. Facciabene A, Motz G T, Coukos G: T-regulatory cells: key players in tumor immune escape and angiogenesis. *Cancer Research* 2012 72(9): 2162-2171.
81. Oleinika K, Nibbs R J, Graham G J, Fraser A R: Suppression, subversion and escape: the role of regulatory T cells in cancer progression. *Clin Exp Immunol* 2013 171(1): 36-45.
82. Vigouroux S, Yvon E, Wagner H J, Biagi E, Dotti G, Sili U, Lira C, Rooney C M, Brenner M K: Induction of antigen-specific regulatory T cells following overexpression of a Notch ligand by human B lymphocytes. *J Virol* 2003 77(20): 10872-10880.
83. Asano N, Watanabe T, Kitani A, Fuss I J, Strober W: Notch1 signaling and regulatory T cell function. *J Immunol* 2008 180(5): 2796-2804.
84. Hue S, Kared H, Mehwish Y, Mouhamad S, Balbo M, Levy Y: Notch activation on effector T cells increases their sensitivity to Treg cell-mediated suppression through upregulation of TGF-βRII expression. *Eur J Immunol* 2012 42(7): 1796-1803.
85. Branford S, Rudzki Z, Walsh S, Grigg A, Arthur C, Taylor K, Herrmann R, Lynch K P, Hughes T P: High frequency of point mutations clustered within the adenosine triphosphate-binding region of BCR/ABL in patients with chronic myeloid leukemia or Ph-positive acute lymphoblastic leukemia who develop imatinib (STI571) resistance. *Blood* 2002 99(9): 3472-3475.
86. Kop E N, Kwakkenbos M J, Teske G J, Kraan M C, Smeets T J, Stacey M, Lin H H, Tak P P, Hamann J: Identification of the epidermal growth factor-TM7 receptor EMR2 and its ligand dermatan sulfate in rheumatoid synovial tissue. *Arthritis Rheum* 2005 52(2): 442-450.
87. Zack et al., *Mol. Immunol.,* 1995; 32 (17-18): 1345-53
88. Samaranayake et al., *Ann. Med.,* 2009; 41(5): 322-31.
89. Fang et al., *Mol. Ther.,* 2007; 15(6):1153-9.

---

The invention claimed is:

1. An antibody which specifically recognises an epitope comprising a portion of the Delta/Serrate/LAG-2 sequence (DSL) domain of human Jagged 1 and blocks the interaction between human Jagged 1 and any receptor selected from the group consisting of Notch and CD46; wherein said portion of the DSL domain of human Jagged 1 comprises the residue E228, and wherein said antibody comprises a CDR-L1, CDR-L2 and CDR-L3 having the amino acid sequence of SEQ ID NO: 1, 27 and 3 respectively; and a CDR-H1, CDR-H2 and CDR-H3 having the amino acid sequence of SEQ ID NO: 4, 5 and 6 respectively.

2. The antibody according to claim 1, wherein said antibody blocks the interaction between human Jagged 1 and a receptor selected from the group consisting of human Notch 1, human Notch 2, human Notch 3, human Notch 4, mouse Notch 1, mouse Notch 2, mouse Notch 3, mouse Notch 4 and human CD46.

3. The antibody according to claim 1, wherein said antibody does not specifically recognise human Delta-like ligand 4.

4. The antibody according to claim 1, wherein said antibody does not block the interaction between human Delta-like ligand 4 and Notch.

5. The antibody according to claim 1, wherein said antibody does not specifically recognise human Jagged 2.

6. The antibody according to claim 1, wherein said antibody does not block the interaction between human Jagged 2 and Notch.

7. The antibody according to claim 1, wherein said antibody does not block the interaction between mouse Jagged 1 and any receptor selected from the group consisting of Notch and CD46.

8. A pharmaceutical composition comprising an antibody according to claim 1 and a pharmaceutically acceptable diluent, excipient, adjuvant, and/or at least one additional therapeutic agent.

9. A method for treating tumor/cancer in a subject in need thereof, the method comprising administering to said subject an antibody according to claim 1, such that said tumor/cancer in said subject is treated, wherein said tumor/cancer is selected from the group consisting of leukemia, myeloma, breast cancer, lymphoma, colorectal cancer, prostate cancer, ovarian cancer, liver cancer and lung cancer.

10. The method according to claim 9, further comprising administering to said subject at least one chemotherapeutic agent, radiotherapy, at least one additional antibody and/or at least one cytokine, or a combination thereof.

11. A hybridoma comprising and/or secreting an antibody according to claim 1.

12. A cell or cell line expressing an antibody according to claim 1 in recombinant form.

13. A recombinant expression vector capable of expressing an antibody according to claim 1.

14. The antibody of claim 4, wherein said antibody does not block the interaction between human Delta-like ligand 4 and any receptor selected from the group consisting of human Notch 1, human Notch 2, human Notch 3, human Notch 4, mouse Notch 1, mouse Notch 2, mouse Notch 3 and mouse Notch 4.

15. The antibody according to claim 6, wherein said antibody does not block the interaction between human Jagged 2 and any receptor selected from the group consisting of human Notch 1, human Notch 2, human Notch 3, human Notch 4, mouse Notch 1, mouse Notch 2, mouse Notch 3 and mouse Notch 4.

16. The antibody according to claim 7, wherein said antibody does not block the interaction between mouse Jagged 1 and any receptor selected from the group consisting of human Notch 1, human Notch 2, human Notch 3, human Notch 4, mouse Notch 1, mouse Notch 2, mouse Notch 3, mouse Notch 4 and human CD46.

17. The antibody of claim 1 comprising a light chain variable domain ($V_L$) and heavy chain variable domain ($V_H$) having the sequence of:
SEQ ID NO: 70 and 73 respectively.

* * * * *

SEQUENCE LISTING

```
<160> NUMBER OF SEQ ID NOS: 98

<210> SEQ ID NO 1
<211> LENGTH: 11
<212> TYPE: PRT
<213> ORGANISM: Homo sapiens

<400> SEQUENCE: 1

Arg Ala Ser Gly Asn Ile His Asn Tyr Leu Ala
1               5                   10

<210> SEQ ID NO 2
<211> LENGTH: 9
<212> TYPE: PRT
<213> ORGANISM: Homo sapiens

<400> SEQUENCE: 2

Asn Ala Lys Thr Leu Ala Asp Asp Ile
1               5

<210> SEQ ID NO 3
<211> LENGTH: 9
<212> TYPE: PRT
<213> ORGANISM: Homo sapiens
```

<400> SEQUENCE: 3

Gln His Phe Trp Ser Ala Pro Trp Thr
1               5

<210> SEQ ID NO 4
<211> LENGTH: 5
<212> TYPE: PRT
<213> ORGANISM: Homo sapiens

<400> SEQUENCE: 4

Asp Tyr Glu Met His
1               5

<210> SEQ ID NO 5
<211> LENGTH: 15
<212> TYPE: PRT
<213> ORGANISM: Homo sapiens

<400> SEQUENCE: 5

Gln Pro Gly Gly Gly Gly Thr Ala Tyr Asn Gln Lys Phe Lys Gly
1               5                   10                  15

<210> SEQ ID NO 6
<211> LENGTH: 10
<212> TYPE: PRT
<213> ORGANISM: Homo sapiens

<400> SEQUENCE: 6

Arg Gly Tyr Asp Asp Tyr Pro Phe Ala Tyr
1               5                   10

<210> SEQ ID NO 7
<211> LENGTH: 17
<212> TYPE: PRT
<213> ORGANISM: Homo sapiens

<400> SEQUENCE: 7

Lys Ser Ser Gln Ser Leu Leu Asn Ser Asn Gln Lys Asn Tyr Leu
1               5                   10                  15

Ala

<210> SEQ ID NO 8
<211> LENGTH: 9
<212> TYPE: PRT
<213> ORGANISM: Homo sapiens

<400> SEQUENCE: 8

Phe Ala Ser Thr Arg Glu Ser Gly Val
1               5

<210> SEQ ID NO 9
<211> LENGTH: 9
<212> TYPE: PRT
<213> ORGANISM: Homo sapiens

<400> SEQUENCE: 9

Gln Gln His Tyr Ser Thr Pro Tyr Thr
1               5

<210> SEQ ID NO 10
<211> LENGTH: 5
<212> TYPE: PRT
<213> ORGANISM: Homo sapiens

```
<400> SEQUENCE: 10

Asp Tyr Ala Met His
1               5

<210> SEQ ID NO 11
<211> LENGTH: 15
<212> TYPE: PRT
<213> ORGANISM: Homo sapiens

<400> SEQUENCE: 11

Asn Thr Tyr Tyr Gly Asp Ala Ser Tyr Asn Gln Lys Phe Lys Gly
1               5                   10                  15

<210> SEQ ID NO 12
<211> LENGTH: 10
<212> TYPE: PRT
<213> ORGANISM: Homo sapiens

<400> SEQUENCE: 12

Leu Tyr Asp Tyr Asp Gly Gly Phe Ala Tyr
1               5                   10

<210> SEQ ID NO 13
<211> LENGTH: 11
<212> TYPE: PRT
<213> ORGANISM: Homo sapiens

<400> SEQUENCE: 13

Arg Thr Ser Glu Asn Ile Tyr Ser Tyr Leu Thr
1               5                   10

<210> SEQ ID NO 14
<211> LENGTH: 9
<212> TYPE: PRT
<213> ORGANISM: Homo sapiens

<400> SEQUENCE: 14

Asn Ala Lys Ile Leu Ala Ala Gly Val
1               5

<210> SEQ ID NO 15
<211> LENGTH: 9
<212> TYPE: PRT
<213> ORGANISM: Homo sapiens

<400> SEQUENCE: 15

Gln His His Tyr Asp Ile Pro Trp Thr
1               5

<210> SEQ ID NO 16
<211> LENGTH: 5
<212> TYPE: PRT
<213> ORGANISM: Homo sapiens

<400> SEQUENCE: 16

Asp Tyr Ala Ile His
1               5

<210> SEQ ID NO 17
<211> LENGTH: 15
<212> TYPE: PRT
<213> ORGANISM: Homo sapiens
```

<400> SEQUENCE: 17

Asn Thr Tyr Tyr Gly Asp Ser Lys Tyr Asn Gln Lys Phe Lys Asp
1               5                   10                  15

<210> SEQ ID NO 18
<211> LENGTH: 7
<212> TYPE: PRT
<213> ORGANISM: Homo sapiens

<400> SEQUENCE: 18

Gly Tyr Asp Gly Phe Ala Tyr
1               5

<210> SEQ ID NO 19
<211> LENGTH: 11
<212> TYPE: PRT
<213> ORGANISM: Homo sapiens

<400> SEQUENCE: 19

Arg Ala Ser Glu Asn Ile Tyr Ser Tyr Leu Ala
1               5                   10

<210> SEQ ID NO 20
<211> LENGTH: 9
<212> TYPE: PRT
<213> ORGANISM: Homo sapiens

<400> SEQUENCE: 20

Asn Ala Lys Thr Leu Ala Glu Val Val
1               5

<210> SEQ ID NO 21
<211> LENGTH: 9
<212> TYPE: PRT
<213> ORGANISM: Homo sapiens

<400> SEQUENCE: 21

Gln His His Tyr Gly Thr Pro Leu Thr
1               5

<210> SEQ ID NO 22
<211> LENGTH: 5
<212> TYPE: PRT
<213> ORGANISM: Homo sapiens

<400> SEQUENCE: 22

Asp Tyr Ala Met His
1               5

<210> SEQ ID NO 23
<211> LENGTH: 15
<212> TYPE: PRT
<213> ORGANISM: Homo sapiens

<400> SEQUENCE: 23

Asn Thr Tyr Tyr Gly Asp Ala Arg Tyr Asn Gln Lys Phe Lys Gly
1               5                   10                  15

<210> SEQ ID NO 24
<211> LENGTH: 7
<212> TYPE: PRT
<213> ORGANISM: Homo sapiens

<400> SEQUENCE: 24

Gly Leu Glu Gly Phe Ala Tyr
1               5

<210> SEQ ID NO 25
<211> LENGTH: 11
<212> TYPE: PRT
<213> ORGANISM: Homo sapiens

<400> SEQUENCE: 25

Arg Ala Ser Gln Gly Ile His Asn Tyr Leu Ala
1               5                   10

<210> SEQ ID NO 26
<211> LENGTH: 9
<212> TYPE: PRT
<213> ORGANISM: Homo sapiens

<400> SEQUENCE: 26

Asn Ala Lys Thr Leu Ala Asp Asp Val
1               5

<210> SEQ ID NO 27
<211> LENGTH: 9
<212> TYPE: PRT
<213> ORGANISM: Homo sapiens

<400> SEQUENCE: 27

Asn Ala Lys Thr Leu Ala Asp Ala Val
1               5

<210> SEQ ID NO 28
<211> LENGTH: 9
<212> TYPE: PRT
<213> ORGANISM: Homo sapiens

<400> SEQUENCE: 28

Gln Gln Phe Trp Ser Ala Pro Trp Thr
1               5

<210> SEQ ID NO 29
<211> LENGTH: 15
<212> TYPE: PRT
<213> ORGANISM: Homo sapiens

<400> SEQUENCE: 29

Gln Pro Gly Gly Gly Gly Thr Ala Tyr Ala Gln Lys Phe Lys Gly
1               5                   10                  15

<210> SEQ ID NO 30
<211> LENGTH: 15
<212> TYPE: PRT
<213> ORGANISM: Homo sapiens

<400> SEQUENCE: 30

Gln Pro Gly Gly Gly Gly Thr Ala Tyr Ala Gln Lys Phe Gln Gly
1               5                   10                  15

<210> SEQ ID NO 31
<211> LENGTH: 9
<212> TYPE: PRT
<213> ORGANISM: Homo sapiens

<400> SEQUENCE: 31

Asn Ala Lys Thr Leu Ala Ser Gly Val
1               5

<210> SEQ ID NO 32
<211> LENGTH: 9
<212> TYPE: PRT
<213> ORGANISM: Homo sapiens

<400> SEQUENCE: 32

Asn Ala Lys Ile Leu Asp Ser Gly Val
1               5

<210> SEQ ID NO 33
<211> LENGTH: 9
<212> TYPE: PRT
<213> ORGANISM: Homo sapiens

<400> SEQUENCE: 33

His Ala Lys Ile Leu Asp Ser Gly Val
1               5

<210> SEQ ID NO 34
<211> LENGTH: 15
<212> TYPE: PRT
<213> ORGANISM: Homo sapiens

<400> SEQUENCE: 34

Asn Thr Tyr Tyr Gly Asp Ser Lys Tyr Ala Gln Lys Phe Gln Gly
1               5                   10                  15

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      reduced peptide derived from DSL

<400> SEQUENCE: 35

Asn Lys Phe Cys Arg Pro Arg Asp Asp Phe Phe Gly His Tyr Ala Cys
1               5                   10                  15

Asp Gln

<210> SEQ ID NO 36
<211> LENGTH: 58
<212> TYPE: DNA
<213> ORGANISM: Artificial Sequence
<220> FEATURE:
<223> OTHER INFORMATION: Description of Artificial Sequence: Synthetic
      Mission shRNA in lentivirus vector TRC2

<400> SEQUENCE: 36
ccgggtgcac ctctgactcc tattactcga gtaataggag tcagaggtgc acttttttg          58

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer sequence for Human beta 2-microglobulin gene

<400> SEQUENCE: 37
tgctgtctcc atgtttgatg tatct                                              25

<210> SEQ ID NO 38
<211> LENGTH: 22

```
<212> TYPE: DNA
<213> ORGANISM: Artificial Sequence
<220> FEATURE:
<223> OTHER INFORMATION: Description of Artificial Sequence: Synthetic
      Reverse primer sequence for Human beta 2-microglobulin gene

<400> SEQUENCE: 38
tctctgctcc ccacctctaa gt                                          22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      Forward primer sequence for human HES1 gene

<400> SEQUENCE: 39
gctggagaag gcggacattc                                             20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      Reverse primer sequence Human HES1 gene

<400> SEQUENCE: 40
aagcgggtca cctcgttcat                                             20

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      Forward primer sequence of Human HES1 gene

<400> SEQUENCE: 41
tgctctgaag aaagatagct cg                                          22

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      Reverse primer sequence of Human HES1 gene

<400> SEQUENCE: 42
cggaggtgct tcactgtcat                                             20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      Forward primer sequence of Human IL6 gene

<400> SEQUENCE: 43
agtgaggaac aagccagagc                                             20

<210> SEQ ID NO 44
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      Reverse primer sequence of Human IL6

<400> SEQUENCE: 44
ggcattgtgg ttgggtcag                                             19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      Forward primer sequence of Human E-cadherin gene

<400> SEQUENCE: 45
cccaccacgt acaagggtc                                             19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      Reverse primer sequence of Human E-cadherin gene

<400> SEQUENCE: 46
ctggggtatt gggggcatc                                             19

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      Forward primer sequence of Human PRRX1 gene

<400> SEQUENCE: 47
ctgatgcttt tgtgcgagaa                                            20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      Reverse primer sequence of Human PRRX1 gene

<400> SEQUENCE: 48
acttggctct tcggttctga                                            20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      Forward primer sequence of Murine Beta-actin gene

<400> SEQUENCE: 49
ctaaggccaa ccgtgaaaag                                            20

<210> SEQ ID NO 50
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      Reverse primer sequence of Murine Beta Actin gene

<400> SEQUENCE: 50
accagaggca tacagggaca                                                  20

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      Forward primer sequence of Murine Hes1 gene

<400> SEQUENCE: 51
aaagcctatc atggagaaga gg                                               22

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      Reverse primer sequence of Murine Hes1 gene

<400> SEQUENCE: 52
tgccgggagc tatctttctt                                                  20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      Forward primer sequence of Murine Hey2 gene

<400> SEQUENCE: 53
gtggggagcg agaacaatta                                                  20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      Reverse primer sequence of Murine Hey2

<400> SEQUENCE: 54
gttgtcggtg aattggacct                                                  20

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      Forward primer sequence of Murine Gapdh gene

<400> SEQUENCE: 55
atggtgaagg tcggtgtga                                                   19

<210> SEQ ID NO 56
<211> LENGTH: 20
<212> TYPE: DNA
<213> ORGANISM: Artificial Sequence
<220> FEATURE:
```

<223> OTHER INFORMATION: Description of Artificial Sequence: Synthetic
      Reverse primer sequence of Murine Gapdh gene

<400> SEQUENCE: 56
aatctccact ttgccactgc                                                    20

<210> SEQ ID NO 57
<211> LENGTH: 129
<212> TYPE: PRT
<213> ORGANISM: Homo sapiens

<400> SEQUENCE: 57

Met Ser Val Pro Thr Gln Val Leu Gly Leu Leu Leu Trp Leu Thr
1               5                   10                  15

Asp Ala Arg Cys Asp Ile Gln Leu Thr Gln Ser Pro Ala Ser Leu Ser
            20                  25                  30

Ala Ser Val Gly Glu Thr Val Thr Phe Thr Cys Arg Thr Ser Glu Asn
        35                  40                  45

Ile Tyr Ser Tyr Leu Thr Trp Tyr Gln Gln Lys Gln Gly Lys Ser Pro
    50                  55                  60

Gln Leu Leu Val Tyr Asn Ala Lys Ile Leu Ala Ala Gly Val Pro Ser
65                  70                  75                  80

Arg Phe Ser Gly Tyr Gly Ser Gly Thr Gln Phe Ser Leu Lys Ile Asn
                85                  90                  95

Ser Leu Gln Pro Glu Asp Phe Gly Thr Tyr Tyr Cys Gln His His Tyr
            100                 105                 110

Asp Ile Pro Trp Thr Phe Gly Gly Gly Thr Lys Leu Glu Ile Lys Arg
        115                 120                 125

Thr

<210> SEQ ID NO 58
<211> LENGTH: 129
<212> TYPE: PRT
<213> ORGANISM: Homo sapiens

<400> SEQUENCE: 58

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Thr Ser Glu Asn
        35                  40                  45

Ile Tyr Ser Tyr Leu Thr Trp Tyr Gln Gln Lys Pro Gly Lys Ala Pro
    50                  55                  60

Lys Leu Leu Val Tyr Asn Ala Lys Ile Leu Ala Ala Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln His His Tyr
            100                 105                 110

Asp Ile Pro Trp Thr Phe Gly Gly Gly Thr Lys Leu Glu Ile Lys Arg
        115                 120                 125

Thr

<210> SEQ ID NO 59
<211> LENGTH: 129
<212> TYPE: PRT

<213> ORGANISM: Homo sapiens

<400> SEQUENCE: 59

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Thr Ser Glu Asn
        35                  40                  45

Ile Tyr Ser Tyr Leu Thr Trp Tyr Gln Gln Lys Pro Gly Lys Ala Pro
    50                  55                  60

Lys Leu Leu Ile Tyr Asn Ala Lys Thr Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln His His Tyr
            100                 105                 110

Asp Ile Pro Trp Thr Phe Gly Gly Gly Thr Lys Leu Glu Ile Lys Arg
        115                 120                 125

Thr

<210> SEQ ID NO 60
<211> LENGTH: 129
<212> TYPE: PRT
<213> ORGANISM: Homo sapiens

<400> SEQUENCE: 60

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Thr Ser Glu Asn
        35                  40                  45

Ile Tyr Ser Tyr Leu Thr Trp Tyr Gln Gln Lys Pro Gly Lys Ala Pro
    50                  55                  60

Lys Leu Leu Ile Tyr Asn Ala Lys Ile Leu Asp Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln His His Tyr
            100                 105                 110

Asp Ile Pro Trp Thr Phe Gly Gly Gly Thr Lys Leu Glu Ile Lys Arg
        115                 120                 125

Thr

<210> SEQ ID NO 61
<211> LENGTH: 129
<212> TYPE: PRT
<213> ORGANISM: Homo sapiens

<400> SEQUENCE: 61

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Thr Ser Glu Asn
        35                  40                  45

```
            35                  40                  45
Ile Tyr Ser Tyr Leu Thr Trp Tyr Gln Gln Lys Pro Gly Lys Ala Pro
 50                  55                  60

Lys Leu Leu Ile Tyr His Ala Lys Ile Leu Asp Ser Gly Val Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Phe Ala Thr Tyr Tyr Cys Gln His His Tyr
                100                 105                 110

Asp Ile Pro Trp Thr Phe Gly Gly Gly Thr Lys Leu Glu Ile Lys Arg
                115                 120                 125

Thr

<210> SEQ ID NO 62
<211> LENGTH: 141
<212> TYPE: PRT
<213> ORGANISM: Homo sapiens

<400> SEQUENCE: 62

Met Glu Trp Ser Trp Val Phe Leu Phe Phe Leu Ser Val Thr Thr Gly
  1               5                  10                  15

Val His Ser Gln Val Gln Leu Gln Gln Pro Gly Thr Glu Leu Val Arg
                 20                  25                  30

Pro Gly Val Ser Val Lys Ile Ser Cys Lys Val Ser Gly Tyr Ala Phe
                 35                  40                  45

Thr Asp Tyr Ala Ile His Trp Ile Met Gln Ser His Ala Lys Ser Leu
 50                  55                  60

Glu Trp Ile Gly Ile Ile Asn Thr Tyr Tyr Gly Asp Ser Lys Tyr Asn
 65                  70                  75                  80

Gln Lys Phe Lys Asp Lys Ala Thr Met Thr Val Asp Lys Ser Ser Asn
                 85                  90                  95

Thr Ala Tyr Met Glu Leu Ala Arg Leu Thr Ser Glu Asp Ser Ala Ile
                100                 105                 110

Tyr Tyr Cys Ala Arg Gly Tyr Asp Gly Phe Ala Tyr Trp Gly Gln Gly
                115                 120                 125

Thr Leu Val Thr Val Ser Ser Ala Ser Thr Lys Gly Pro
                130                 135                 140

<210> SEQ ID NO 63
<211> LENGTH: 141
<212> TYPE: PRT
<213> ORGANISM: Homo sapiens

<400> SEQUENCE: 63

Met Glu Trp Ser Trp Val Phe Leu Phe Phe Leu Ser Val Thr Thr Gly
  1               5                  10                  15

Val His Ser Gln Val Gln Leu Val Gln Ser Gly Ala Glu Leu Lys Lys
                 20                  25                  30

Pro Gly Ala Ser Val Lys Val Ser Cys Lys Val Ser Gly Tyr Ala Phe
                 35                  40                  45

Thr Asp Tyr Ala Ile His Trp Ile Arg Gln Ala Pro Gly Gln Gly Leu
 50                  55                  60

Glu Trp Met Gly Ile Ile Asn Thr Tyr Tyr Gly Asp Ser Lys Tyr Asn
 65                  70                  75                  80

Gln Lys Phe Lys Asp Arg Val Thr Met Thr Val Asp Lys Ser Thr Ser
                 85                  90                  95
```

```
Thr Ala Tyr Met Glu Leu Ser Ser Leu Arg Ser Glu Asp Thr Ala Val
            100                 105                 110

Tyr Tyr Cys Ala Arg Gly Tyr Asp Gly Phe Ala Tyr Trp Gly Gln Gly
        115                 120                 125

Thr Leu Val Thr Val Ser Ser Ala Ser Thr Lys Gly Pro
    130                 135                 140

<210> SEQ ID NO 64
<211> LENGTH: 141
<212> TYPE: PRT
<213> ORGANISM: Homo sapiens

<400> SEQUENCE: 64

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Leu Lys Lys
            20                  25                  30

Pro Gly Ala Ser Val Lys Val Ser Cys Lys Val Ser Gly Tyr Ala Phe
        35                  40                  45

Thr Asp Tyr Ala Ile His Trp Ile Arg Gln Ala Pro Gly Gln Gly Leu
    50                  55                  60

Glu Trp Met Gly Ile Ile Asn Thr Tyr Tyr Gly Asp Ser Lys Tyr Ala
65                  70                  75                  80

Gln Lys Phe Gln Gly Arg Val Thr Met Thr Val Asp Thr Ser Thr Ser
            85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Gly Phe Ala Tyr Trp Gly Gln Gly
        115                 120                 125

Thr Leu Val Thr Val Ser Ser Ala Ser Thr Lys Gly Pro
    130                 135                 140

<210> SEQ ID NO 65
<211> LENGTH: 141
<212> TYPE: PRT
<213> ORGANISM: Homo sapiens

<400> SEQUENCE: 65

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Leu Lys Lys
            20                  25                  30

Pro Gly Ala Ser Val Lys Val Ser Cys Lys Val Ser Gly Tyr Ala Phe
        35                  40                  45

Thr Asp Tyr Ala Ile His Trp Val Arg Gln Ala Pro Gly Gln Gly Leu
    50                  55                  60

Glu Trp Met Gly Ile Ile Asn Thr Tyr Tyr Gly Asp Ser Lys Tyr Ala
65                  70                  75                  80

Gln Lys Phe Gln Gly Arg Val Thr Met Thr Val Asp Thr Ser Thr Ser
            85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Gly Phe Ala Tyr Trp Gly Gln Gly
        115                 120                 125

Thr Leu Val Thr Val Ser Ser Ala Ser Thr Lys Gly Pro
    130                 135                 140
```

<210> SEQ ID NO 66
<211> LENGTH: 141
<212> TYPE: PRT
<213> ORGANISM: Homo sapiens

<400> SEQUENCE: 66

```
Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ala Ile His Trp Val Arg Gln Ala Pro Gly Gln Gly Leu
    50                  55                  60

Glu Trp Met Gly Ile Ile Asn Thr Tyr Tyr Gly Asp Ser Lys Tyr Ala
65                  70                  75                  80

Gln Lys Phe Gln Gly Arg Val Thr Met Thr Val Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Gly Phe Ala Tyr Trp Gly Gln Gly
        115                 120                 125

Thr Leu Val Thr Val Ser Ser Ala Ser Thr Lys Gly Pro
    130                 135                 140
```

<210> SEQ ID NO 67
<211> LENGTH: 129
<212> TYPE: PRT
<213> ORGANISM: Homo sapiens

<400> SEQUENCE: 67

```
Met Ser Val Pro Thr Gln Val Leu Gly Leu Leu Leu Leu Trp Leu Thr
1               5                   10                  15

Asp Ala Arg Cys Asp Ile Gln Leu Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
    50                  55                  60

Gln Leu Leu Val Tyr Asn Ala Lys Thr Leu Ala Asp Asp Ile Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110

Ser Ala Pro Trp Thr Phe Gly Gly Gly Thr Lys Leu Glu Ile Lys Arg
        115                 120                 125

Thr
```

<210> SEQ ID NO 68
<211> LENGTH: 129
<212> TYPE: PRT
<213> ORGANISM: Homo sapiens

<400> SEQUENCE: 68

Met Ser Val Pro Thr Gln Val Leu Gly Leu Leu Leu Leu Trp Leu Thr

```
1               5                   10                  15
Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gly Asn
            35                  40                  45

Ile His Asn Tyr Leu Ala Trp Tyr Gln Gln Lys Pro Gly Lys Ala Pro
            50                  55                  60

Lys Leu Leu Ile Tyr Asn Ala Lys Thr Leu Ala Asp Val Pro Ser
 65                  70                  75                  80

Arg Phe Ser Gly Ser Gly Ser Gly Thr Asp Tyr Thr Leu Thr Ile Ser
            85                  90                  95

Ser Leu Gln Pro Glu Asp Phe Ala Thr Tyr Tyr Cys Gln His Phe Trp
            100                 105                 110

Ser Ala Pro Trp Thr Phe Gly Gly Gly Thr Lys Leu Glu Ile Lys Arg
            115                 120                 125

Thr

<210> SEQ ID NO 69
<211> LENGTH: 129
<212> TYPE: PRT
<213> ORGANISM: Homo sapiens

<400> SEQUENCE: 69

Met Ser Val Pro Thr Gln Val Leu Gly Leu Leu Leu Leu Trp Leu Thr
 1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gly Asn
            35                  40                  45

Ile His Asn Tyr Leu Ala Trp Tyr Gln Gln Lys Pro Gly Lys Ala Pro
            50                  55                  60

Lys Leu Leu Ile Tyr Asn Ala Lys Thr Leu Ala Asp Ala Val Pro Ser
 65                  70                  75                  80

Arg Phe Ser Gly Ser Gly Ser Gly Thr Asp Tyr Thr Leu Thr Ile Ser
            85                  90                  95

Ser Leu Gln Pro Glu Asp Phe Ala Thr Tyr Tyr Cys Gln His Phe Trp
            100                 105                 110

Ser Ala Pro Trp Thr Phe Gly Gly Gly Thr Lys Leu Glu Ile Lys Arg
            115                 120                 125

Thr

<210> SEQ ID NO 70
<211> LENGTH: 129
<212> TYPE: PRT
<213> ORGANISM: Homo sapiens

<400> SEQUENCE: 70

Met Ser Val Pro Thr Gln Val Leu Gly Leu Leu Leu Leu Trp Leu Thr
 1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gly Asn
            35                  40                  45

Ile His Asn Tyr Leu Ala Trp Tyr Gln Gln Lys Pro Gly Lys Ala Pro
            50                  55                  60
```

```
Lys Leu Leu Ile Tyr Asn Ala Lys Thr Leu Ala Asp Ala Val Pro Ser
 65                  70                  75                  80

Arg Phe Ser Gly Ser Gly Ser Gly Thr Asp Tyr Thr Leu Thr Ile Ser
                 85                  90                  95

Ser Leu Gln Pro Glu Asp Phe Ala Thr Tyr Tyr Cys Gln His Phe Trp
            100                 105                 110

Ser Ala Pro Trp Thr Phe Gly Gln Gly Thr Lys Leu Glu Ile Lys Arg
        115                 120                 125

Thr
```

```
<210> SEQ ID NO 71
<211> LENGTH: 129
<212> TYPE: PRT
<213> ORGANISM: Homo sapiens

<400> SEQUENCE: 71

Met Ser Val Pro Thr Gln Val Leu Gly Leu Leu Leu Trp Leu Thr
  1               5                  10                  15

Asp Ala Arg Cys Asp Ile Gln Met Thr Gln Ser Pro Ser Ser Leu Ser
             20                  25                  30

Ala Ser Val Gly Asp Arg Val Thr Ile Thr Cys Arg Ala Ser Gln Gly
         35                  40                  45

Ile His Asn Tyr Leu Ala Trp Tyr Gln Gln Lys Pro Gly Lys Ala Pro
     50                  55                  60

Lys Leu Leu Ile Tyr Asn Ala Lys Thr Leu Ala Asp Ala Val Pro Ser
 65                  70                  75                  80

Arg Phe Ser Gly Ser Gly Ser Gly Thr Asp Tyr Thr Leu Thr Ile Ser
                 85                  90                  95

Ser Leu Gln Pro Glu Asp Phe Ala Thr Tyr Tyr Cys Gln Gln Phe Trp
            100                 105                 110

Ser Ala Pro Trp Thr Phe Gly Gln Gly Thr Lys Leu Glu Ile Lys Arg
        115                 120                 125

Thr
```

```
<210> SEQ ID NO 72
<211> LENGTH: 144
<212> TYPE: PRT
<213> ORGANISM: Homo sapiens

<400> SEQUENCE: 72

Met Glu Trp Ser Trp Val Phe Leu Phe Phe Leu Ser Val Thr Thr Gly
  1               5                  10                  15

Val His Ser Gln Val Gln Leu Gln Gln Pro Gly Ala Glu Leu Val Arg
             20                  25                  30

Pro Gly Ala Ser Val Lys Leu Ser Cys Lys Ala Leu Gly Tyr Thr Phe
         35                  40                  45

Thr Asp Tyr Glu Met His Trp Val Lys Glu Thr Pro Val His Gly Leu
     50                  55                  60

Glu Trp Ile Gly Ala Ile Gln Pro Gly Gly Gly Thr Ala Tyr Asn
 65                  70                  75                  80

Gln Lys Phe Lys Gly Lys Ala Thr Leu Thr Ala Asp Lys Ser Ser Ser
                 85                  90                  95

Thr Ala Tyr Met Glu Leu Ser Ser Leu Thr Ser Glu Asp Ser Ala Val
            100                 105                 110

Tyr Tyr Cys Thr Arg Arg Gly Tyr Asp Asp Tyr Pro Phe Ala Tyr Trp
        115                 120                 125
```

Gly Gln Gly Thr Leu Val Thr Val Ser Ser Ala Ser Thr Lys Gly Pro
            130                 135                 140

<210> SEQ ID NO 73
<211> LENGTH: 144
<212> TYPE: PRT
<213> ORGANISM: Homo sapiens

<400> SEQUENCE: 73

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Leu Lys Lys
            20                  25                  30

Pro Gly Ser Ser Val Lys Val Ser Cys Lys Ala Ser Gly Tyr Thr Phe
        35                  40                  45

Thr Asp Tyr Glu Met His Trp Val Arg Gln Ala Pro Gly Gln Gly Leu
    50                  55                  60

Glu Trp Met Gly Ala Ile Gln Pro Gly Gly Gly Thr Ala Tyr Asn
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Arg Gly Tyr Asp Asp Tyr Pro Phe Ala Tyr Trp
        115                 120                 125

Gly Gln Gly Thr Leu Val Thr Val Ser Ser Ala Ser Thr Lys Gly Pro
    130                 135                 140

<210> SEQ ID NO 74
<211> LENGTH: 144
<212> TYPE: PRT
<213> ORGANISM: Homo sapiens

<400> SEQUENCE: 74

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Leu Lys Lys
            20                  25                  30

Pro Gly Ser Ser Val Lys Val Ser Cys Lys Ala Ser Gly Tyr Thr Phe
        35                  40                  45

Thr Asp Tyr Glu Met His Trp Val Arg Gln Ala Pro Gly Gln Gly Leu
    50                  55                  60

Glu Trp Met Gly Ala Ile Gln Pro Gly Gly Gly Thr Ala Tyr Ala
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Arg Gly Tyr Asp Asp Tyr Pro Phe Ala Tyr Trp
        115                 120                 125

Gly Gln Gly Thr Leu Val Thr Val Ser Ser Ala Ser Thr Lys Gly Pro
    130                 135                 140

<210> SEQ ID NO 75
<211> LENGTH: 144
<212> TYPE: PRT
<213> ORGANISM: Homo sapiens

<400> SEQUENCE: 75

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Glu Met His Trp Val Arg Gln Ala Pro Gly Gln Gly Leu
    50                  55                  60

Glu Trp Met Gly Ala Ile Gln Pro Gly Gly Gly Thr Ala Tyr Ala
65                  70                  75                  80

Gln Lys Phe Gln Gly Arg Val Thr Leu Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Arg Gly Tyr Asp Asp Tyr Pro Phe Ala Tyr Trp
        115                 120                 125

Gly Gln Gly Thr Leu Val Thr Val Ser Ser Ala Ser Thr Lys Gly Pro
    130                 135                 140

<210> SEQ ID NO 76
<211> LENGTH: 144
<212> TYPE: PRT
<213> ORGANISM: Homo sapiens

<400> SEQUENCE: 76

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Glu Met His Trp Val Arg Gln Ala Pro Gly Gln Gly Leu
    50                  55                  60

Glu Trp Met Gly Ala Ile Gln Pro Gly Gly Gly Thr Ala Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Arg Gly Tyr Asp Asp Tyr Pro Phe Ala Tyr Trp
        115                 120                 125

Gly Gln Gly Thr Leu Val Thr Val Ser Ser Ala Ser Thr Lys Gly Pro
    130                 135                 140

<210> SEQ ID NO 77
<211> LENGTH: 46
<212> TYPE: PRT
<213> ORGANISM: Homo sapiens

<400> SEQUENCE: 77

Thr Cys Asp Asp Tyr Tyr Tyr Gly Phe Gly Cys Asn Lys Phe Cys Arg
1               5                   10                  15

Pro Arg Asp Asp Phe Phe Gly His Tyr Ala Cys Asp Gln Asn Gly Asn
            20                  25                  30

```
Lys Thr Cys Met Glu Gly Trp Met Gly Pro Glu Cys Asn Arg
        35                  40                  45

<210> SEQ ID NO 78
<211> LENGTH: 46
<212> TYPE: PRT
<213> ORGANISM: Artificial Sequence
<220> FEATURE:
<223> OTHER INFORMATION: Description of Artificial Sequence: Synthetic
      Murine J1 sequence

<400> SEQUENCE: 78

Thr Cys Asp Asp His Tyr Tyr Gly Phe Gly Cys Asn Lys Phe Cys Arg
1               5                   10                  15

Pro Arg Asp Asp Phe Phe Gly His Tyr Ala Cys Asp Gln Asn Gly Asn
            20                  25                  30

Lys Thr Cys Met Glu Gly Trp Met Gly Pro Asp Cys Asn Lys
        35                  40                  45

<210> SEQ ID NO 79
<211> LENGTH: 9
<212> TYPE: PRT
<213> ORGANISM: Homo sapiens

<400> SEQUENCE: 79

Gln Gln His Tyr Ser Thr Pro Tyr Thr
1               5

<210> SEQ ID NO 80
<211> LENGTH: 9
<212> TYPE: PRT
<213> ORGANISM: Homo sapiens

<400> SEQUENCE: 80

Asn Ala Lys Thr Leu Ala Glu Gly Val
1               5

<210> SEQ ID NO 81
<211> LENGTH: 9
<212> TYPE: PRT
<213> ORGANISM: Homo sapiens

<400> SEQUENCE: 81

Gln His His Tyr Gly Thr Pro Trp Thr
1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 82

His His His His His His
1               5

<210> SEQ ID NO 83
<211> LENGTH: 151
<212> TYPE: PRT
<213> ORGANISM: Homo sapiens

<400> SEQUENCE: 83

Val Thr Cys Asp Asp Tyr Tyr Tyr Gly Phe Gly Cys Asn Lys Phe Cys
```

```
                1               5                   10                  15
Arg Pro Arg Asp Asp Phe Phe Gly His Tyr Ala Cys Asp Gln Asn Gly
                20                  25                  30

Asn Lys Thr Cys Met Glu Gly Trp Met Gly Pro Glu Cys Asn Arg Ala
            35                  40                  45

Ile Cys Arg Gln Gly Cys Ser Pro Lys His Gly Ser Cys Lys Leu Pro
        50                  55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Ile Cys Asn Glu Pro Trp
                85                  90                  95

Gln Cys Leu Cys Glu Thr Asn Trp Gly Gly Gln Leu Cys Asp Lys Asp
            100                 105                 110

Leu Asn Tyr Cys Gly Thr His Gln Pro Cys Leu Asn Gly Gly Thr Cys
        115                 120                 125

Ser Asn Thr Gly Pro Asp Lys Tyr Gln Cys Ser Cys Pro Glu Gly Tyr
    130                 135                 140

Ser Gly Pro Asn Cys Glu Ile
145                 150

<210> SEQ ID NO 84
<211> LENGTH: 151
<212> TYPE: PRT
<213> ORGANISM: Unknown
<220> FEATURE:
<223> OTHER INFORMATION: Description of Unknown:
      gibbon sequence

<400> SEQUENCE: 84

Val Thr Cys Asp Asp Tyr Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
                20                  25                  30

Asn Lys Thr Cys Met Glu Gly Trp Met Gly Pro Glu Cys Asn Arg Ala
            35                  40                  45

Ile Cys Arg Gln Gly Cys Ser Pro Lys His Gly Ser Cys Lys Leu Pro
        50                  55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Ile Cys Asn Glu Pro Trp
                85                  90                  95

Gln Cys Leu Cys Glu Thr Asn Trp Gly Gly Gln Leu Cys Asp Lys Asp
            100                 105                 110

Leu Asn Tyr Cys Gly Thr His Gln Pro Cys Leu Asn Gly Gly Thr Cys
        115                 120                 125

Ser Asn Thr Gly Pro Asp Lys Tyr Gln Cys Ser Cys Pro Glu Gly Tyr
    130                 135                 140

Ser Gly Pro Asn Cys Glu Ile
145                 150

<210> SEQ ID NO 85
<211> LENGTH: 151
<212> TYPE: PRT
<213> ORGANISM: Unknown
<220> FEATURE:
<223> OTHER INFORMATION: Description of Unknown:
      Monkey sequence
```

<400> SEQUENCE: 85

Val Thr Cys Asp Asp Tyr Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
            20                  25                  30

Asn Lys Thr Cys Met Glu Gly Trp Met Gly Pro Glu Cys Asn Arg Ala
        35                  40                  45

Ile Cys Arg Gln Gly Cys Ser Pro Lys His Gly Ser Cys Lys Leu Pro
50                  55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Ile Cys Asn Glu Pro Trp
                85                  90                  95

Gln Cys Leu Cys Glu Thr Asn Trp Gly Gly Gln Leu Cys Asp Lys Asp
            100                 105                 110

Leu Asn Tyr Cys Gly Thr His Gln Pro Cys Leu Asn Gly Gly Thr Cys
                115                 120                 125

Ser Asn Thr Gly Pro Asp Lys Tyr Gln Cys Ser Cys Pro Glu Gly Tyr
        130                 135                 140

Ser Gly Pro Asn Cys Glu Ile
145                 150

<210> SEQ ID NO 86
<211> LENGTH: 151
<212> TYPE: PRT
<213> ORGANISM: Pan troglodytes

<400> SEQUENCE: 86

Val Thr Cys Asp Asp Tyr Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
            20                  25                  30

Asn Lys Thr Cys Met Glu Gly Trp Met Gly Pro Glu Cys Asn Arg Ala
        35                  40                  45

Ile Cys Arg Gln Gly Cys Ser Pro Lys His Gly Ser Cys Lys Leu Pro
50                  55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Ile Cys Asn Glu Pro Trp
                85                  90                  95

Gln Cys Leu Cys Glu Thr Asn Trp Gly Gly Gln Leu Cys Asp Lys Asp
            100                 105                 110

Leu Asn Tyr Cys Gly Thr His Gln Pro Cys Leu Asn Gly Gly Thr Cys
                115                 120                 125

Ser Asn Thr Gly Pro Asp Lys Tyr Gln Cys Ser Cys Pro Glu Gly Tyr
        130                 135                 140

Ser Gly Pro Asn Cys Glu Ile
145                 150

<210> SEQ ID NO 87
<211> LENGTH: 151
<212> TYPE: PRT
<213> ORGANISM: Pongo sp.

<400> SEQUENCE: 87

Val Thr Cys Asp Asp Tyr Tyr Tyr Gly Phe Gly Cys Asn Lys Phe Cys

```
              1               5                  10                 15
Arg Pro Arg Asp Asp Phe Phe Gly His Tyr Ala Cys Asp Gln Asn Gly
                20                  25                  30

Asn Lys Thr Cys Met Glu Gly Trp Met Gly Pro Glu Cys Asn Arg Ala
                35                  40                  45

Ile Cys Arg Gln Gly Cys Ser Pro Lys His Gly Ser Cys Lys Leu Pro
            50                  55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Ile Cys Asn Glu Pro Trp
                85                  90                  95

Gln Cys Leu Cys Glu Thr Asn Trp Gly Gly Gln Leu Cys Asp Lys Asp
                100                 105                 110

Leu Asn Tyr Cys Gly Thr His Gln Pro Cys Leu Asn Gly Gly Thr Cys
                115                 120                 125

Ser Asn Thr Gly Pro Asp Lys Tyr Gln Cys Ser Cys Pro Glu Gly Tyr
        130                 135                 140

Ser Gly Pro Asn Cys Glu Ile
145                 150

<210> SEQ ID NO 88
<211> LENGTH: 151
<212> TYPE: PRT
<213> ORGANISM: Oryctolagus cuniculus

<400> SEQUENCE: 88

Val Thr Cys Asp Asp Tyr Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
                20                  25                  30

Asn Lys Thr Cys Met Glu Gly Trp Met Gly Pro Glu Cys Asn Arg Ala
                35                  40                  45

Ile Cys Arg Gln Gly Cys Ser Pro Lys His Gly Ser Cys Lys Leu Pro
            50                  55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Thr Cys Asn Glu Pro Trp
                85                  90                  95

Gln Cys Leu Cys Glu Thr Asn Trp Gly Gly Gln Leu Cys Asp Lys Asp
                100                 105                 110

Leu Asn Tyr Cys Gly Thr His Gln Pro Cys Leu Asn Gly Gly Thr Cys
                115                 120                 125

Ser Asn Thr Gly Pro Asp Lys Tyr Gln Cys Ser Cys Pro Glu Gly Tyr
        130                 135                 140

Ser Gly Pro Asn Cys Glu Ile
145                 150

<210> SEQ ID NO 89
<211> LENGTH: 151
<212> TYPE: PRT
<213> ORGANISM: Bos sp.

<400> SEQUENCE: 89

Val Thr Cys Asp Asp Tyr Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
```

```
                20                  25                  30
Asn Lys Thr Cys Met Glu Gly Trp Met Gly Pro Glu Cys Asn Lys Ala
            35                  40                  45

Ile Cys Arg Gln Gly Cys Ser Pro Lys His Gly Ser Cys Lys Leu Pro
    50                  55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Thr Cys Asn Glu Pro Trp
                85                  90                  95

Gln Cys Leu Cys Glu Thr Asn Trp Gly Gly Gln Leu Cys Asp Lys Asp
            100                 105                 110

Leu Asn Tyr Cys Gly Thr His Gln Pro Cys Leu Asn Gly Gly Thr Cys
        115                 120                 125

Ser Asn Thr Gly Pro Asp Lys Tyr Gln Cys Ser Cys Pro Glu Gly Tyr
    130                 135                 140

Ser Gly Pro Asn Cys Glu Ile
145                 150

<210> SEQ ID NO 90
<211> LENGTH: 151
<212> TYPE: PRT
<213> ORGANISM: Equus caballus

<400> SEQUENCE: 90

Val Thr Cys Asp Asp Tyr Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
            20                  25                  30

Asn Lys Thr Cys Val Glu Gly Trp Met Gly Pro Glu Cys Asn Lys Ala
        35                  40                  45

Ile Cys Arg Gln Gly Cys Ser Pro Lys His Gly Ser Cys Lys Leu Pro
    50                  55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Thr Cys Asn Glu Pro Trp
                85                  90                  95

Gln Cys Leu Cys Glu Thr Asn Trp Gly Gly Gln Leu Cys Asp Lys Asp
            100                 105                 110

Leu Asn Tyr Cys Gly Thr His Gln Pro Cys Leu Asn Gly Gly Thr Cys
        115                 120                 125

Ser Asn Thr Gly Pro Asp Lys Tyr Gln Cys Ser Cys Pro Glu Gly Tyr
    130                 135                 140

Ser Gly Pro Asn Cys Glu Ile
145                 150

<210> SEQ ID NO 91
<211> LENGTH: 151
<212> TYPE: PRT
<213> ORGANISM: Unknown
<220> FEATURE:
<223> OTHER INFORMATION: Description of Unknown:
      elephant sequence

<400> SEQUENCE: 91

Val Thr Cys Asp Asp Tyr Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
```

```
                20                  25                  30

Asn Lys Thr Cys Met Glu Gly Trp Met Gly Pro Glu Cys Asn Arg Ala
            35                  40                  45

Ile Cys Arg Gln Gly Cys Ser Pro Lys His Gly Ser Cys Lys Leu Pro
        50                  55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Thr Cys Val Glu Pro Trp
                85                  90                  95

Gln Cys Leu Cys Glu Thr Asn Trp Gly Gly Gln Leu Cys Asp Lys Asp
            100                 105                 110

Leu Asn Tyr Cys Gly Thr His Gln Pro Cys Leu Asn Gly Gly Thr Cys
        115                 120                 125

Ser Asn Thr Gly Pro Asp Lys Tyr Gln Cys Ser Cys Pro Glu Gly Tyr
    130                 135                 140

Ser Gly Pro Asn Cys Glu Ile
145                 150

<210> SEQ ID NO 92
<211> LENGTH: 151
<212> TYPE: PRT
<213> ORGANISM: Canis lupus

<400> SEQUENCE: 92

Val Thr Cys Asp Asp Tyr Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
                20                  25                  30

Asn Lys Thr Cys Met Glu Gly Trp Met Gly Pro Glu Cys Asn Lys Ala
            35                  40                  45

Ile Cys Arg Gln Gly Cys Ser Pro Lys His Gly Ser Cys Lys Leu Pro
        50                  55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Thr Cys Asn Glu Pro Trp
                85                  90                  95

Gln Cys Leu Cys Glu Thr Asn Trp Gly Gly Gln Leu Cys Asp Lys Asp
            100                 105                 110

Leu Asn Tyr Cys Gly Thr Arg Gln Pro Cys Leu Asn Gly Gly Thr Cys
        115                 120                 125

Ser Asn Thr Gly Pro Asp Lys Tyr Gln Cys Ser Cys Pro Glu Gly Tyr
    130                 135                 140

Ser Gly Pro Asn Cys Glu Ile
145                 150

<210> SEQ ID NO 93
<211> LENGTH: 151
<212> TYPE: PRT
<213> ORGANISM: Sus scrofa

<400> SEQUENCE: 93

Val Thr Cys Asp Glu His Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
                20                  25                  30

Asn Lys Thr Cys Met Glu Gly Trp Met Gly Pro Glu Cys Asn Lys Ala
```

```
                35                  40                  45
Ile Cys Arg Gln Gly Cys Ser Pro Lys His Gly Ser Cys Lys Leu Pro
 50                  55                  60

Gly Asp Cys Arg Cys Gln Tyr Gly Trp Gln Gly Leu Tyr Cys Asp Lys
 65                  70                  75                  80

Cys Ile Pro His Pro Gly Cys Val His Gly Thr Cys Asn Glu Pro Trp
                 85                  90                  95

Gln Cys Leu Cys Glu Thr Asn Trp Gly Gln Leu Cys Asp Lys Asp
                100                 105                 110

Leu Asn Tyr Cys Gly Thr His Gln Pro Cys Leu Asn Gly Gly Thr Cys
                115                 120                 125

Ser Asn Thr Gly Pro Asp Lys Tyr Gln Cys Ser Cys Pro Glu Gly Tyr
                130                 135                 140

Ser Gly Pro Asn Cys Glu Ile
145                 150

<210> SEQ ID NO 94
<211> LENGTH: 151
<212> TYPE: PRT
<213> ORGANISM: Unknown
<220> FEATURE:
<223> OTHER INFORMATION: Description of Unknown:
      hamster sequence

<400> SEQUENCE: 94

Val Thr Cys Asp Asp His Tyr Tyr Gly Phe Gly Cys Asn Lys Phe Cys
 1                   5                  10                  15

Arg Pro Arg Asp Asp Phe Phe Gly His Tyr Ala Cys Asp Gln Asn Gly
                 20                  25                  30

Asn Lys Thr Cys Met Glu Gly Trp Met Gly Pro Glu Cys Asn Lys Ala
                 35                  40                  45

Ile Cys Arg Gln Gly Cys Ser Pro Lys His Gly Ser Cys Lys Leu Pro
 50                  55                  60

Gly Asp Cys Arg Cys Gln Tyr Gly Trp Gln Gly Leu Tyr Cys Asp Lys
 65                  70                  75                  80

Cys Ile Pro His Pro Gly Cys Val His Gly Thr Cys Asn Glu Pro Trp
                 85                  90                  95

Gln Cys Leu Cys Glu Thr Asn Trp Gly Gln Leu Cys Asp Lys Asp
                100                 105                 110

Leu Asn Tyr Cys Gly Thr His Gln Pro Cys Leu Asn Arg Gly Thr Cys
                115                 120                 125

Ser Asn Thr Gly Pro Asp Lys Tyr Gln Cys Ser Cys Pro Glu Gly Tyr
                130                 135                 140

Ser Gly Pro Asn Cys Glu Ile
145                 150

<210> SEQ ID NO 95
<211> LENGTH: 151
<212> TYPE: PRT
<213> ORGANISM: Rattus norvegicus

<400> SEQUENCE: 95

Val Thr Cys Asp Asp His Tyr Tyr Gly Phe Gly Cys Asn Lys Phe Cys
 1                   5                  10                  15

Arg Pro Arg Asp Asp Phe Phe Gly His Tyr Ala Cys Asp Gln Asn Gly
                 20                  25                  30
```

```
Asn Lys Thr Cys Met Glu Gly Trp Met Gly Pro Glu Cys Asn Lys Ala
            35                  40                  45

Ile Cys Arg Gln Gly Cys Ser Pro Lys His Gly Ser Cys Lys Leu Pro
 50                  55                  60

Gly Asp Cys Arg Cys Gln Tyr Gly Trp Gln Gly Leu Tyr Cys Asp Lys
 65                  70                  75                  80

Cys Ile Pro His Pro Gly Cys Val His Gly Thr Cys Asn Glu Pro Trp
                 85                  90                  95

Gln Cys Leu Cys Glu Thr Asn Trp Gly Gly Gln Leu Cys Asp Lys Asp
            100                 105                 110

Leu Asn Tyr Cys Gly Thr His Gln Pro Cys Leu Asn Arg Gly Thr Cys
            115                 120                 125

Ser Asn Thr Gly Pro Asp Lys Tyr Gln Cys Ser Cys Pro Glu Gly Tyr
            130                 135                 140

Ser Gly Pro Asn Cys Glu Ile
145                 150

<210> SEQ ID NO 96
<211> LENGTH: 151
<212> TYPE: PRT
<213> ORGANISM: Ailuropoda melanoleuca

<400> SEQUENCE: 96

Val Thr Cys Asp Asp Tyr Tyr Tyr Gly Phe Gly Cys Asn Lys Phe Cys
 1               5                  10                  15

Arg Pro Arg Asp Asp Phe Phe Gly His Tyr Ala Cys Asp Gln Asn Gly
            20                  25                  30

Asn Lys Thr Cys Met Glu Gly Trp Met Gly Pro Glu Cys Asn Arg Ala
            35                  40                  45

Ile Cys Arg Gln Gly Cys Ser Pro Lys His Gly Ser Cys Lys Leu Pro
 50                  55                  60

Gly Asp Cys Arg Cys Gln Tyr Gly Trp Gln Gly Leu Tyr Cys Asp Lys
 65                  70                  75                  80

Cys Ile Pro His Pro Gly Cys Val His Gly Thr Cys Asn Glu Pro Trp
                 85                  90                  95

Gln Cys Leu Cys Glu Thr Asn Trp Gly Gly Gln Leu Cys Asp Lys Asp
            100                 105                 110

Leu Asn Tyr Cys Gly Thr Arg Gln Pro Cys Leu Asn Gly Gly Thr Cys
            115                 120                 125

Ser Asn Thr Gly Pro Asp Lys Tyr Gln Cys Ser Cys Pro Glu Gly Tyr
            130                 135                 140

Ser Gly Ser Asn Cys Glu Ile
145                 150

<210> SEQ ID NO 97
<211> LENGTH: 151
<212> TYPE: PRT
<213> ORGANISM: Cavia sp.

<400> SEQUENCE: 97

Val Thr Cys Asp Asp Tyr Tyr Tyr Gly Phe Gly Cys Asn Lys Phe Cys
 1               5                  10                  15

Arg Pro Arg Asp Asp Phe Phe Gly His Tyr Ala Cys Asp Gln Asn Gly
            20                  25                  30

Asn Lys Thr Cys Met Glu Gly Trp Met Gly Pro Glu Cys Asn Lys Ala
            35                  40                  45
```

```
Ile Cys Arg Gln Gly Cys Ser Pro Lys His Gly Ser Cys Lys Ile Pro
    50              55                  60

Gly Asn Cys Arg Cys Gln Tyr Gly Trp Gln Gly Leu Tyr Cys Asp Lys
65                  70                  75                  80

Cys Ile Pro His Pro Gly Cys Val His Gly Thr Cys Ile Glu Pro Trp
                85              90                  95

Gln Cys Leu Cys Glu Thr Asn Trp Gly Gly Gln Leu Cys Asp Lys Asp
            100                 105                 110

Leu Asn Tyr Cys Gly Thr His Gln Pro Cys Leu Asn Gly Gly Thr Cys
        115                 120             125

Ser Asn Thr Gly Pro Asp Lys Tyr Gln Cys Ser Cys Pro Glu Gly Tyr
    130             135                 140

Ser Gly Pro Asn Cys Glu Ile
145             150

<210> SEQ ID NO 98
<211> LENGTH: 151
<212> TYPE: PRT
<213> ORGANISM: Mus musculus

<400> SEQUENCE: 98

Val Thr Cys Asp Asp His Tyr Tyr Gly Phe Gly Cys Asn Lys Phe Cys
1               5                   10                  15

Arg Pro Arg Asp Asp Phe Phe Gly His Tyr Ala Cys Asp Gln Asn Gly
                20                  25                  30

Asn Lys Thr Cys Met Glu Gly Trp Met Gly Pro Asp Cys Asn Lys Ala
            35                  40                  45

Ile Cys Arg Gln Gly Cys Ser Pro Lys His Gly Ser Cys Lys Leu Pro
    50              55                  60

Gly Asp Cys Arg Cys Gln Tyr Gly Trp Gln Gly Leu Tyr Cys Asp Lys
65                  70                  75                  80

Cys Ile Pro His Pro Gly Cys Val His Gly Thr Cys Asn Glu Pro Trp
                85              90                  95

Gln Cys Leu Cys Glu Thr Asn Trp Gly Gly Gln Leu Cys Asp Lys Asp
            100                 105                 110

Leu Asn Tyr Cys Gly Thr His Gln Pro Cys Leu Asn Arg Gly Thr Cys
        115                 120             125

Ser Asn Thr Gly Pro Asp Lys Tyr Gln Cys Ser Cys Pro Glu Gly Tyr
    130             135                 140

Ser Gly Pro Asn Cys Glu Ile
145             150
```